US009630949B2

United States Patent
Bouix-Peter et al.

(10) Patent No.: US 9,630,949 B2
(45) Date of Patent: *Apr. 25, 2017

(54) OXOAZETIDINE DERIVATIVES, PROCESS FOR THE PREPARATION THEREOF AND USE THEREOF IN HUMAN MEDICINE AND IN COSMETICS

(71) Applicant: GALDERMA RESEARCH & DEVELOPMENT, Biot (FR)

(72) Inventors: Claire Bouix-Peter, Le Cannet (FR); Itaru Suzuki, Fayence (FR); Nicolas Rodeville, Biot (FR); Pascale Mauvais, Antibes (FR); Jean-Claude Pascal, Nice (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 44 days.

This patent is subject to a terminal disclaimer.

(21) Appl. No.: 14/497,600

(22) Filed: Sep. 26, 2014

(65) Prior Publication Data

US 2015/0045559 A1 Feb. 12, 2015

Related U.S. Application Data

(63) Continuation of application No. 13/127,643, filed as application No. PCT/EP2009/064646 on Nov. 4, 2009, now Pat. No. 8,871,187.

(60) Provisional application No. 61/111,130, filed on Nov. 4, 2008.

(30) Foreign Application Priority Data

Nov. 4, 2008 (FR) ...................................... 08 57496

(51) Int. Cl.
| | |
|---|---|
| *C07D 403/12* | (2006.01) |
| *A61K 8/49* | (2006.01) |
| *A61K 31/4178* | (2006.01) |
| *A61Q 5/10* | (2006.01) |
| *A61Q 17/04* | (2006.01) |
| *A61Q 19/00* | (2006.01) |
| *A61Q 19/02* | (2006.01) |
| *A61Q 19/04* | (2006.01) |
| *C07D 401/12* | (2006.01) |

(52) U.S. Cl.
CPC ............ *C07D 403/12* (2013.01); *A61K 8/494* (2013.01); *A61K 8/4906* (2013.01); *A61K 31/4178* (2013.01); *A61Q 5/10* (2013.01); *A61Q 17/04* (2013.01); *A61Q 19/004* (2013.01); *A61Q 19/007* (2013.01); *A61Q 19/008* (2013.01); *A61Q 19/02* (2013.01); *A61Q 19/04* (2013.01); *C07D 401/12* (2013.01); *A61K 2800/78* (2013.01)

(58) Field of Classification Search
None
See application file for complete search history.

(56) References Cited

U.S. PATENT DOCUMENTS

2004/0006067 A1    1/2004   Fotsch et al.

FOREIGN PATENT DOCUMENTS

| FR | 2867684 A1 | 9/2005 |
|---|---|---|
| WO | 01/28555 A1 | 4/2001 |
| WO | 2002070511 A1 | 9/2002 |
| WO | 03/032976 A1 | 4/2003 |
| WO | 2005047251 A1 | 5/2005 |
| WO | 2005047253 A1 | 5/2005 |

OTHER PUBLICATIONS

International Search Report for corresponding PCT/EP2009/064646 dated Mar. 1, 2010.

*Primary Examiner* — Kamal Saeed
(74) *Attorney, Agent, or Firm* — Dentons US LLP

(57) ABSTRACT

The present invention relates to novel compounds derived from oxoazetidine corresponding to general formula (I) to the compositions containing same, to the process for preparation thereof and to the use thereof in pharmaceutical or cosmetic compositions.

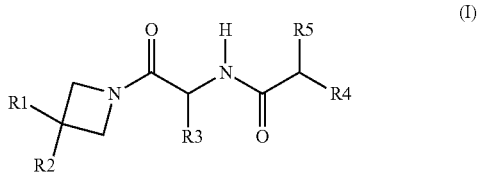

19 Claims, No Drawings

OXOAZETIDINE DERIVATIVES, PROCESS FOR THE PREPARATION THEREOF AND USE THEREOF IN HUMAN MEDICINE AND IN COSMETICS

This application is a continuation of U.S. patent application Ser. No. 13/127,643, filed Jul. 27, 2011, now U.S. Pat. No. 8,871,187, which is the United States national phase of PCT/EP2009/064646, filed Nov. 4, 2009, and designating the United States (published in the English language on May 14, 2010, as WO 2010/052253 A1), which claims priority under 35 U.S.C. §119 U.S. Provisional Application No. 61/111,130, filed Nov. 4, 2008, and of FR 0857496, filed Nov. 4, 2008.

The invention relates to novel compounds as products that modulate one or more melanocortin receptor(s). It also relates to the process for the preparation thereof and to the therapeutic use thereof.

Melanocortins make up the family of regulatory peptides which are synthesized by post-translational processing of the hormone proopiomelanocortin (POMC—131 amino acids long). POMC results in the production of 3 classes of hormones, melanocortins, the hormone adrenocorticotropin and various endorphins, such as, for example, ligotropin (Cone, et al., Recent Prog. Horm. Res., 51:287-317, (1996); Cone et al., Ann. N.Y. Acad. Sd., 31:342-363 (1993)).

Melanocortin receptors (MCRs) form part of the 7-transmembrane domain GPCR superfamily. To date, 5 receptor subtypes, MC1-5R, have been identified in mammals. An endogenous group of peptides binds to MCRs with agonist or antagonist effects, such as melanocyte-stimulating hormones (MSH), adrenocorticotropic hormone (ACTH), and Agouti proteins and derivatives thereof. One exception, however, is the MC2R receptor, which binds only with ACTH (Major pharmacological distinction of the ACTH receptor from other melanocortin receptors, Schioth et al. Life sciences (1996), 59(10), 797-801).

MCRs have varied roles at the physiological level. MC1R regulates melanin formation in the skin, and has a role in immune system regulation. MC2R regulates corticosteroid production at the level of the adrenal glands. The MC3R and MC4R receptors play a role in the control of food intake and sexual behaviour. MC5R is involved in exocrine gland regulation (Wikberg, Jarl E. S., Melanocortin receptors: perspectives for novel drugs. European Journal of Pharmacology (1999), 375(1-3) 295-310. Wikberg, Jarl E. S., Melanocortin receptors: new opportunities in drug discovery. Expert Opinion on Therapeutic Patents (2001), 11(1), 61-76).

The potential use of MCRs as a target for medicaments intended to treat significant pathological compositions such as obesity, diabetes, inflammatory conditions and sexual dysfunction creates a need for compounds which show great specificity with respect to a particular subtype. However, the modelling of medicaments that are selective for slightly different receptor subtypes is a difficult task that would be simplified if detailed knowledge of the determinants of the ligand-receptor interaction was available.

The Applicant has now discovered, unexpectedly and surprisingly, that novel compounds of general formula (I) as defined hereinafter exhibit very good activity on melanocortin receptors, and in particular certain compounds are highly selective for MC1R.

It has been demonstrated in particular that MC1R is one of the key proteins in the regulation of melanin synthesis in melanocytes.

MC1R is expressed in melanocytes and is involved in skin pigmentation, the colouration of animal fur and melanocyte functions. Melanocortins can thus be used to treat hypopigmentary and hyperpigmentary disorders. MC1R gene polymorphism data have been associated with the auburn hair phenotype and with malignant and non-malignant skin cancers (Xu X et al Nat Genet 1996; 14: 384; Van Der Velden P A et al Am J Hum Gent 2001; 69; 774-779; Valverde P et al Hum Mol Genet 1996; 5; 1663-1666; Schioth H B Biochem Biophys Res Commun 1999; 260: 488-491; Scott M C et al J Cell Sci 2002; 115; 2349-2355). Thus, a link exists between MC1R and melanoma; as a result, MC1R may be important in the prevention and treatment of certain forms of skin cancer (Stockfleth E et al Recent Results Cancer Res 2002; 160; 259-268; Stander et al Exp Dermatol 2002; 11: 42-51). MC1R is also expressed in macrophages and monocytes (Star et al Proc. Natl. Acad. Sci. USA 92; 8016-8020; Hartmeyer et al J. Immunol. 159; 1930-1937), neutrophils (Catania et al Peptides 17; 675-679), endothelial cells (Hartmeyer et al J. Immunol. 159; 1930-1937), glioma cells and astrocytes (Wong et al Neuroimmunomodulation 4, 37-41), fibroblasts (Boston and Cone, Endocrinology 137, 2043-2050) and keratinocytes (Luger et al J. Invest Dermatol. Symp. Proc. 2, 87-93). The localization of MC1R in these cells is associated with the ability of MSH-derived peptides to inhibit inflammatory processes. Specifically, α-MSH has shown a strong inhibition of inflammation in chronic models of intestinal inflammation, of arthritis, of ischaemia, of contact hypersensitivity and of dermatitis, and is also capable of inducing tolerance to haptens (Ceriana et al Neuroimmunomodulation 1, 28-32; Chiao et al. Clin. Invest. 99, 1165-1172; Huh and Lipton Neurosurgery 40, 132-139; Luger et al. J. Invest Dermatol. Symp. Proc. 2, 87-93; Rajora et al Peptides 18, 381-385; J. Neurosci. 17, 2181-2196; Lipton et al. Neuroimmunomodulation 5, 178-183). Melanocortins can thus be used to treat inflammatory disorders and immune disorders. It has been suggested that the MC1R signalling pathway plays a role in the perception of pain and that functional variations in MC1R are associated with a high pain tolerance (Mogil et al J Med Genet. 2005 July; 42(7): 583-7).

A strong correlation exists between human hair colour and MC1R variants (Valverde et al Nat Genet. 1995 November; 11(3): 328-30). Functional variations in MC1R are associated with the auburn hair colour.

It is also known that the sebaceous gland expresses both MC1R (Ganceviciene et al Exp Dermatol. 2007 July; 16(7): 547-52) and MC5R (Zhang et al Peptides. 2006 February; 27(2): 413-20). It has also been reported that MC1R is overexpressed in the sebaceous gland in the case of acne.

These compounds find uses in human medicine, in particular in dermatology, and in the cosmetics field.

Among the oxoazetidine derivatives already known, some have been described as having antibacterial properties (WO9709328, WO04045616, WO04087697), antiviral properties as CCR5 antagonists (WO04055016, WO08034731) and analgesic properties (Journal of Medicinal Chemistry (1968), 11, 466-470).

Patent WO9810653 discloses certain piperidine, pyrrolidine and hexahydro-1H-azepin compounds for promoting the synthesis of growth hormone in humans and animals.

Patents WO9635713 and WO9638471 disclose certain dipeptides for stimulating growth hormone synthesis.

The publication in the Journal of Medicinal Chemistry (2003), 46, 1123-1126 describes the "discovery of tyrosine-based potent and selective MC1R receptor small-molecule agonists with anti-inflammatory properties".

Patents WO02070511, WO02079146 and WO02069905 claim the use of compounds as modulators of melanocortin receptors, more particularly MC1R and MC4R.

Now, the Applicant has found, unexpectedly and surprisingly, that certain compounds of formula (I), which are the subject of the present invention, are modulators of one or more melanocortin receptors and, in particular, some compounds are highly selective for MC1R.

Thus, the present invention relates to compounds of general formula (I) below:

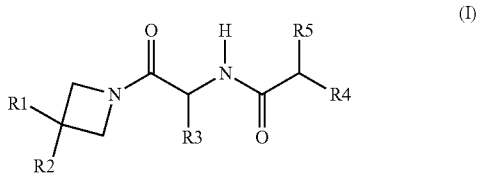

in which:
R1 represents an aryl, a substituted aryl or a cycloalkyl;
R2 represents a hydrogen atom, a hydroxyl, a lower alkyl, a substituted lower alkyl, a higher alkyl, a substituted higher alkyl, a cycloalkyl, a cycloalkylalkyl, a lower alkoxy, a substituted lower alkoxy, a higher alkoxy, a substituted higher alkoxy, a cycloalkylalkoxy, or an acyloxy;
R3 represents an aralkyl or a substituted aralkyl;
R4 represents a heteroalkyl, a substituted heteroaralkyl, a heteroalkyl or a substituted heteroalkyl;
R5 represents a hydrogen atom, a hydroxyl, an amino, an acylamino or a sulphonamide; and also the corresponding salts and enantiomers of the compounds of general formula (I).

Among the addition salts of the compounds of general formula (I) with a pharmaceutically acceptable acid, mention may preferably be made of the salts with an organic acid or with an inorganic acid.

Suitable inorganic acids are, for example, hydrohalic acids such as hydrochloric acid or hydrobromic acid, sulphuric acid, or nitric acid.

Suitable organic acids are, for example, picric acid, methanesulphonic acid, ethanesulphonic acid, para-toluenesulphonic acid, citric acid, oxalic acid or tartaric acid.

The compounds of general formula (I) may also exist in the form of hydrates or of solvates with water or with a solvent.

Appropriate solvents for forming solvates or hydrates are, for example, alcohols such as ethanol or isopropanol, or water.

According to the present invention, the term "aryl" denotes an unsubstituted phenyl or naphthyl.

According to the present invention, the term "substituted aryl" denotes a phenyl or a naphthyl substituted with one or more groups of atoms chosen from an alkyl, an alkoxy, a halogen, a hydroxyl, a cyano, a trifluoromethyl and a nitro.

According to the present invention, the term "cycloalkyl" denotes a cyclic, saturated hydrocarbon-based chain containing from 3 to 7 carbon atoms.

According to the present invention, the term "hydroxyl" denotes the OH group.

According to the present invention, the term "amino" denotes the $NH_2$ group.

According to the present invention, the term "acyl" denotes a formyl or a carbonyl substituted with an alkyl.

According to the present invention, the term "sulphonyl" denotes a sulphone substituted with an alkyl.

According to the present invention, the term "lower alkyl" denotes a linear or branched, saturated hydrocarbon-based chain containing from 1 to 4 carbon atoms or a linear or branched, unsaturated hydrocarbon-based chain containing from 2 to 4 carbon atoms.

According to the present invention, the term "alkyl" denotes a substituted or unsubstituted lower alkyl or higher alkyl.

According to the present invention, the term "substituted lower alkyl" denotes a linear or branched, saturated hydrocarbon-based chain containing from 1 to carbon atoms, or a linear or branched, unsaturated hydrocarbon-based chain containing from 2 to 4 carbon atoms, and substituted with one or more halogen atoms or with a hydroxyl, and in particular, for example, methyl, ethyl, propyl, isopropyl or butyl.

According to the present invention, the term "higher alkyl" denotes a linear or branched, saturated or unsaturated hydrocarbon-based chain containing from 5 to 10 carbon atoms.

According to the present invention, the term "substituted higher alkyl" is intended to mean a linear or branched, saturated or unsaturated hydrocarbon-based chain containing from 5 to 10 carbon atoms and substituted with one or more halogen atoms or with a hydroxyl.

According to the present invention, the term "cycloalkylalkyl" denotes an alkyl substituted with a cycloalkyl.

According to the present invention, the term "lower alkoxy" denotes an oxygen atom substituted with a lower alkyl, and in particular, for example, methoxy, ethoxy, propoxy, isopropoxy or butoxy.

According to the present invention, the term "substituted lower alkoxy" denotes an oxygen atom substituted with a substituted lower alkyl.

According to the present invention, the term "higher alkoxy" denotes an oxygen atom substituted with a higher alkyl.

According to the present invention, the term "substituted higher alkoxy" denotes an oxygen atom substituted with a substituted higher alkyl.

According to the present invention, the term "cycloalkylalkoxy" denotes an oxygen atom substituted with a cycloalkylalkyl.

According to the present invention, the term "acyloxy" denotes an oxygen atom substituted with an acyl.

According to the present invention, the term "aralkyl" denotes an alkyl substituted with an aryl.

According to the present invention, the term "substituted aralkyl" denotes an alkyl substituted with a substituted aryl.

According to the present invention, the term "halogen atom" denotes chlorine, fluorine, iodine and bromine atoms.

According to the present invention, the term "heterocycle" denotes a saturated or unsaturated, cyclic or bicyclic hydrocarbon-based chain comprising one or more heteroatoms chosen from O, S and N.

According to the present invention, the term "substituted heterocycle" denotes a saturated or unsaturated, cyclic or bicyclic hydrocarbon-based chain comprising one or more heteroatoms chosen from O, S and N, substituted with one or more alkyl groups.

According to the present invention, the term "heteroaryl" denotes an aromatic heterocycle.

According to the present invention, the term "substituted heteroaryl" denotes an aromatic heterocycle substituted with one or more alkyl groups.

According to the present invention, the term "heteroaralkyl" denotes an alkyl substituted with a heteroaryl.

According to the present invention, the term "substituted heteroaralkyl" denotes an alkyl substituted with a substituted heteroaryl.

According to the present invention, the term "heteroalkyl" denotes an alkyl substituted with a heterocycle.

According to the present invention, the term "substituted heteroalkyl" denotes an alkyl substituted with a substituted heterocycle.

According to the present invention, the term "acylamino groups" denotes an amine substituted with an acyl.

According to the present invention, the term "sulphonamide groups" denotes an amine substituted with a sulphonyl group.

Among the compounds of general formula (I) which fall within the context of the present invention, mention may in particular be made of the following:

1-[(S)-2-[(S)-2-benzoylamino-3-(1H-imidazol-4-yl)propionylamino]-3-(4-methoxyphenyl)propionyl]-3-phenylazetidin-3-yl ester of butyric acid N—[(S)-1-[(S)-2-(3-butoxy-3-o-tolylazetidin-1-yl)-1-(4-methoxybenzyl)-2-oxoethylcarbamoyl]-2-(1H-imidazol-4-yl)ethyl]benzamide N—[(S)-1-[(S)-2-(3-butoxy-3-phenylazetidin-1-yl)-1-(4-methoxybenzyl)-2-oxoethylcarbamoyl]-2-(1H-imidazol-4-yl)ethyl]benzamide N—[(S)-1-[(S)-2-(3-hydroxy-3-o-tolylazetidin-1-yl)-1-(4-methoxybenzyl)-2-oxoethylcarbamoyl]-2-(1H-imidazol-4-yl)ethyl]benzamide 1-[(S)-2-[(S)-2-benzoyl amino-3-(1H-imidazol-4-yl)propionylamino]-3-(4-methoxyphenyl)propionyl]-3-o-tolylazetidin-3-yl acetate 1-[(S)-2-[(S)-2-benzoylamino-3-(1H-imidazol-4-yl)propionylamino]-3-(4-methoxyphenyl)propionyl]-3-(4-fluorophenyl)azetidin-3-yl ester of butyric acid N—[(S)-1-[(S)-2-(3-cyclohexyl-3-hydroxyazetidin-1-yl)-1-(4-methoxybenzyl)-2-oxoethylcarbamoyl]-2-(1H-imidazol-4-yl)ethyl]benzamide N—[(S)-1-[(S)-2-[3-butoxy-3-(4-fluorophenyl)azetidin-1-yl]-1-(4-methoxybenzyl)-2-oxoethylcarbamoyl]-2-(1H-imidazol-4-yl)ethyl]benzamide N—[(S)-1-[(S)-2-[3-butoxy-3-(3-fluorophenyl)azetidin-1-yl]-1-(4-methoxybenzyl)-2-oxoethylcarbamoyl]-2-(1H-imidazol-4-yl)ethyl]benzamide N—[(S)-2-(3-cyclohexyl-3-hydroxyazetidin-1-yl)-1-(4-methoxybenzyl)-2-oxoethyl]-3-(1H-imidazol-4-yl)propionamide N—[(S)-2-(3-hydroxy-3-o-tolylazetidin-1-yl)-1-(4-methoxybenzyl)-2-oxoethyl]-3-(1H-imidazol-4-yl)propionamide N—[(R)-1-(3,4-dichlorobenzyl)-2-(3-hydroxy-3-phenylazetidin-1-yl)-2-oxoethyl]-3-(1H-imidazol-4-yl)-propionamide N—[(S)-2-(3-ethoxy-3-o-tolylazetidin-1-yl)-1-(4-methoxybenzyl)-2-oxoethyl]-3-(1H-imidazol-4-yl)-propionamide N—[(S)-2-(3-cyclopropylmethoxy-3-o-tolylazetidin-1-yl)-1-(4-methoxybenzyl)-2-oxoethyl]-3-(1H-imidazol-4-yl)propionamide N—[(R)-2-(3-butoxy-3-o-tolylazetidin-1-yl)-1-(4-methoxybenzyl)-2-oxoethyl]-3-(1H-imidazol-4-yl)propionamide N—[(S)-2-(3-butoxy-3-o-tolylazetidin-1-yl)-1-(4-methoxybenzyl)-2-oxoethyl]-3-(1H-imidazol-4-yl)propionamide N—[(R)-2-(3-ethoxy-3-o-tolylazetidin-1-yl)-1-(4-methoxybenzyl)-2-oxoethyl]-3-(1H-imidazol-4-yl)propionamide N—[(R)-2-(3-butoxy-3-phenylazetidin-1-yl)-1-cyclohexylmethyl-2-oxoethyl]-3-(1H-imidazol-4-yl)propionamide N—[(R)-2-(3-butoxy-3-phenylazetidin-1-yl)-1-(2,4-dichlorobenzyl)-2-oxoethyl]-3-(1H-imidazol-4-yl)propionamide N—[(R)-2-(3-cyclopropylmethoxy-3-o-tolylazetidin-1-yl)-1-(4-methoxybenzyl)-2-oxoethyl]-3-(1H-imidazol-4-yl)propionamide N—[(S)-1-(4-methoxybenzyl)-2-oxo-2-(3-propoxy-3-o-tolylazetidin-1-yl)ethyl]-3-(1H-imidazol-4-yl)propionamide N—[(R)-1-(4-methoxybenzyl)-2-oxo-2-(3-propoxy-3-o-tolylazetidin-1-yl)ethyl]-3-(1H-imidazol-4-yl)propionamide N—[(R)-2-[3-butoxy-3-(4-fluorophenyl)azetidin-1-yl]-1-(4-methoxybenzyl)-2-oxoethyl]-3-(1H-imidazol-4-yl)propionamide N—[(R)-1-(4-methoxybenzyl)-2-oxo-2-(3-pentyloxy-3-o-tolylazetidin-1-yl)ethyl]-3-(1H-imidazol-4-yl)propionamide N—[(R)-2-(3-hexyloxy-3-o-tolylazetidin-1-yl)-1-(4-methoxybenzyl)-2-oxoethyl]-3-(1H-imidazol-4-yl)propionamide N—[(R)-1-(4-methoxybenzyl)-2-oxo-2-(3-pentyl-3-phenylazetidin-1-yl)ethyl]-3-(1H-imidazol-4-yl)propionamide N—[(R)-2-(3-butyl-3-phenylazetidin-1-yl)-1-(4-methoxybenzyl)-2-oxoethyl]-3-(1H-imidazol-4-yl)propionamide N—[(R)-2-(3-cyclopropylmethoxy-3-phenylazetidin-1-yl)-1-(4-methoxybenzyl)-2-oxoethyl]-3-(1H-imidazol-4-yl)propionamide N—[(R)-2-(3-hydroxy-3-o-tolylazetidin-1-yl)-1-(4-methoxybenzyl)-2-oxoethyl]-3-(1H-imidazol-4-yl)propionamide N—[(R)-2-[3-butoxy-3-(4-fluorophenyl)azetidin-1-yl]-1-(3-fluorobenzyl)-2-oxoethyl]-3-(1H-imidazol-4-yl)propionamide N—[(R)-2-[3-butoxy-3-(4-fluorophenyl)azetidin-1-yl]-1-(4-fluorobenzyl)-2-oxoethyl]-3-(1H-imidazol-4-yl)propionamide N—[(R)-2-(3-butoxy-3-phenylazetidin-1-yl)-1-(4-fluorobenzyl)-2-oxoethyl]-3-(1H-imidazol-4-yl)propionamide N—{(R)-1-benzyl-2-[3-butoxy-3-(4-fluoro-phenyl)azetidin-1-yl]-2-oxoethyl}-3-(4H-imidazol-2-yl)propionamide N—[(R)-1-benzyl-2-(3-butoxy-3-phenylazetidin-1-yl)-2-oxoethyl]-3-(1H-imidazol-4-yl)propionamide N—[(R)-2-(3-butoxy-3-phenylazetidin-1-yl)-1-(4-methoxybenzyl)-2-oxoethyl]-3-(1H-imidazol-4-yl)propionamide N—[(R)-1-(4-methoxybenzyl)-2-oxo-2-(3-pentyl-3-o-tolylazetidin-1-yl)ethyl]-3-(1H-imidazol-4-yl)propionamide N—[(R)-2-[3-(4-fluorophenyl)-3-pentylazetidin-1-yl]-1-(4-methoxybenzyl)-2-oxoethyl]-3-(1H-imidazol-4-yl)propionamide N—[(R)-2-(3-butoxy-3-o-tolylazetidin-1-yl)-1-(4-methoxybenzyl)-2-oxoethyl]-3-(1H[1,2,3]triazol-4-yl)propionamide N—[(R)-2-(3-butoxy-3-o-tolylazetidin-1-yl)-1-(4-methoxybenzyl)-2-oxoethyl]-3-(5-methyl-3H-[1,2,4]triazol-3-yl)propionamide N—[(R)-2-(3-butoxy-3-o-tolylazetidin-1-yl)-1-(4-methoxybenzyl)-2-oxoethyl]-3-(5-methyl-3H-imidazol-4-yl)propionamide N—{(R)-1-(4-methoxybenzyl)-2-[3-(2-methoxyphenyl)-3-pentylazetidin-1-yl]-2-oxoethyl}-3-(1H-imidazol-4-yl)propionamide N—[(R)-2-[3-(2-fluorophenyl)-3-pentylazetidin-1-yl]-1-(4-methoxybenzyl)-2-oxoethyl]-3-(1H-imidazol-4-yl)propionamide
N—[(R)-2-[3-(2-chlorophenyl)-3-pentylazetidin-1-yl]-1-(4-methoxybenzyl)-2-oxoethyl]-3-(1H-imidazol-4-yl)propionamide
N—[(R)-1-(4-chlorobenzyl)-2-oxo-2-(3-pentyl-3-phenylazetidin-1-yl)ethyl]-3-(1H-imidazol-4-yl)propionamide
N—[(R)-1-(4-fluorobenzyl)-2-oxo-2-(3-pentyl-3-phenylazetidin-1-yl)ethyl]-3-(1H-imidazol-4-yl)propionamide
N—[(R)-1-benzyl-2-oxo-2-(3-pentyl-3-phenylazetidin-1-yl)ethyl]-3-(1H-imidazol-4-yl)propionamide
N—[(R)-2-(3-butoxy-3-o-tolylazetidin-1-yl)-1-(4-methoxybenzyl)-2-oxoethyl]-3-(1H-imidazol-4-yl)acrylamide
N—[(R)-2-[3-(2,4-difluorophenyl)-3-pentylazetidin-1-yl]-1-(4-methoxybenzyl)-2-oxoethyl]-3-(1H-imidazol-4-yl)propionamide
N—[(R)-2-oxo-2-(3-pentyl-3-phenylazetidin-1-yl)-1-(3-trifluoromethylbenzyl)ethyl]-3-(1H-imidazol-4-yl)propionamide
N—[(R)-2-oxo-2-(3-pentyl-3-phenylazetidin-1-yl)-1-(4-trifluoromethylbenzyl)ethyl]-3-(1H-imidazol-4-yl)propionamide
N—[(R)-1-(3,4-dichlorobenzyl)-2-oxo-2-(3-pentyl-3-phenylazetidin-1-yl)ethyl]-3-(1H-imidazol-4-yl)propionamide
N—[(R)-1-(3,4-difluorobenzyl)-2-oxo-2-(3-pentyl-3-phenylazetidin-1-yl)ethyl]-3-(1H-imidazol-4-yl)propionamide
N—[(R)-2-[3-(3,4-dichlorophenyl)-3-pentylazetidin-1-yl]-1-(4-methoxybenzyl)-2-oxoethyl]-3-(1H-imidazol-4-yl)propionamide
N—[(R)-2-[3-(3-fluorophenyl)-3-pentylazetidin-1-yl]-1-(4-methoxybenzyl)-2-oxoethyl]-3-(1H-imidazol-4-yl)propionamide
N—[(R)-1-(3-fluorobenzyl)-2-oxo-2-(3-pentyl-3-phenylazetidin-1-yl)ethyl]-3-(1H-imidazol-4-yl)propionamide
N—[(R)-1-(2-fluorobenzyl)-2-oxo-2-(3-pentyl-3-phenylazetidin-1-yl)ethyl]-3-(1H-imidazol-4-yl)propionamide
N—[(R)-1-(2,4-dichlorobenzyl)-2-oxo-2-(3-pentyl-3-phenylazetidin-1-yl)ethyl]-3-(1H-imidazol-4-yl)propionamide
N—[(R)-2-[3-(4-chlorophenyl)-3-pentylazetidin-1-yl]-1-(4-methoxybenzyl)-2-oxoethyl]-3-(1H-imidazol-4-yl)propionamide
N—[(R)-2-[3-(2,5-difluorophenyl)-3-pentylazetidin-1-yl]-1-(4-methoxybenzyl)-2-oxoethyl]-3-(1H-imidazol-4-yl)propionamide
N—[(R)-2-[3-(2,6-difluorophenyl)-3-pentylazetidin-1-yl]-1-(4-methoxybenzyl)-2-oxoethyl]-3-(1H-imidazol-4-yl)propionamide
N-[2-(3-butoxy-3-o-tolylazetidin-1-yl)-1-(4-methoxybenzyl)-2-oxoethyl]-3-(1H-imidazol-4-yl)hexyramide
N-[2-(3-butoxy-3-o-tolylazetidin-1-yl)-1-(4-methoxybenzyl)-2-oxoethyl]-3-(1H-imidazol-4-yl)pentyramide
N—[(R)-1-(4-methoxybenzyl)-2-oxo-2-(3-pentyl-3-phenylazetidin-1-yl)ethyl]-3-(3-methyl-3H-imidazol-4-yl)propionamide
N-[2-(3-butoxy-3-o-tolylazetidin-1-yl)-1-(2,4-dichlorobenzyl)-2-oxoethyl]-3-(1H-imidazol-4-yl)hexyramide
N—[(R)-2-(3-cyclohexyl-3-pentylazetidin-1-yl)-1-(4-methoxybenzyl)-2-oxoethyl]-3-(1H-imidazol-4-yl)propionamide
N—[(R)-2-(3-butoxy-3-o-tolylazetidin-1-yl)-1-(4-methoxybenzyl)-2-oxoethyl]-3-(3-methyl-3H-imidazol-4-yl)propionamide
N—[(R)-2-[3-butoxy-3-(2-fluorophenyl)azetidin-1-yl]-1-(4-methoxybenzyl)-2-oxoethyl]-3-(1H-imidazol-4-yl)-propionamide
N—[(R)-2-(3-butoxy-3-o-tolylazetidin-1-yl)-1-(4-methoxybenzyl)-2-oxoethyl]-3-(1-methyl-1H-imidazol-4-yl)propionamide
N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate
(S)—N—[(R)-2-(3-butoxy-3-o-tolylazetidin-1-yl)-1-(4-methoxybenzyl)-2-oxoethyl]-2-hydroxy-3-(1H-imidazol-4-yl)propionamide
N-[2-(3-butoxy-3-o-tolylazetidin-1-yl)-1-(4-hydroxybenzyl)-2-oxoethyl]-3-(3H-imidazol-4-yl)propionamide
N-[1-(3-butoxy-3-o-tolylazetidine-1-carbonyl)-2-hydroxy-2-(4-methoxyphenyl)ethyl]-3-(1H-imidazol-4-yl)propionamide
N—[(R)-2-(3-butoxy-3-o-tolylazetidin-1-yl)-1-(4-methoxybenzyl)-2-oxoethyl]-3-hydroxy-3-(1H-imidazol-4-yl)propionamide
N—[(R)-2-(3-but-2-ynyloxy-3-o-tolylazetidin-1-yl)-1-(4-methoxybenzyl)-2-oxoethyl]-3-(1H-imidazol-4-yl)propionamide
N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide
N—[(R)-2-(3-cyclohexylmethoxy-3o-tolylazetidin-1-yl)-1-(4-methoxybenzyl)-2-oxoethyl]-3-(1H-imidazol-4-yl)propionamide
3-(1H-imidazol-4-yl)-N—{(R)-1-(4-methoxybenzyl)-2-oxo-2-[3-o-tolyl-3-(4,4,4-trifluorobutoxyl)azetidin-1-yl]ethylpropionamide
N—[(R)-2-(3-cyclobutylmethoxy-3-o-tolylazetidin-1-yl)-1-(4-methoxybenzyl)-2-oxoethyl]-3-(5-methyl-1H-imidazol-4-yl)propionamide
N—{(R)-1-(4-methoxybenzyl)-2-[3-(3-methylbut-2-enyloxy)-3-o-tolylazetidin-1-yl]-2-oxoethyl}-3-(5-methyl-1H-imidazol-4-ylpropionamide
3-(1H-imidazol-4-yl)-N—[(R)-1-(4-methoxybenzyl)-2-oxo-2-(3-phenylazetidin-1-yl)ethyl]propionamide
N—[(R)-2-[3-(4-fluorophenyl)azetidin-1-yl]-1-(4-methoxybenzyl)-2-oxoethyl]-3-(1H-imidazol-4-yl)propionamide
3-(1H-imidazol-4-yl)-N—{(R)-1-(4-methoxybenzyl)-2-[3-(2-methoxyphenyl)azetidin-1-yl]-2-oxoethyl}propionamide
N—[(R)-2-[3-(2-fluorophenyl)azetidin-1-yl]-1-(4-methoxybenzyl)-2-oxoethyl]-3-(1H-imidazol-4-yl)propionamide
3-(1H-imidazol-4-yl)-N—{(R)-1-(4-methoxybenzyl)-2-oxo-2-[3-phenyl-3-(4,4,4-trifluorobutyl)azetidin-1-yl]ethyl}propionamide
N—[(R)-2-[3-(5-fluoropentyl)-3-phenylazetidin-1-yl]-1-(4-methoxybenzyl)-2-oxoethyl]-3-(1H-imidazol-4-yl)propionamide
N—[(R)-2-(3-cyclopropyl-3-phenylazetidin-1-yl)-1-(4-methoxybenzyl)-2-oxoethyl]-3-(1H-imidazol-4-yl)propionamide
N—[(R)-2-(3-cyclopropylmethyl-3-phenylazetidin-1-yl)-1-(4-methoxybenzyl)-2-oxoethyl]-3-(1H-imidazol-4-yl)propionamide
(S)-2-hydroxy-3-(1H-imidazol-4-yl)-N-[1-(4-methoxybenzyl)-2-oxo-2-(3-propoxy-3-o-tolylazetidin-1-yl)ethyl]propionamide (S)-2-amino-3-(1H-imidazol-4-yl)-N-[1-(4-methoxybenzyl)-2-oxo-2-(3-propoxy-3-o-tolylazetidin-1-yl)ethyl]propionamide N-[2-(3-butoxy-3-o-tolylazetidin-1-yl)-1-(4-methoxybenzyl)-2-oxoethyl]-3-(1H-imidazol-4-yl)butyramide (S)—N-[2-(3-butoxy-3-phenylazetidin-1-yl)-1-(4-methoxybenzyl)-2-oxoethyl]-3-(1H-imidazol-4-yl)-2-methanesulphonylaminopropionamide N—[(R)-1-(4-methoxybenzyl)-2-oxo-2-(3-pentyl-3-phenylazetidin-1-yl)ethyl]-3-(1-methyl-1H-imidazol-4-yl)propionamide and also the respective salts and enantiomers thereof.

The compounds of general formula (I) are prepared according to reaction scheme 1 presented below.

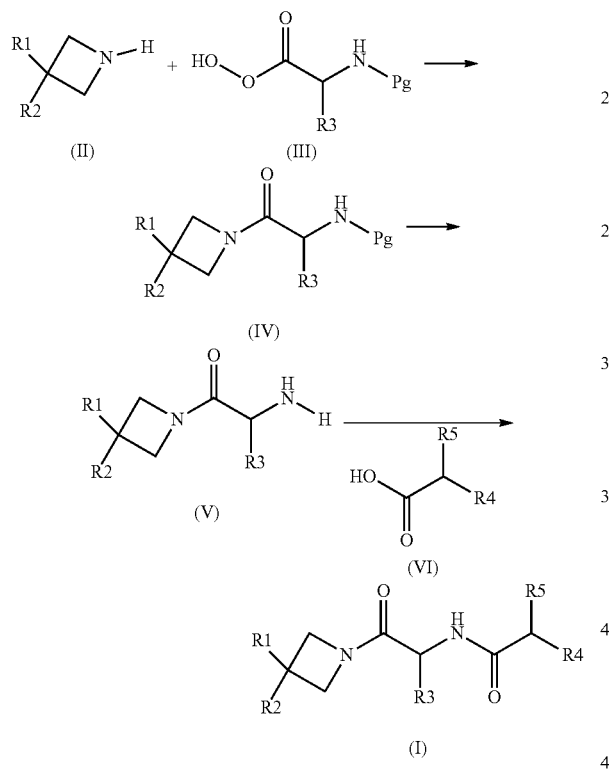

According to Scheme 1, the compounds of general formula (IV) can be prepared by coupling between the intermediates of formula (II) and an amino acid of formula (III), the amine function of which is protected with a protective group Pg (for example, a Boc, CBz or Fmoc group), under conventional peptide coupling conditions, using for example, as coupling agent, 1-(3-dimethylaminopropyl)-3-ethylcarbodiimide hydrochloride or hydroxybenzotriazole or TBTU, and as base, triethylamine or diisopropylethylamine in a solvent such as dichloromethane or dimethylformamide.

The amino acids of general formula (IV) are commercially available or are prepared by methods described in the literature (Williams, R. M., Synthesis of optically active α-amino acids, Pergamon Press, Oxford, 1989).

The compounds of general formula (V) are obtained by deprotection of the amine function of the compounds of general formula (IV), by methods chosen from those known to those skilled in the art. They comprise, inter alia, the use of trifluoroacetic acid or of hydrochloric acid in dichloromethane or ethyl acetate, for example, in the case of protection with a Boc group, hydrogenation with the appropriate metal in tetrahydrofuran or methanol, for example, in the case of protection with a CBz group, and piperidine in acetonitrile, for example, in the case of protection with an Fmoc group.

In a final stage, the compounds of general formula (I) are prepared by coupling between the amine of formula (V) and an acid of formula (VI) under conventional peptide coupling conditions, using for example, as coupling agent, 1-(3-dimethylaminopropyl)-3-ethylcarbodiimide hydrochloride or hydroxybenzotriazole or TBTU, and as base, triethylamine or diisopropylethylamine in a solvent such as dichloromethane or dimethylformamide.

The compounds of general formula (VI) are commercially available or are prepared according to the methods described in the literature or known to those skilled in the art, adapted according to the nature of the substituents R4 and R5. Depending on the nature of R4 and R5, Schemes 2, 3 and 4 hereinafter present examples of preparation of the compounds of general formula (VI).

For example, when R5 contains an alkyl substituted with a 1,2,3-triazole heterocycle, the compound (VI) can be prepared according to Scheme 2:

Scheme 2:

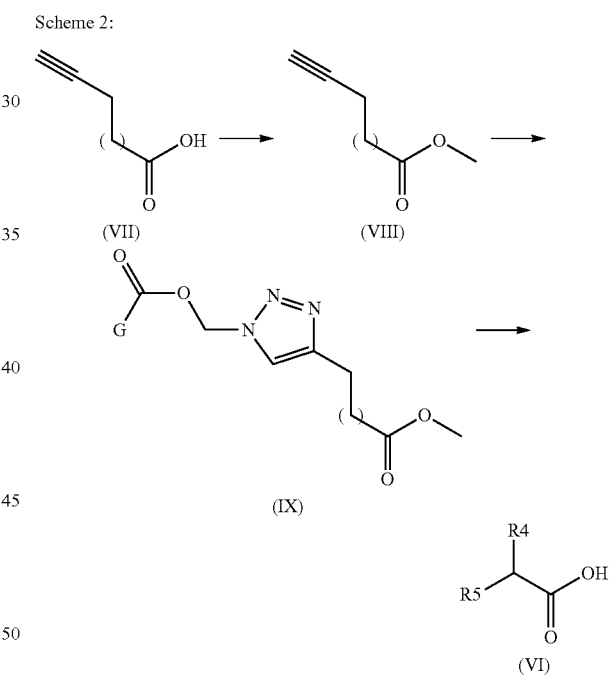

The compounds of general formula (VIII) are obtained by esterification of the acid function of the compounds of general formula (VII), by methods chosen from those known to those skilled in the art. They comprise, inter alia, the use of sulphuric acid in methanol, for example. The compounds of formula (IX) obtained from the compounds of formula (VIII) are prepared by methods described in the literature (Loren J. C., Synlett, 2005, 2847-2850) followed by cleavage in a basic medium in the presence, for example, of sodium hydroxide in a water/methanol mixture, so as to generate the triazole compounds (VI).

For example, when R5 contains an alkyl substituted with an imidazole heterocycle, the compound (VI) is prepared according to Scheme 3:

Scheme 3:

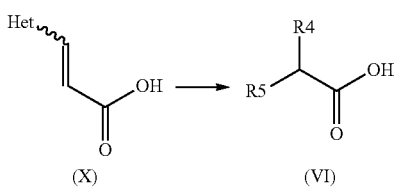

The compounds of general formula (X) are commercially available or are prepared according to the methods described in the literature or known to those skilled in the art. The compounds of general formula (VI) are obtained, for example, by hydrogenation of the compound (X) in the presence of a catalyst which may be palladium-on-charcoal in methanol.

For example, when R5 contains an alkyl substituted with a heterocycle, the compound (VI) can be prepared according to Scheme 4:

Scheme 4:

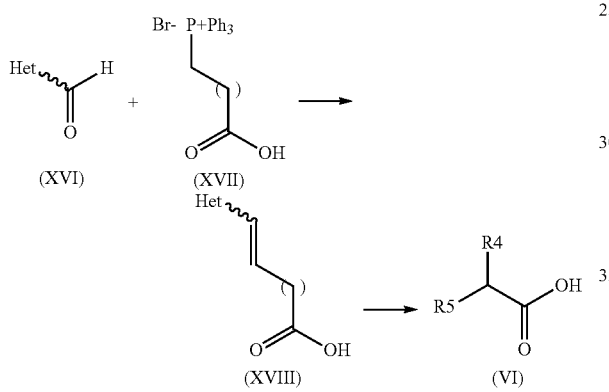

The compounds of general formula (XVIII) are obtained, for example, by Wittig reaction between an ylide (XVII) and a heterocycle substituted with an aldehyde (XVI) in the presence of a base, which may be lithium hexamethyl disilazane in a solvent such as tetrahydrofuran, for example. The compounds of general formula (VI) are obtained, for example, by hydrogenation of the compound (XVIII) in the presence of a catalyst which may be palladium-on-charcoal in an acidic medium, for example in acetic acid.

The compounds of general formula (II) are prepared according to the methods described in the literature or known to those skilled in the art, adapted according to the nature of the substituents R1 and R2. Schemes 5 and hereinafter present examples of preparation of the compounds of general formula (II).

For example, when R2 contains an alkoxy chain, the compound (II) can be prepared according to Scheme 5:

Scheme 5:

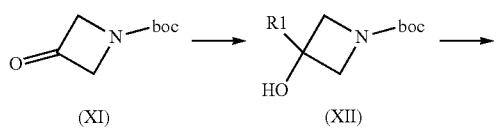

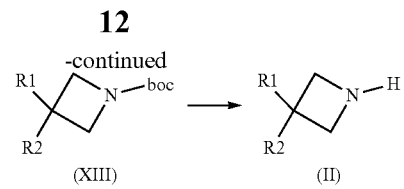

The compounds of general formula (XII) are obtained, for example, by addition of a magnesium halide derived from R1 to the N-boc-azetidinone (XI) (commercial) followed by alkylation of the tertiary alcohol in the presence of a base which may be sodium hydride, for example, and a halogenated derivative derived from R2, so as to give the compounds (XIII). The compounds of general formula (II) are obtained by deprotection of the amine function of the compounds of general formula (XIII), for example in the presence of trifluoroacetic acid or of hydrochloric acid in dichloromethane, or ethyl acetate.

For example, when R2 contains an alkyl chain, the compound of general formula (II) is prepared according to Scheme 6:

Scheme 6:

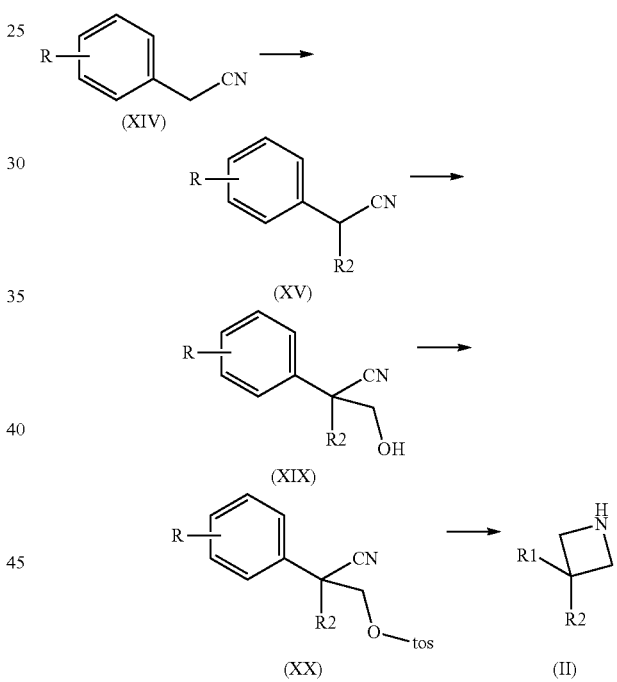

The compounds of general formula (XV) can be obtained, for example, by addition of a base such as sodium hydride in the presence of a halogenated derivative derived from R2. The primary alcohols of general formula (XIX) are synthesized from the nitrile derivatives (XV) in the presence of a base, for example sodium hydride and paraformaldehyde. The primary alcohol function of the compounds (XIX) is converted to a sulphonate in the presence of a base which may be triethylamine or tosyl chloride, for example. The azetidine compounds of general formula (II) are synthesized by intramolecular cyclization between an amine function obtained after reduction of the nitrile function, for example in the presence of lithium aluminium hydride, and the tosylate function of the compound of general formula (XX).

According to the present invention, the compounds of general formula (I) that are particularly preferred are those for which:

R1 represents an aryl, a substituted aryl or a cycloalkyl;
R2 represents a hydroxyl, a lower alkyl, a substituted lower alkyl, a higher alkyl, a substituted higher alkyl, a lower alkoxy, a substituted lower alkoxy, a higher alkoxy, a substituted higher alkoxy, or a cycloalkylalkoxy;
R3 represents an aralkyl or a substituted aralkyl;
R4 represents a heteroaralkyl or a substituted heteroaralkyl;
R5 represents a hydrogen or an acylamino; and also the corresponding salts and enantiomers of the compounds of general formula (I).

The preferred compounds are:

N—[(S)-1-[(S)-2-(3-butoxy-3-o-tolylazetidin-1-yl)-1-(4-methoxybenzyl)-2-oxoethylcarbamoyl]-2-(1H-imidazol-4-yl)ethyl]benzamide N—[(S)-1-[(S)-2-(3-butoxy-3-phenylazetidin-1-yl)-1-(4-methoxybenzyl)-2-oxoethylcarbamoyl]-2-(1H-imidazol-4-yl)ethyl]benzamide N—[(S)-1-[(S)-2-[3-butoxy-3-(4-fluorophenyl)azetidin-1-yl]-1-(4-methoxybenzyl)-2-oxoethylcarbamoyl]-2-(1H-imidazol-4-yl)ethyl]benzamide N—[(S)-1-[(S)-2-[3-butoxy-3-(3-fluorophenyl)azetidin-1-yl]-1-(4-methoxybenzyl)-2-oxoethylcarbamoyl]-2-(1H-imidazol-4-yl)ethyl]benzamide N—[(R)-2-(3-butoxy-3-o-tolylazetidin-1-yl)-1-(4-methoxybenzyl)-2-oxoethyl]-3-(1H-imidazol-4-yl)propionamide N—[(R)-2-(3-ethoxy-3-o-tolylazetidin-1-yl)-1-(4-methoxybenzyl)-2-oxoethyl]-3-(1H-imidazol-4-yl)propionamide N—[(R)-2-(3-butoxy-3-phenylazetidin-1-yl)-1-(2,4-dichlorobenzyl)-2-oxoethyl]-3-(1H-imidazol-4-yl)propionamide N—[(R)-2-(3-cyclopropylmethoxy-3-o-tolylazetidin-1-yl)-1-(4-methoxybenzyl)-2-oxoethyl]-3-(1H-imidazol-4-yl)propionamide N—[(R)-1-(4-methoxybenzyl)-2-oxo-2-(3-propoxy-3-o-tolylazetidin-1-yl)ethyl]-3-(1H-imidazol-4-yl)propionamide N—[(R)-2-[3-butoxy-3-(4-fluorophenyl)azetidin-1-yl]-1-(4-methoxybenzyl)-2-oxoethyl]-3-(1H-imidazol-4-yl)propionamide N—[(R)-1-(4-methoxybenzyl)-2-oxo-2-(3-pentyloxy-3-o-tolylazetidin-1-yl)ethyl]-3-(1H-imidazol-4-yl)propionamide N—[(R)-1-(4-methoxybenzyl)-2-oxo-2-(3-pentyl-3-phenylazetidin-1-yl)ethyl]-3-(1H-imidazol-4-yl)propionamide N—[(R)-2-(3-butyl-3-phenylazetidin-1-yl)-1-(4-methoxybenzyl)-2-oxoethyl]-3-(1H-imidazol-4-yl)propionamide N—[(R)-2-[3-butoxy-3-(4-fluorophenyl)azetidin-1-yl]-1-(3-fluorobenzyl)-2-oxoethyl]-3-(1H-imidazol-4-yl)propionamide N—[(R)-2-(3-butoxy-3-phenylazetidin-1-yl)-1-(4-fluorobenzyl)-2-oxoethyl]-3-(1H-imidazol-4-yl)propionamide N—[(R)-1-benzyl-2-(3-butoxy-3-phenylazetidin-1-yl)-2-oxoethyl]-3-(1H-imidazol-4-yl)propionamide N—[(R)-1-(4-methoxybenzyl)-2-oxo-2-(3-pentyl-3-o-tolylazetidin-1-yl)ethyl]-3-(1H-imidazol-4-yl)propionamide N—[(R)-2-[3-(4-fluorophenyl)-3-pentylazetidin-1-yl]-1-(4-methoxybenzyl)-2-oxoethyl]-3-(1H-imidazol-4-yl)propionamide N—[(R)-2-(3-butoxy-3-o-tolylazetidin-1-yl)-1-(4-methoxybenzyl)-2-oxoethyl]-3-(5-methyl-3H-[1,2,4]triazol-3-yl)propionamide N—[(R)-2-(3-butoxy-3-o-tolylazetidin-1-yl)-1-(4-methoxybenzyl)-2-oxoethyl]-3-(5-methyl-3H-imidazol-4-yl)propionamide N—{(R)-1-(4-methoxybenzyl)-2-[3-(2-methoxyphenyl)-3-pentylazetidin-1-yl]-2-oxoethyl}-3-(1H-imidazol-4-yl)propionamide N—[(R)-2-[3-(2-fluorophenyl)-3-pentylazetidin-1-yl]-1-(4-methoxybenzyl)-2-oxoethyl]-3-(1H-imidazol-4-yl)propionamide N—[(R)-2-[3-(2-chlorophenyl)-3-pentylazetidin-1-yl]-1-(4-methoxybenzyl)-2-oxoethyl]-3-(1H-imidazol-4-yl)propionamide N—[(R)-1-benzyl-2-oxo-2-(3-pentyl-3-phenylazetidin-1-yl)ethyl]-3-(1H-imidazol-4-yl)propionamide N—[(R)-2-[3-(2,4-difluorophenyl)-3-pentylazetidin-1-yl]-1-(4-methoxybenzyl)-2-oxoethyl]-3-(1H-imidazol-4-yl)propionamide N—[(R)-2-[3-(3,4-dichlorophenyl)-3-pentylazetidin-1-yl]-1-(4-methoxybenzyl)-2-oxoethyl]-3-(1H-imidazol-4-yl)propionamide N—[(R)-2-[3-(3,4-dichlorophenyl)-3-pentylazetidin-1-yl]-1-(4-methoxybenzyl)-2-oxoethyl]-3-(1H-imidazol-4-yl)propionamide N—[(R)-2-[3-(3-fluorophenyl)-3-pentylazetidin-1-yl]-1-(4-methoxybenzyl)-2-oxoethyl]-3-(1H-imidazol-4-yl)propionamide N—[(R)-1-(2,4-dichlorobenzyl)-2-oxo-2-(3-pentyl-3-phenylazetidin-1-yl)ethyl]-3-(1H-imidazol-4-yl)propionamide N—[(R)-2-[3-(2,5-difluorophenyl)-3-pentylazetidin-1-yl]-1-(4-methoxybenzyl)-2-oxoethyl]-3-(1H-imidazol-4-yl)propionamide N—[(R)-2-[3-(2,6-difluorophenyl)-3-pentylazetidin-1-yl]-1-(4-methoxybenzyl)-2-oxoethyl]-3-(1H-imidazol-4-yl)propionamide N-[2-(3-butoxy-3-o-tolylazetidin-1-yl)-1-(4-methoxybenzyl)-2-oxoethyl]-3-(1H-imidazol-4-yl)hexyramide N-[2-(3-butoxy-3-o-tolylazetidin-1-yl)-1-(4-methoxybenzyl)-2-oxoethyl]-3-(1H-imidazol-4-yl)pentyramide N—[(R)-1-(4-methoxybenzyl)-2-oxo-2-(3-pentyl-3-phenylazetidin-1-yl)ethyl]-3-(3-methyl-3H-imidazol-4-yl)propionamide N—[(R)-2-(3-cyclohexyl-3-pentylazetidin-1-yl)-1-(4-methoxybenzyl)-2-oxoethyl]-3-(1H-imidazol-4-yl)propionamide N—[(R)-2-(3-butoxy-3-o-tolylazetidin-1-yl)-1-(4-methoxybenzyl)-2-oxoethyl]-3-(3-methyl-3H-imidazol-4-yl)propionamide N—[(R)-2-[3-butoxy-3-(2-fluorophenyl)azetidin-1-yl]-1-(4-methoxybenzyl)-2-oxoethyl]-3-(1H-imidazol-4-yl)propionamide N—[(R)-2-(3-butoxy-3-o-tolylazetidin-1-yl)-1-(4-methoxybenzyl)-2-oxoethyl]-3-(1-methyl-1H-imidazol-4-yl)propionamide N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate (S)—N—[(R)-2-(3-butoxy-3-o-tolylazetidin-1-yl)-1-(4-methoxybenzyl)-2-oxoethyl]-2-hydroxy-3-(1H-imidazol-4-yl)propionamide N-[2-(3-butoxy-3-o-tolylazetidin-1-yl)-1-(4-hydroxybenzyl)-2-oxoethyl]-3-(3H-imidazol-4-yl)propionamide N—[(R)-2-(3-butoxy-3-o-tolylazetidin-1-yl)-1-(4-methoxybenzyl)-2-oxoethyl]-3-hydroxy-3-(1H-imidazol-4-yl)propionamide N—[(R)-2-(3-but-2-ynyloxy-3-o-tolylazetidin-1-yl)-1-(4-methoxybenzyl)-2-oxoethyl]-3-(1H-imidazol-4-yl)propionamide N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide N—[(R)-2-(3-cyclohexylmethoxy-3-o-tolylazetidin-1-yl)-1-(4-methoxybenzyl)-2-oxoethyl]-3-(1H-imidazol-4-yl)propionamide 3-(1H-imidazol-4-yl)-N—{(R)-1-(4-methoxybenzyl)-2-oxo-2-[3-o-tolyl-3-(4,4,4-trifluorobutoxyl)azetidin-1-yl]ethylpropionamide N—[(R)-2-(3-cyclobutylmethoxy-3-o-tolylazetidin-1-yl)-1-(4-methoxybenzyl)-2-oxoethyl]-3-(5-methyl-1H-imidazol-4-yl)propionamide N—{(R)-1-(4-methoxybenzyl)-2-[3-(3-methylbut-2-enyloxy)-3-o-tolylazetidin-1-yl]-2-oxoethyl}-3-(5-methyl-1H-imidazol-4-ylpropionamide and also the respective salts and enantiomers thereof.

According to the present invention, the compounds of general formula (I) that are particularly preferred are those for which:

R1 represents an aryl radical, a substituted aryl radical or a cycloalkyl radical;

R2 represents a lower alkoxy radical, a higher alkoxy radical, a cycloalkylalkoxy radical, a lower alkyl radical or a higher alkyl radical;

R3 represents a substituted aralkyl radical;

R4 represents a substituted imidazole or an unsubstituted imidazole;

R5 represents hydrogen; and also the corresponding salts and enantiomers of the compounds of general formula (I).

N—[(R)-2-(3-butoxy-3-o-tolylazetidin-1-yl)-1-(4-methoxybenzyl)-2-oxoethyl]-3-(1H-imidazol-4-yl)propionamide N—[(R)-2-(3-ethoxy-3-o-tolylazetidin-1-yl)-1-(4-methoxybenzyl)-2-oxoethyl]-3-(1H-imidazol-4-yl)propionamide N—[(R)-2-(3-cyclopropylmethoxy-3-o-tolylazetidin-1-yl)-1-(4-methoxybenzyl)-2-oxoethyl]-3-(1H-imidazol-4-yl)propionamide N—[(R)-1-(4-methoxybenzyl)-2-oxo-2-(3-propoxy-3-o-tolylazetidin-1-yl)ethyl]-3-(1H-imidazol-4-yl)propionamide N—[(R)-2-[3-butoxy-3-(4-fluorophenyl)azetidin-1-yl]-1-(4-methoxybenzyl)-2-oxoethyl]-3-(1H-imidazol-4-yl)propionamide N—[(R)-1-(4-methoxybenzyl)-2-oxo-2-(3-pentyloxy-3-o-tolylazetidin-1-yl)ethyl]-3-(1H-imidazol-4-yl)propionamide N—[(R)-1-(4-methoxybenzyl)-2-oxo-2-(3-pentyl-3-phenylazetidin-1-yl)ethyl]-3-(1H-imidazol-4-yl)propionamide N—[(R)-2-(3-butyl-3-phenylazetidin-1-yl)-1-(4-methoxybenzyl)-2-oxoethyl]-3-(1H-imidazol-4-yl)propionamide N—[(R)-1-(4-methoxybenzyl)-2-oxo-2-(3-pentyl-3-o-tolylazetidin-1-yl)ethyl]-3-(1H-imidazol-4-yl)propionamide N—[(R)-2-[3-(4-fluorophenyl)-3-pentylazetidin-1-yl]-1-(4-methoxybenzyl)-2-oxoethyl]-3-(1H-imidazol-4-yl)propionamide N—[(R)-2-(3-butoxy-3-o-tolylazetidin-1-yl)-1-(4-methoxybenzyl)-2-oxoethyl]-3-(5-methyl-3H-imidazol-4-yl)propionamide N—{(R)-1-(4-methoxybenzyl)-2-[3-(2-methoxyphenyl)-3-pentylazetidin-1-yl]-2-oxoethyl}-3-(1H-imidazol-4-yl)propionamide N—[(R)-2-[3-(2-fluorophenyl)-3-pentylazetidin-1-yl]-1-(4-methoxybenzyl)-2-oxoethyl]-3-(1H-imidazol-4-yl)propionamide N—[(R)-2-[3-(2-chlorophenyl)-3-pentylazetidin-1-yl]-1-(4-methoxybenzyl)-2-oxoethyl]-3-(1H-imidazol-4-yl)propionamide N—[(R)-2-[3-(2,4-difluorophenyl)-3-pentylazetidin-1-yl]-1-(4-methoxybenzyl)-2-oxoethyl]-3-(1H-imidazol-4-yl)propionamide N—[(R)-2-[3-(3,4-dichlorophenyl)-3-pentylazetidin-1-yl]-1-(4-methoxybenzyl)-2-oxoethyl]-3-(1H-imidazol-4-yl)propionamide N—[(R)-2-[3-(3-fluorophenyl)-3-pentylazetidin-1-yl]-1-(4-methoxybenzyl)-2-oxoethyl]-3-(1H-imidazol-4-yl)propionamide N—[(R)-2-[3-(2,5-difluorophenyl)-3-pentylazetidin-1-yl]-1-(4-methoxybenzyl)-2-oxoethyl]-3-(1H-imidazol-4-yl)propionamide N—[(R)-2-[3-(2,6-difluorophenyl)-3-pentylazetidin-1-yl]-1-(4-methoxybenzyl)-2-oxoethyl]-3-(1H-imidazol-4-yl)propionamide N—[(R)-2-(3-cyclohexyl-3-pentylazetidin-1-yl)-1-(4-methoxybenzyl)-2-oxoethyl]-3-(1H-imidazol-4-yl)propionamide;

N—[(R)-2-[3-butoxy-3-(2-fluorophenyl)azetidin-1-yl]-1-(4-methoxybenzyl)-2-oxoethyl]-3-(1H-imidazol-4-yl)propionamide N—[(R)-2-(3-butoxy-3-o-tolylazetidin-1-yl)-1-(4-methoxybenzyl)-2-oxoethyl]-3-(1-methyl-1H-imidazol-4-yl)propionamide N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate N-[2-(3-butoxy-3-o-tolylazetidin-1-yl)-1-(4-hydroxybenzyl)-2-oxoethyl]-3-(3H-imidazol-4-yl)propionamide N-[1-(3-butoxy-3-o-tolylazetidine-1-carbonyl)-2-hydroxy-2-(4-methoxyphenyl)ethyl]-3-(1H-imidazol-4-yl)propionamide N—[(R)-2-(3-butoxy-3-o-tolylazetidin-1-yl)-1-(4-methoxybenzyl)-2-oxoethyl]-3-hydroxy-3-(1H-imidazol-4-yl)propionamide N—[(R)-2-(3-but-2-ynyloxy-3-o-tolylazetidin-1-yl)-1-(4-methoxybenzyl)-2-oxoethyl]-3-(1H-imidazol-4-yl)propionamide N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide N—[(R)-2-(3-cyclohexylmethoxy-3-o-tolylazetidin-1-yl)-1-(4-methoxybenzyl)-2-oxoethyl]-3-(1H-imidazol-4-yl)propionamide 3-(1H-imidazol-4-yl)-N—{(R)-1-(4-methoxybenzyl)-2-oxo-2-[3-o-tolyl-3-(4,4,4-trifluorobutoxyl)azetidin-1-yl]ethylpropionamide N—[(R)-2-(3-cyclobutylmethoxy-3-o-tolylazetidin-1-yl)-1-(4-methoxybenzyl)-2-oxoethyl]-3-(5-methyl-1H-imidazol-4-yl)propionamide N—{(R)-1-(4-methoxybenzyl)-2-[3-(3-methylbut-2-enyloxy)-3-o-tolylazetidin-1-yl]-2-oxoethyl}-3-(5-methyl-1H-imidazol-4-ylpropionamide and also the respective salts and enantiomers thereof.

The compounds according to the invention have melanocortin-receptor-modulating properties. The term "melanocortin-receptor-modulating property" is intended to mean melanocortin receptor agonist or antagonist properties. This activity on MCRs is measured in a transactivation test and quantified by the 50% effective concentration (EC50), as described in Example 10.

Preferably, the compounds are compounds that at least modulate MCRs, selectively with respect to subtype 1 (MC1R), i.e. they exhibit a ratio of the EC50 MC1R relative to the other MCRs of greater than or equal to 10. Preferably, this ratio is greater than or equal to 10, advantageously greater than or equal to 20, and more advantageously greater than or equal to 50.

Advantageously, the compounds of the present invention exhibit a 50% effective concentration (EC50) value with respect to the MC1 receptor of less than or equal to 10 µM, and more particularly less than or equal to 1 µM.

The invention is therefore directed towards the use of at least one compound of general formula (I) as defined above, for the preparation of a pharmaceutical or cosmetic composition in which said compound has a modulatory activity on one or more melanocortin receptors, and in particular on subtypes 1, 3, 4 and 5.

In one particular embodiment of the invention, the compounds of general formula (I) in the present invention have an MC1R-selective activity and are particularly useful in the treatment of pigmentary disorders, and of inflammatory and immune disorders. Some other compounds of the invention are MC4R-selective and are particularly useful in the treatment of eating and metabolism disorders and also neurodegenerative disorders.

The invention also relates to a therapeutic or cosmetic treatment method comprising the administration of a pharmaceutical or cosmetic composition comprising said compound, as a modulator of one or more melanocortin receptors, and in particular of subtypes 1, 3, 4 and 5. In one particular embodiment, the invention also relates to a therapeutic or cosmetic method comprising the administration of a pharmaceutical or cosmetic composition comprising said compound, for treating pigmentary disorders, and inflammatory and immune disorders. In one particular embodiment of the invention, the compounds are subtype-1-selective modulators.

The invention also relates to the use of a compound of general formula (I) as defined above, in the preparation of a medicament for use in the treatment of disorders associated with a dysfunction of MC1R.

Specifically, the compounds used according to the invention are particularly suitable for the treatment and/or prevention of the disorders and/or diseases chosen from:

inflammatory diseases of the digestive tract, including in particular the intestines (and particularly the colon in the case of irritable bowel syndrome, ulcerative colitis or Crohn's disease); pancreatitis, hepatitis (acute and chronic), inflammatory pathological conditions of the bladder and gastritis;

inflammatory diseases of the locomotor system, including rheumatoid arthritis, osteoarthritis, osteoporosis, traumatic arthritis, post-infectious arthritis, muscle degeneration, dermatomyositis;

inflammatory diseases of the urogenital system, and in particular glomerulonephritis;

inflammatory diseases of the cardiac system, and in particular pericarditis and myocarditis, and diseases including those for which inflammation is an underlying element. These diseases include, but are not limited to, atherosclerosis, transplant atherosclerosis, peripheral vascular diseases, inflammatory vascular diseases, intermittent claudication or limping, restenosis, stroke, transient ischaemic attack, myocardial ischaemia and myocardial infarction. These compounds may also be used for treating hypertension, hyperlipidaemia, coronary artery diseases, unstable angina (or angina pectoris), thrombosis, platelet aggregation induced by thrombin and/or the consequences of thrombosis and/or of atheroma plaque formation;

inflammatory diseases of the respiratory and ENT system, including in particular asthma, acute respiratory distress syndrome, hayfever, allergic rhinitis, and chronic obstructive pulmonary disease. The compounds according to the invention may also be used for treating allergies;

inflammatory diseases of the central nervous system, and in particular Alzheimer's disease and any form of dementia, Parkinson's disease, Creutzfeldt-Jacob disease, multiple sclerosis, meningitis;

inflammatory skin diseases, and in particular urticaria, scleroderma, contact dermatitis, atopic dermatitis, psoriasis, ichthyosis, acne and other forms of folliculitis, rosacea and alopecia;

autoimmune diseases, and in particular lupus erythematosus, thyroid conditions, autoimmune diseases of the adrenal gland and autoimmune gastritis, vitiligo and alopecia areata;

inflammations accompanying bacterial, viral or fungal infections, in particular tuberculosis, septicaemia, fever, HIV whatever the location of the infection, herpes, cytomegalovirus, hepatitis A, B and C;

transplant or graft rejection, such as kidneys, liver, heart, lung, pancreas, bone marrow, cornea, intestines, skin (skin allograft, homograft and heterograft, etc.).

In addition, these compounds may be used for treating pain, whatever the origin thereof: post-operative pain, neuromuscular pain, headaches, cancer-related pain, dental pain, osteoarticular pain.

These compounds may be useful for modulating pigmentation, and as a result for:

treating diseases with pigmentation disorders, and in particular benign dermatoses such as vitiligo, albinism, melasma, lentigines, freckles, melanocytic naevi and all post-inflammatory pigmentations; and also pigmented tumours such as melanoma and local metastases (permeation nodules), regional metastases or systemic metastases thereof;

photoprotection against sunlight with the aim of preventing:

the harmful effects of sunlight such as actinic erythema, skin ageing, skin cancers (spinocellular, basocellular and melanoma), and in particular in diseases where it accelerates onset (xeroderma pigmentosum, basal cell naevus syndrome, familial melanoma);

photodermatoses due to exogenous photosensitizing agents, and in particular those caused by contact photosensitizing agents (for example, furocoumarins, halogenated salicylanilides and derivatives, and local sulphamides and derivatives) or those caused by photosensitizing agents via the systemic route (for example, psoralens, tetracyclines, sulphamides, phenothiazines, nalidixic acid, tricyclic antidepressants);

dermatosis attacks with photosensitivity, and in particular photoaggravated dermatoses (for example, lupus erythematosus, recurrent herpes, congenital poikilodermal or telangiectasic conditions with photosensitivity (Bloom syndrome, Cockayne syndrome, Rothmund-Thomson syndrome), actinic lichen planus, actinic granuloma, disseminated superficial actinic porokeratosis, acne rosacea, juvenile acne, bullous dermatoses, Darier's disease, cutaneous lymphoma, psoriasis, atopic dermatitis, contact eczema, follicular mucinosis, erythema multiforme, fixed drug erythema, lymphocytoma cutis, reticular erythema with mucinosis, melasma),
dermatoses with photosensitivity caused by deficiency of the protection system with melanin formation or distribution anomalies (for example, oculocutaneous albinism, phenylketonuria, anterior hypophyseal insufficiency, vitiligo, piebaldism) and with DNA repair system deficiency (for example, xeroderma pigmentosum, Cockayne syndrome),
dermatoses with photosensitivity caused by metabolic anomalies, such as cutaneous porphyrias (for example, late cutaneous porphyria, mixed porphyrias, erythropoietic protoporphyria, congenital erythropoietic porphyria (Gunther's disease), erythropoietic coproporphyria), pellagra or pellagroid erythemas (for example, pellagra, pellagroid erythemas and tryptophan metabolism disorders);
idiopathic photodermatosis attacks, and in particular PMLE (polymorphous light eruption), benign summer light eruption, actinic prurigo, persistent photosensitizations (actino-reticulosis, chronic actinic dermatosis, photosensitive eczema), solar urticaria, hydroa vacciniforme, juvenile spring eruption, solar pruritus),
modulating the colour of the skin or of the hair and of body hairs, and in particular by causing the skin to tan by increasing melanin synthesis or causing it to bleach by interfering with melanin synthesis, but also by preventing hair and body hair turning white or grey (for example canities and piebaldism);
modifying the colour of the hair and of body hairs in cosmetic indications.

These compounds may be useful for modulating sebaceous function for:
treating conditions with hyperseborrhoea, and in particular acne, seborrhoeic dermatitis, greasy skin and greasy hair, hyperseborrhoea in Parkinson's and epilepsy, and hyperandrogenism;
treating conditions with decreased sebaceous secretion, and in particular xerosis and all dry skin;
regulating benign or malignant sebocyte and sebaceous gland proliferation;
treating inflammatory conditions of the pilosebaceous follicle, and in particular acne, boils, carbuncles and folliculitis.

The invention also relates to the use of a compound of general formula (I) as defined above, for the preparation of a medicament for use in the treatment of disorders associated with an MC4R dysfunction.

The compounds of the invention may also be used for treating neurodegenerative disorders, including depression, anxiety, compulsive disorders such as obsessive-compulsive disorders, neuroses, psychoses, insomnia and sleep disorder, sleep apnoea, and drug abuse.

These compounds may be used for the treatment of male or female sexual dysfunctions. The male sexual dysfunctions include, but are not limited to, impotence, loss of libido, and erectile dysfunction.

The female sexual dysfunctions include, but are not limited to, sexual stimulation disorders or disorders related to desire, sexual receptivity, orgasm, and disturbances of the major points of sexual function. The female sexual dysfunctions may also include pain, preterm labour, dysmenorrhoea, excessive menstruation, and endometriosis.

The compounds according to the invention may also be used for treating disorders related to weight but not limited to obesity and anorexia (such as modification or impairment of appetite, spleen metabolism, innocent intake of fats or carbohydrates); diabetes mellitus (through glucose dose tolerance and/or decreased insulin resistance).

The compounds may also be used for treating cancer, and in particular lung cancer, prostate cancer, colon cancer, breast cancer, ovarian cancer and bone cancer, or angiogenesis disorders including the formation or growth of solid tumours.

A subject of the present invention is also a pharmaceutical composition for use in particular in the treatment of the abovementioned conditions, and which is characterized in that it comprises, in a pharmaceutically acceptable carrier compatible with the method of administration selected for said composition, a compound of general formula (I) or an enantiomer thereof or a salt thereof with a pharmaceutically acceptable acid.

The term "pharmaceutically acceptable carrier" is intended to mean a medium compatible with the skin, the mucous membranes and the skin appendages.

The administration of the composition according to the invention may be carried out orally, enterally, parenterally, topically or ocularly. Preferably, the pharmaceutical composition is conditioned in a form suitable for topical application.

When it is for oral administration, the composition may be in the form of tablets, gel capsules, dragees, syrups, suspensions, solutions, powders, granules, emulsions, suspensions of microspheres or nanospheres or lipid or polymeric vesicles for controlled release. When it is for parenteral administration, the composition may be in the form of solutions or suspensions for infusion or for injection.

The compounds according to the invention are generally administered orally or systemically at a daily dose of approximately 0.01 mg/kg to 100 mg/kg of body weight, in 1 or more intakes.

The compounds are used systemically at a concentration generally between 0.001% and 10% by weight, preferably between 0.01% and 1% by weight, relative to the total weight of the composition.

When administered topically, the pharmaceutical composition according to the invention is more particularly for use in the treatment of the skin and the mucous membranes, and may be in liquid, pasty or solid form, and more particularly in the form of salves, creams, milks, ointments, powders, impregnated pads, syndets, solutions, gels, sprays, foams, suspensions, sticks, shampoos or washing bases. It may also be in the form of suspensions of microspheres or nanospheres or lipid or polymeric vesicles or polymeric or gelled patches for controlled release.

The compositions used for topical application have a concentration of compound according to the invention of generally between 0.001% and 10% by weight, preferably between 0.01% and 5% by weight, relative to the total weight of the composition.

The compounds of general formula (I) according to the invention also find use in the cosmetics field, in particular in protection against the harmful aspects of sunlight, for preventing and/or combating photoinduced or chronological ageing of the skin and the skin appendages.

A subject of the invention is therefore also a composition comprising, in a cosmetically acceptable carrier, at least one of the compounds of general formula (I). The term "cosmetically acceptable medium" is intended to mean a medium compatible with the skin, the mucous membranes and the skin appendages.

A subject of the invention is also the cosmetic use of a composition comprising at least one compound of general formula (I), for preventing and/or treating the signs of ageing and/or the skin.

A subject of the invention is also the cosmetic use of a composition comprising at least one compound of general formula (I) for body or hair hygiene.

The cosmetic composition according to the invention containing, in a cosmetically acceptable carrier, a compound of general formula (I), or an enantiomer thereof or a salt thereof with a pharmaceutically acceptable acid, may be in particular in the form of a cream, a milk, a gel, suspensions of microspheres or nanospheres or lipid or polymeric vesicles, impregnated pads, solutions, sprays, foams, sticks, soaps, washing bases or shampoos.

The concentration of compound of general formula (I) in the cosmetic composition is preferably between 0.001% and 10% by weight, relative to the total weight of the composition.

The pharmaceutical and cosmetic compositions as described above may also contain inert additives, or even pharmacodynamically active additives as regards the pharmaceutical compositions, or combinations of these additives, and in particular:

wetting agents;
flavour enhancers;
preservatives such as para-hydroxybenzoic acid esters;
stabilizers;
moisture regulators;
pH regulators;
osmotic pressure modifiers;
emulsifiers;
UV-A and UV-B screening agents;
antioxidants, such as α-tocopherol, butylhydroxyanisole or butylhydroxytoluene, superoxide dismutase, ubiquinol;
emollients;
moisturizers, such as glycerol, PEG 400, thiamorpholinone and its derivatives or urea;
antiseborrhoeic or anti-acne agents, such as S-carboxymethylcysteine, S-benzylcysteamine, their salts or their derivatives, or benzoyl peroxide.

Of course, those skilled in the art will take care to select the optional compound(s) to be added to these compositions in such a way that the advantageous properties intrinsically associated with the present invention are not, or are not substantially, impaired by the envisaged addition.

Several examples of obtaining compounds of general formula (I) according to the invention and of the biological activity results for these compounds will now be given by way of illustration that is in no way limiting in nature.

The following examples describe the preparation of some compounds in accordance with the invention. These examples are not limiting and merely illustrate the present invention. The numbers of the compounds exemplified refer back to those given in Table I hereinafter, which illustrates the chemical names and the physical properties of some compounds according to the invention.

The following abbreviations are used:
TBTU: N,N,N',N'-tetramethyl-O-(benzotriazol-1-yl)uronium tetrafluoroborate
HOBt: 1-hydroxy-1,2,3-benzotriazole
EDC: 1-ethyl-(3-dimethylaminopropyl)carbodiimide, hydrochloride
BOC: tert-butoxycarbonyl
CBz: benzyloxycarbonyl
Fmoc: 6-fluorenylmethoxycarbonyl
Tos: p-toluenesulphonyl
DMF: dimethylformamide
DCM: dichloromethane
DIEA: diisopropylethylamine The term "conformers" is given to stereoisomers which convert from one to the other by rotation around bonds (single bond provided by a doublet of electrons).

Material & Methods

HPLC Methods:

Method A

| Column: | Gemini 150 × 3 mm, 3 μm |
|---|---|
| UV detector: | 220-420 nm |
| Flow rate: | 0.5 ml/min |
| Solvent A: | $CH_3CN$ + 0.05 TFA |
| Solvent B: | $H_2O$ + 0.05 TFA |

| Gradient: | |
|---|---|
| Time | composition |
| 0.0 min | A = 5%, B = 95% |
| 5.0 min | A = 5%, B = 95% |
| 20.0 min | A = 95%, B = 5% |
| 30.0 min | A = 95%, B = 5% |

Method B

| Column: | Gemini 150 × 3 mm, 3 μm |
|---|---|
| UV detector: | 220-420 nm |
| Flow rate: | 0.5 ml/min |
| Solvent A: | $CH_3CN$ + 0.05 TFA |
| Solvent B: | $H_2O$ + 0.05 TFA |

| Gradient: | |
|---|---|
| Time | composition |
| 0.0 min | A = 5%, B = 95% |
| 20.0 min | A = 90%, B = 10% |
| 30.0 min | A = 90%, B = 10% |

Method C

| Column: | Atlantis C18 150 × 3.2 mm, 3 μm |
|---|---|
| UV detector: | 220-420 nm |
| Flow rate: | 0.3 ml/min |
| Solvent A: | $CH_3CN$ + 0.1 TFA |
| Solvent B: | $H_2O$ + 0.1 TFA |

| Gradient: | |
|---|---|
| Time | composition |
| 0.0 min | A = 5%, B = 95% |
| 5.0 min | A = 5%, B = 95% |
| 25.0 min | A = 95%, B = 5% |
| 30.0 min | A = 95%, B = 5% |

Method D

| Column: | Gemini 150 × 3 mm, 3 μm |
|---|---|
| UV detector: | 220-420 nm |
| Flow rate: | 0.5 ml/min |
| Solvent A: | $CH_3CN$ |
| Solvent B: | $H_2O$ + 0.02 TFA |

| Gradient: | |
|---|---|
| Time | composition |
| 0.0 min | A = 5%, B = 95% |
| 20.0 min | A = 90%, B = 10% |
| 30.0 min | A = 90%, B = 10% |

Method E

| | |
|---|---|
| Column: | Xbridge phenyl 150 × 2.1 mm, 3.5 μm |
| UV detector: | 220-420 nm |
| Flow rate: | 1.0 ml/min |
| Solvent A: | 95% MeOH/5% water + 25 mM NH$_4$OAc |
| Solvent B: | H$_2$O + 25 mM NH$_4$OAc |

Gradient:

| Time | composition |
|---|---|
| 0.0 min | A = 5%, B = 95% |
| 20.0 min | A = 98%, B = 2% |
| 30.0 min | A = 98%, B = 2% |

Method F

| | |
|---|---|
| Column: | Xbridge phenyl 250 × 4.6 mm, 5 μm |
| UV detector: | 220-420 nm |
| Flow rate: | 1.0 ml/min |
| Solvent A: | 90% MeOH/10% water + 25 mM NH$_4$OAc |
| Solvent B: | H$_2$O + 25 mM NH$_4$OAc |

Gradient:

| Time | composition |
|---|---|
| 0.0 min | A = 5%, B = 95% |
| 20.0 min | A = 98%, B = 2% |
| 30.0 min | A = 98%, B = 2% |

Method G

| | |
|---|---|
| Column: | Xbridge phenyl 250 × 4.6 mm, 5 μm |
| UV detector: | 220-420 nm |
| Flow rate: | 1.0 ml/min |
| Solvent A: | 90% MeOH/10% water + 25 mM NH$_4$OAc |
| Solvent B: | H$_2$O + 25 mM NH$_4$OAc |

Gradient:

| Time | composition |
|---|---|
| 0.0 min | A = 5%, B = 95% |
| 15.0 min | A = 98%, B = 2% |
| 30.0 min | A = 98%, B = 2% |

Method H

| | |
|---|---|
| Column: | Gemini C18 150 × 3 mm, 3 μm |
| UV detector: | 220-420 nm |
| Flow rate: | 0.3 ml/min |
| Solvent A: | 94% MeOH/6% water + 10 mM NH$_4$OAc |
| Solvent B: | H$_2$O + 10 mM NH$_4$OAc |

Gradient:

| Time | composition |
|---|---|
| 0.0 min | A = 5%, B = 95% |
| 10.0 min | A = 95%, B = 5% |
| 30.0 min | A = 95%, B = 5% |

Method I

| | |
|---|---|
| Column: | Gemini C18 150 × 3 mm, 3 μm |
| UV detector: | 220-420 nm |
| Flow rate: | 0.3 ml/min |
| Solvent A: | H$_2$O + 0.05% TFA |
| Solvent B: | CH$_3$CN + 0.05% TFA |

Gradient:

| Time | composition |
|---|---|
| 0.0 min | A = 95%, B = 5.0% |
| 20.0 min | A = 5%, B = 95% |
| 30.0 min | A = 5%, B = 95% |

Method J

| | |
|---|---|
| Column: | Gemini C18 150 × 3 mm, 3 μm |
| UV detector: | 220-420 nm |
| Flow rate: | 0.5 ml/min |
| Solvent A: | MeOH + 0.1% TFA |
| Solvent B: | H$_2$O + 0.02% TFA |

Gradient:

| Time | composition |
|---|---|
| 0.0 min | A = 10%, B = 90% |
| 15.0 min | A = 95%, B = 5% |
| 30.0 min | A = 95%, B = 5% |

Method K

| | |
|---|---|
| Column: | Gemini C6-phenyl 150 × 3 mm, 3 μm |
| UV detector: | 220-420 nm |
| Flow rate: | 0.5 ml/min |
| Solvent A: | H$_2$O + 0.05% TFA |
| Solvent B: | CH$_3$CN + 0.05% TFA |

Gradient:

| Time | composition |
|---|---|
| 0.0 min | A = 95%, B = 5% |
| 20.0 min | A = 5%, B = 95% |
| 30.0 min | A = 5%, B = 95% |

Method L

| | |
|---|---|
| Column: | Gemini C18 150 × 3 mm, 3 μm |
| UV detector: | 220-420 nm |
| Flow rate: | 0.5 ml/min |
| Solvent A: | CH$_3$CN + 0.1% HCOOH |
| Solvent B: | H$_2$O + 0.1% HCOOH |

Gradient:

| Time | Composition |
|---|---|
| 0.0 min | A = 5%, B = 95.0% |
| 10.0 min | A = 5%, B = 95% |
| 30.0 min | A = 70%, B = 30% |

Method M

| | |
|---|---|
| Column: | ThermoHypersil Hypurity C18 150 × 4.6 mm, 5 μm |
| UV detector: | 220-420 nm |
| Flow rate: | 0.5 ml/min |
| Solvent A: | $H_2O$ + 0.05% TFA |
| Solvent B: | $CH_3CN$ + 0.05% TFA |

Gradient:

| Time | composition |
|---|---|
| 0.0 min | A = 95%, B = 5.0% |
| 20.0 min | A = 5%, B = 95% |
| 30.0 min | A = 5%, B = 95% |

Method N

| | |
|---|---|
| Column: | Atlantis T3 150 × 2.1 mm, 3 μm |
| UV detector: | 220-420 nm |
| Flow rate: | 0.3 ml/min |
| Solvent A: | $H_2O$ + 0.05% TFA |
| Solvent B: | $CH_3CN$ + 0.05% TFA |

Gradient:

| Time | composition |
|---|---|
| 0.0 min | A = 95%, B = 5.0% |
| 20.0 min | A = 5%, B = 95% |
| 30.0 min | A = 5%, B = 95% |

Method O

| | |
|---|---|
| Column: | Atlantis T3 150 × 4.6 mm, 5 μm |
| UV detector: | 220-420 nm |
| Flow rate: | 0.3 ml/min |
| Solvent A: | $H_2O$ + 0.05% TFA |
| Solvent B: | $CH_3CN$ + 0.05% TFA |

Gradient:

| Time | composition |
|---|---|
| 0.0 min | A = 95%, B = 5.0% |
| 20.0 min | A = 5%, B = 95% |
| 30.0 min | A = 5%, B = 95% |

Method P

| | |
|---|---|
| Column: | Atlantis T3 150 × 4.6 mm, 5 μm |
| UV detector: | 190-420 nm |
| Flow rate: | 0.25 ml/min |
| Solvent A: | $H_2O$ + 0.05% TFA |
| Solvent B: | $CH_3CN$ + 0.05% TFA |

Gradient:

| Time | composition |
|---|---|
| 0.0 min | A = 95%, B = 5.0% |
| 20.0 min | A = 5%, B = 95% |
| 30.0 min | A = 5%, B = 95% |

Method Q

| | |
|---|---|
| Column: | Atlantis T3 150 × 4.6 mm, 5 μm |
| UV detector: | 190-420 nm |
| Flow rate: | 0.3 ml/min |
| Solvent A: | $H_2O$ + 0.05% TFA |
| Solvent B: | $CH_3CN$ + 0.05% TFA |

Gradient:

| Time | composition |
|---|---|
| 0.0 min | A = 95%, B = 5.0% |
| 20.0 min | A = 5%, B = 95% |
| 30.0 min | A = 5%, B = 95% |

Method R

| | |
|---|---|
| Column: | Gemini C6-phenyl 150 × 3 mm, 3 μm |
| UV detector: | 190-420 nm |
| Flow rate: | 0.3 ml/min |
| Solvent A: | $CH_3CN$ + 0.05% TFA |
| Solvent B: | $H_2O$ + 0.05% TFA |

Gradient:

| Time | composition |
|---|---|
| 0.0 min | A = 10%, B = 90% |
| 15.0 min | A = 90%, B = 10% |
| 30.0 min | A = 90%, B = 10% |

Method S

| | |
|---|---|
| Column: | Eclipse XDB C8 150 × 4.6 mm, 5 μm |
| UV detector: | 190-420 nm |
| Flow rate: | 1 ml/min |
| Solvent A: | $CH_3CN$ + 0.1% HCOOH |
| Solvent B: | $H_2O$ + 0.1% HCOOH |

Gradient:

| Time | composition |
|---|---|
| 0.0 min | A = 10%, B = 90% |
| 20.0 min | A = 95%, B = 5% |
| 30.0 min | A = 95%, B = 5% |

Method T

| | |
|---|---|
| Column: | Gemini C6-phenyl 150 × 3 mm, 3 μm |
| UV detector: | 190-420 nm |
| Flow rate: | 0.3 ml/min |
| Solvent A: | $CH_3CN$ + 0.05% TFA |
| Solvent B: | $H_2O$ + 0.05% TFA |

Gradient:

| Time | composition |
|---|---|
| 0.0 min | A = 10%, B = 90% |
| 20.0 min | A = 90%, B = 10% |
| 30.0 min | A = 90%, B = 10% |

Method U

| Column: | Atlantis T3 150 × 4.6 mm, 5 μm |
|---|---|
| UV detector: | 190-420 nm |
| Flow rate: | 0.3 ml/min |
| Solvent A: | $CH_3CN$ + 0.05% TFA |
| Solvent B: | $H_2O$ + 0.05% TFA |

| Gradient: | |
|---|---|
| Time | composition |
| 0.0 min | A = 10%, B = 90% |
| 20.0 min | A = 90%, B = 10% |
| 30.0 min | A = 90%, B = 10% |

Method V

| Column: | Xbridge C18 250 × 4.5 mm, 5 μm |
|---|---|
| UV detector: | 190-420 nm |
| Flow rate: | 1 ml/min |
| Solvent A: | $CH_3CN$ + 0.05% TFA |
| Solvent B: | $H_2O$ + 0.05% TFA |

| Gradient: | |
|---|---|
| Time | composition |
| 0.0 min | A = 10%, B = 90% |
| 25.0 min | A = 90%, B = 10% |
| 30.0 min | A = 90%, B = 10% |

Method W

| Column: | Xbridge Phenyl 150 × 3 mm, 3 μm |
|---|---|
| UV detector: | 190-420 nm |
| Flow rate: | 1 ml/min |
| Solvent A: | $CH_3CN$ + 0.05% TFA |
| Solvent B: | $H_2O$ + 0.05% TFA |

| Gradient: | |
|---|---|
| Time | composition |
| 0.0 min | A = 10%, B = 90% |
| 25.0 min | A = 95%, B = 10% |
| 30.0 min | A = 95%, B = 10% |

Method X

| Column: | Atlantis 150 × 2.1 mm, 3 μm |
|---|---|
| UV detector: | 190-420 nm |
| Flow rate: | 0.3 ml/min |
| Solvent A: | $CH_3CN$ + 0.02% TFA |
| Solvent B: | $H_2O$ + 0.02% TFA |

| Gradient: | |
|---|---|
| Time | composition |
| 0.0 min | A = 2%, B = 98% |
| 20.0 min | A = 98%, B = 2% |
| 30.0 min | A = 98%, B = 2% |

Method Y

| Column: | Xbridge Phenyl 250 × 4 mm, 3 μm |
|---|---|
| UV detector: | 190-420 nm |
| Flow rate: | 0.8 ml/min |
| Solvent A: | $CH_3CN$ + 5% THF + 0.02% TFA |
| Solvent B: | $H_2O$ + 0.02% HCOOH |

| Gradient: | |
|---|---|
| Time | composition |
| 0.0 min | A = 2%, B = 98% |
| 20.0 min | A = 98%, B = 2% |
| 30.0 min | A = 98%, B = 2% |
| 32.0 min | A = 2%, B = 98% |
| 40.0 min | A = 2%, B = 98% |

Method Z

| Column: | Atlantis T3 150 × 2.1 mm, 3 μm |
|---|---|
| UV detector: | 190-420 nm |
| Flow rate: | 0.3 ml/min |
| Solvent A: | $CH_3CN$ + 0.02% TFA |
| Solvent B: | $H_2O$ + 0.02% TFA |

| Gradient: | |
|---|---|
| Time | composition |
| 0.0 min | A = 5%, B = 95% |
| 20.0 min | A = 98%, B = 2% |
| 30.0 min | A = 98%, B = 2% |

EXAMPLE 1

N—[(S)-1-[(S)-2-(3-Butoxy-3-phenylazetidin-1-yl)-1-(4-methoxybenzyl)-2-oxoethylcarbamoyl]-2-(1H-imidazol-4-yl)ethyl]benzamide (compound No. 3; Table I)

1-1 (S)-2-[(S)-2-Benzoylamino-3-(1H-imidazol-4-yl)propionylamino]-3-(4-methoxyphenyl)propanoic acid 5.07 g (15.8 mmol) of TBTU are added to a solution containing 4.05 g (15.6 mmol) of (S)-2-benzoylamino-3-(1H-imidazol-4-yl)propanoic acid in 30 ml of DMF. The reaction medium is left to stir for 15 minutes at ambient temperature. 3 g (14.3 mmol) of methyl (S)-2-amino-3-(4-methoxyphenyl)propanoate and 7.5 ml of DIEA in 20 ml of DMF are added dropwise and stirred at ambient temperature for 4 hours. The reaction is stopped by adding water, and the organic products are extracted with dichloromethane. The organic phase is dried in the presence of magnesium sulphate. After filtration, the solvents are evaporated off. 6.56 g of a pale yellow solid are obtained and dissolved in 100 ml of THF. 29 ml of a 1N solution of LiOH are added. The reaction medium is stirred at ambient temperature for 16 hours. 20 ml of a saturated solution of ammonium chloride are added, followed by extraction with diethyl ether. The aqueous phase is acidified to pH 5 with a 1N solution of HCl. The white precipitate obtained is filtered off and oven-dried under vacuum at 40° C. 5.6 g (12.8 mmol) of (S)-2-[(S)-2-benzoylamino-3-(1H-imidazol-4-yl)propionylamino]-3-(4-methoxyphenyl)propanoic acid are obtained with a yield of 88%.

1-2 N—[(S)-1-[(S)-2-(3-Butoxy-3-phenylazetidin-1-yl)-1-(4-methoxybenzyl)-2-oxoethylcarbamoyl]-2-(1H-imidazol-4-yl)ethyl]benzamide 1-2-1 3-Hydroxy-3-phenyl-1-(tert-butoxycarbonyl)azetidine 3.9 ml (11.7 mmol) of a 3M solution of phenylmagnesium bromide in diethyl ether are added dropwise to a solution, immersed in a bath at −50° C., containing 500 mg (2.92 mmol) of 3-oxo-1-(tert-butoxycarbonyl)azetidine in 10 ml of THF. The medium is stirred for 1 hour at −50° C. and hydrolysed by adding a saturated solution of ammonium chloride. After a return to ambient temperature, a 1N solution of hydrochloric acid is added, followed by extraction with ethyl acetate. The organic phase is dried and evaporated to dryness. The crude product obtained is purified on silica in a 7/3 heptane/ethyl acetate mixture. 253 mg in the form of a white powder are obtained with a yield of 35%.

1-2-2 3-Butoxy-3-phenyl-1-(tert-butoxycarbonyl)azetidine

A solution of 1 g (4.0 mmol) of 3-hydroxy-3-phenyl-1-(tert-butoxycarbonyl)azetidine dissolved in 5 ml of DMF is added dropwise to a suspension of 300 mg of 60% NaH in 3 ml of DMF, immersed in a bath at 0° C. 2.5 ml of n-iodobutane are added dropwise. The reaction medium is left to stir at 0° C. for 15 minutes and 72 hours at ambient temperature. The medium is hydrolysed by addition of a saturated solution of ammonium chloride, followed by extraction with ethyl acetate. The organic phase is dried and evaporated to dryness. The crude product obtained is purified on silica in a 7/3 heptane/ethyl acetate mixture. 500 mg in the form of a light yellow oil are obtained with a yield of 41%.

1-2-3 3-Butoxy-3-phenylazetidine trifluoroacetate 1 ml of trifluoroacetic acid is added to a solution containing 500 mg (1.64 mmol) of 3-butoxy-3-phenyl-1-(tert-butoxycarbonyl)azetidine dissolved in 5 ml of dichloromethane. The reaction medium is stirred at ambient temperature for 3 hours and then concentrated. The crude product obtained is purified by silica gel chromatography (eluent 90/10 dichloromethane/methanol). 400 mg in the form of a pale yellow powder are obtained with a yield of 76%.

1-3 N—[(S)-1-[(S)-2-(3-Butoxy-3-phenylazetidin-1-yl)-1-(4-methoxybenzyl)-2-oxoethylcarbamoyl]-2-(1H-imidazol-4-yl)ethyl]benzamide 1 ml of a 3/2 dichloromethane/trifluoroacetic acid solution is added to 200 mg (0.343 mmol) of (S)-2-[(S)-2-benzoylamino-3-(1H-imidazol-4-yl)propionylamino]-3-(4-methoxyphenyl)propanoic acid. After stirring at ambient temperature for 1 hour, the solvents are evaporated off. The residue obtained is dissolved in 5 ml of DMF, and 110 mg (0.343 mmol) of TBTU and 2.37 ml of DIEA are added. The reaction medium is left to stir for 15 minutes at ambient temperature. 47 mg (0.147 mmol) of 3-butoxy-3-phenylazetidine trifluoroacetate dissolved in 5 ml of a 1/4 DCM/DMF solution are added dropwise and stirred at ambient temperature for 16 hours. A 5% citric acid solution is added, followed by extraction with dichloromethane. The organic phase is washed with a saturated solution of potassium hydrogen carbonate. The organic phase is dried and evaporated to dryness. The crude product obtained is purified by silica gel chromatography (eluent 9/1 dichloromethane/methanol). 55 mg of N—[(S)-1-[(S)-2-(3-butoxy-3-phenylazetidin-1-yl)-1-(4-methoxybenzyl)-2-oxoethylcarbamoyl]-2-(1H-imidazol-4-yl)ethyl]benzamide are obtained in the form of a white powder with a yield of 60%.

HPLC: (method A); 2 peaks (mixtures of conformers): retention time: 16.44 min and 16.60 min, (34+57)%, M+H: 624.

EXAMPLE 2

[1-[(S)-2-[(S)-2-benzoylamino-3-(1H-imidazol-4-yl)propionylamino]-3-(4-methoxyphenyl)propionyl]-3-(4-fluorophenyl)azetidin-3-yl] ester of butyric acid (compound No. 6; Table I)

2-1 3-(4-Fluorophenyl)-3-hydroxy-1-(tert-butoxycarbonyl)azetidine 6 ml (11.7 mmol) of a 2M solution of 4-fluorophenylmagnesium bromide in diethyl ether are added dropwise to a solution, immersed in a bath at −50° C., containing 500 mg (2.92 mmol) of 3-oxo-1-(tert-butoxycarbonyl)azetidine in 10 ml of THF. The medium is stirred for 1 hour at −50° C. and hydrolysed by addition of a saturated solution of ammonium chloride. After a return to ambient temperature, a 1N solution of hydrochloric acid is added, followed by extraction with ethyl acetate. The organic phase is dried and evaporated to dryness. The crude product obtained is purified by silica gel chromatography (eluent 7/3 heptane/ethyl acetate). 333 mg in the form of a white powder are obtained with a yield of 43%.

2-2 3-Butyryloxy-3-(4-fluorophenyl)-1-(tert-butoxycarbonyl)azetidine 23 mg (0.188 mmol) of DMAP and 0.03 ml of pyridine are added to a solution containing 50 mg (0.187 mmol) of 3-butyryloxy-3-(4-fluorophenyl)-1-(tert-butoxy-carbonyl)azetidine in 1 ml of dichloromethane. After stirring at ambient temperature for 10 minutes, 0.06 ml of butyric anhydride are introduced. After 3 hours, a saturated solution of ammonium chloride is added, followed by extraction with dichloromethane. The organic phase is dried and evaporated to dryness. The crude product obtained is purified by silica gel chromatography (eluent 7/3 heptane/ethyl acetate). 61 mg in the form of a colourless oil are obtained with a yield of 97%.

2-3 3-(4-Fluorophenyl)azetidin-3-yl butyrate trifluoroacetate 2 ml of trifluoroacetic acid are added to a solution containing 61 mg (0.181 mmol) of 3-hydroxy-3-(4-fluorophenyl)-1-(tert-butoxycarbonyl)azetidine dissolved in 8 ml of dichloromethane. The reaction medium is stirred at ambient temperature for 3 hours and then concentrated. The crude product obtained is purified by silica gel chromatography (eluent 90/10 dichloromethane/methanol). 40 mg in the form of a pale yellow oil are obtained with a yield of 63%.

2-4 1-[(S)-2-[(S)-2-benzoylamino-3-(1H-imidazol-4-yl)propionylamino]-3-(4-methoxyphenyl)propionyl]-3-(4-fluorophenyl)azetidin-3-yl ester of butyric acid 1 ml of a 3/2 dichloromethane/trifluoroacetic acid solution is added to 109 mg (0.252 mmol) of (S)-2-[(S)-2-benzoylamino-3-(1H-imidazol-4-yl)propionylamino]-3-(4-methoxyphenyl)propanoic acid (cf. procedure 1-1). After stirring at ambient temperature for 1 hour, the solvents are evaporated off. The residue obtained is dissolved in 5 ml of DMF and 81 mg (0.252 mmol) of TBTU and 1.74 ml of DIEA are added. The reaction medium is left to stir for 15 minutes at ambient temperature. 40 mg (0.114 mmol) of 3-(4-fluorophenyl)azetidin-3-yl butyrate trifluoroacetate dissolved in 5 ml of a 1/4 dichloromethane/dimethylformamide solution are added dropwise and stirred at ambient temperature for 16 hours. A 5% citric acid solution is added, followed by extraction with dichloromethane. The organic phase is washed with a saturated solution of potassium hydrogen carbonate. The organic phase is dried and evaporated to dryness. The crude product obtained is purified by silica gel chromatography (eluent 9/1 dichloromethane/methanol). 19 mg of 1-[(S)-2-[(S)-2-benzoylamino-3-(1H-imidazol-4-yl)propionylamino]-3-(4-methoxyphenyl)propionyl]-3-(4-fluorophenyl)azetidin-3-yl ester of butyric acid are obtained in the form of a white powder with a yield of 25%.

HPLC: (method B): 2 peaks (mixtures of conformers): retention time: 13.51 min and 13.72 min, (28+55)%, M+H: 656.

EXAMPLE 3

N—[(S)-1-[(S)-2-(3-cyclohexyl-3-hydroxyazetidin-1-yl)-1-(4-methoxybenzyl)-2-oxoethylcarbamoyl]-2-(1H-imidazol-4-yl)ethyl]benzamide (compound No. 7; Table I)

3-1 3-Cyclohexyl-3-hydroxy-1-(tert-butoxy-carbonyl)azetidine 0.5 ml of acetic acid and 40 mg of rhodium on alumina 5% are added to a solution containing 117 mg (0.470 mmol) of 3-hydroxy-3-phenyl-1-(tert-butoxycarbonyl)azetidine (cf. procedure 1-2-1) dissolved in 4 ml of methanol. The reaction medium is placed at 4 bar of hydrogen and heated at 85° C. for 4 hours. The catalyst is filtered off and washed with methanol and the solvents are evaporated off. 120 mg in the form of a beige powder are obtained with a yield of 100%.

3-2 3-Cyclohexylazetidin-3-ol trifluoroacetate 1 ml of trifluoroacetic acid is added to a solution containing 120 mg (0.47 mmol) of 3-cyclohexyl-3-hydroxy-1-(tert-butoxycarbonyl)azetidine dissolved in 3 ml of dichloromethane. The reaction medium is stirred at ambient temperature for 1 hour and then concentrated to dryness and used without further purification.

3-3 N—[(S)-1-[(S)-2-(3-Cyclohexyl-3-hydroxyazetidin-1-yl)-1-(4-methoxybenzyl)-2-oxoethylcarbamoyl]-2-(1H-imidazol-4-yl)ethyl]benzamide 1 ml of a 3/2 dichloromethane/trifluoroacetic acid solution is added to 84 mg (0.193 mmol) of (S)-2-[(S)-2-benzoylamino-3-(1H-imidazol-4-yl)propionylamino]-3-(4-methoxyphenyl)propanoic acid (cf. procedure 1-1). After stirring at ambient temperature for 1 hour, the solvents are evaporated off. The residue obtained is dissolved in 1 ml of DMF, and 79 mg (0.246 mmol) of TBTU and 15 drops of DIEA are added. 0.235 mmol of 3-cyclohexylazetidin-3-ol trifluoroacetate dissolved in 1 ml of a DCM solution is added dropwise and stirred at ambient temperature for 2 hours. A saturated solution of potassium hydrogen carbonate is added, followed by extraction with dichloromethane. The organic phase is washed with a saturated solution of potassium hydrogen carbonate. The organic phase is dried and evaporated to dryness. The crude product obtained is purified by silica gel chromatography (eluent 85/15 dichloromethane/methanol mixture). 35 mg of N—[(S)-1-[(S)-2-(3-cyclohexyl-3-hydroxyazetidin-1-yl)-1-(4-methoxybenzyl)-2-oxoethylcarbamoyl]-2-(1H-imidazol-4-yl)ethyl]benzamide are obtained in the form of a yellow powder with a yield of 32%.

HPLC: (method B): 2 peaks (mixture of conformers): retention time: 10.68 min and 10.94 min, (36+62)%, M+H: 574.

EXAMPLE 4

N—[(R)-1-(4-methoxybenzyl)-2-oxo-2-(3-pentyloxy-3-o-tolylazetidin-1-yl)ethyl]-3-(1H-imidazol-4-yl)propionamide (compound No. 24; Table I)

4-1 3-Pentyloxy-3-o-tolyl-1-(tert-butoxy-carbonyl)azetidine

A solution of 3.53 g (13.4 mmol) of 3-hydroxy-3-phenyl-1-(tert-butoxycarbonyl)azetidine (cf. procedure 1-2-1) is added dropwise to a suspension of 1.07 g (26.8 mmol) of 60% NaH in 17 ml of DMF, immersed in a bath at 0° C. 9.0 ml of n-iodopentane are added dropwise. The reaction medium is left to stir at 0° C. for 15 minutes and 24 hours at ambient temperature. The medium is hydrolysed by addition of a saturated solution of ammonium chloride, followed by extraction with ethyl acetate. The organic phase is dried and evaporated to dryness. The crude product obtained is purified by silica gel chromatography (eluent 7/3 heptane/ethyl acetate). 3.41 g in the form of a light yellow oil are obtained with a yield of 76%.

4-2 3-pentoxy-3-phenylazetidine trifluoroacetate 5.5 ml of trifluoroacetic acid are added to a solution containing 3.34 g (10 mmol) of 3-pentoxy-3-phenyl-1-(tert-butoxycarbonyl)azetidine dissolved in 10 ml of dichloromethane. The reaction medium is stirred at ambient temperature for 2 hours 30 min and then concentrated. The crude product obtained is purified by silica gel chromatography (eluent 90/10 dichloromethane/methanol). 3.5 g in the form of a pale yellow oil are obtained with a yield of 100%.

4-3 tert-butyl [(R)-1-(4-methoxybenzyl)-2-oxo-2-(3-pentyloxy-3-o-tolylazetidin-1-yl)ethyl]carbamate 2.93 g (9.93 mmol) of (R)-2-tert-butoxycarbonylamino-3-(4-methoxyphenyl)propionic acid are dissolved in 10 ml of DMF. 2.08 g (10.9 mmol) of EDC, 1.47 g (10.9 mmol) of HOBt and a solution of 3.45 g (9.93 mmol) of 3-pentoxy-3-phenylazetidine trifluoroacetate in 15 ml of DMF are then added. 7 ml (40.2 mmol) of DIEA are added. The reaction medium is stirred at ambient temperature for 2 h 30 and then extracted with ethyl acetate. The organic phase is washed with 1N sodium hydroxide and then dried over magnesium sulphate, filtered and evaporated. The crude product obtained is purified by silica gel chromatography (eluent 6/4 heptane/ethyl acetate). 2.83 g in the form of a white powder are obtained with a yield of 56%.

4-4 (R)-2-Amino-3-(4-methoxyphenyl)-1-(3-pentyloxy-3-o-tolylazetidin-1-yl)propan-1-one trifluoroacetate 2.81 g (5.5 mmol) of tert-butyl [(R)-1-(4-methoxybenzyl)-2-oxo-2-(3-pentyloxy-3-o-tolylazetidin-1-yl)ethyl]carbamate are solubilized in 10 ml of dichloromethane. The reaction medium is cooled to 0° C. 6.5 ml of trifluoroacetic acid are then introduced. After a return to ambient temperature, the reaction medium is stirred for 5 hours and then concentrated to dryness. The crude product obtained is purified by silica gel chromatography (eluent 9/1 dichloromethane/methanol). 2.81 g in the form of a white powder are obtained with a yield of 97%.

4-5 N—[(R)-1-(4-Methoxybenzyl)-2-oxo-2-(3-pentyloxy-3-o-tolylazetidin-1-yl)ethyl]-3-(1H-imidazol-4-yl)propionamide 670 mg (2.08 mmol) of TBTU, 0.8 ml of triethylamine and then 1.0 g (1.91 mmol) of (R)-2-amino-3-(4-methoxyphenyl)-1-(3-pentyloxy-3-o-tolylazetidin-1-yl)propan-1-one trifluoroacetate are added to a solution containing 370 mg (2.10 mmol) of desamino-histidine hydrochloride in 15 ml of dimethylformamide. The reaction medium is stirred at ambient temperature for 21 hours. The reaction is stopped by adding a 1N solution of sodium hydroxide and then extraction with dichloromethane is carried out. The organic phases are combined and dried over sodium sulphate. After filtration, the solvents are evaporated off and the residue is then purified by silica gel chromatography (eluent 90/10 dichloromethane/methanol). 598 mg of N—[(R)-1-(4-methoxybenzyl)-2-oxo-2-(3-pentyloxy-3-o-tolylazetidin-1-yl)ethyl]-3-(1H-imidazol-4-yl)propionamide are obtained in the form of a white powder with a yield of 59%.

HPLC: (method M); retention time: 18.20 min, 99%, M+H: 533.

EXAMPLE 5

N—[(R)-1-(4-methoxybenzyl)-2-oxo-2-(3-pentyl-3-phenylazetidin-1-yl)ethyl]-3-(1H-imidazol-4-yl)propionamide (compound No. 26; Table I)

5-1 Methyl (R)-2-amino-3-(4-methoxyphenyl)propanoate 20 ml of sulphuric acid are added, dropwise, over a period of 30 minutes, to a solution containing 13 g (66.6 mmol) of (R)-2-amino-3-(4-methoxyphenyl)propionic acid in 150 ml of methanol. After stirring for 24 hours at ambient temperature, the reaction medium is basified to pH 8-9 by introducing 10N sodium hydroxide and a saturated solution of sodium hydrogen carbonate, followed by extraction with dichloromethane. The organic phase is dried over sodium sulphate, filtered and evaporated. 12.8 g in the form of a pale yellow oil are obtained with a yield of 92%.

5-2 Methyl (R)-2-(3-1H-imidazol-4-ylpropionylamino)-3-(4-methoxyphenyl)propanoate 35.5 ml of DIEA are added to a solution containing 13.2 g (74.7 mmol) of desamino-histidine hydrochloride and 24 g (74.7 mmol) of TBTU in 100 ml of DMF. After stirring for 15 minutes at ambient temperature, 14.2 g (67.9 mmol) of methyl (R)-2-amino-3-(4-methoxyphenyl)-propanoate in 150 ml of DMF are added. The reaction medium is left to stir for 16 hours and then basified to pH=8-9 by introducing 1N sodium hydroxide and a saturated solution of sodium hydrogen carbonate, followed by extraction with dichloromethane. The organic phase is dried over sodium sulphate, filtered and evaporated. The crude product obtained is purified by silica gel chromatography (eluent 85/15 dichloromethane/methanol). 11.0 g in the form of an orange oil are obtained with a yield of 49%.

5-3 (R)-2-(3-1H-imidazol-4-ylpropionylamino)-3-(4-methoxyphenyl)propanoic acid 40 ml of a 1N aqueous solution of lithium hydroxide are added to a solution containing 11.0 g (33.3 mmol) of methyl (R)-2-(3-1H-imidazol-4-ylpropionylamino)-3-(4-methoxyphenyl)propanoate in 100 ml of THF. After stirring for 16 hours, the reaction medium is concentrated. The residue is purified by silica gel chromatography (eluent 70/30/1 dichloromethane/methanol/triethylamine). 8.4 g in the form of a white powder are obtained with a yield of 79%.

5-4-1 2-Phenylheptanenitrile 5 g (42.7 mmol) of phenylacetonitrile are added dropwise to a suspension of 2 g of 60% NaH in 50 ml of DMF cooled to 0° C. After stirring for 30 minutes at 0° C., 5.32 ml (42.7 mmol) of bromopentane are added dropwise. The reaction medium is stirred for 16 hours at ambient temperature and then treated with ice and extracted with ethyl ether. The organic phase is washed with a saturated aqueous solution of sodium hydrogen carbonate, dried over sodium sulphate, filtered and evaporated under pressure. An orangey-yellow oil is obtained and purified by fractionated distillation under reduced pressure (70-75° C. under $1\times10^{-1}$ mbar). 5.14 g in the form of an orangey oil are obtained with a yield of 64%.

5-4-2 2-Hydroxymethyl-2-phenylheptanenitrile 5.14 g (27.4 mmol) of 2-phenylheptanenitrile are added to a suspension of 1.34 g of 60% NaH in 50 ml of DMF cooled to 0° C. After stirring for 30 minutes, 7.6 g (220 mmol) of paraformaldehyde are added portionwise. The reaction medium is left to stir at ambient temperature for 6 hours and then hydrolysed with ice and extracted with diethyl ether. The organic phase is washed with a saturated aqueous solution of sodium hydrogen carbonate, dried over sodium sulphate, filtered and evaporated under pressure. The crude product obtained is purified by silica gel chromatography (eluent 8/2 heptane/ethyl acetate). 4.24 g in the form of a pale yellow oil are obtained with a yield of 71%.

5-4-3 2-cyano-2-phenylheptyl ester of toluene-4-sulphonic acid 4.1 g (21.5 mmol) of p-toluenesulphonyl chloride and 6 ml of triethylamine are added to a solution containing 4.24 g (19.5 mmol) of 2-hydroxymethyl-2-phenylheptanenitrile in 25 ml of dichloromethane. The reaction medium is left to stir for 15 hours at ambient temperature and then treated with a 1N solution of hydrochloric acid and extracted with dichloromethane. The organic phase is dried over sodium sulphate, filtered and evaporated under pressure. A yellow oil is obtained and precipitated from a 9/1 heptane/diisopropyl ether mixture. The precipitate formed is filtered off and rinsed with diisopropyl ether. 5.26 g in the form of a beige powder are obtained with a yield of 72%.

5-4-4 3-Pentyl-3-phenylazetidine 600 mg (15.52 mmol) of powdered LiAlH$_4$ are added carefully to a solution containing 5.26 g (14.15 mmol) of 2-cyano-2-phenylheptyl ester of toluene-4-sulphonic acid in 25 ml of THF under nitrogen. The reaction medium is left to stir for 1 hour at ambient temperature and then treated with an aqueous solution of sodium sulphate. After stirring for 30 minute at ambient temperature, the salts formed are filtered off and the filtrate is evaporated under reduced pressure. The residue is taken up in dichloromethane and washed with a 1N aqueous solution of sodium hydroxide. The organic phase is dried over sodium sulphate, filtered and evaporated under reduced pressure. 2.90 g in the form of a colourless oil are obtained and used in the next stage without further purification.

5-4-5 N—[(R)-1-(4-methoxybenzyl)-2-oxo-2-(3-pentyl-3-phenylazetidin-1-yl)ethyl]-3-(1H-imidazol-4-yl)propionamide 70 mg (0.345 mmol) of 3-pentyl-3-phenylazetidine and 100 mg (0.315 mmol) of (R)-2-(3-1H-imidazol-4-ylpropionylamino)-3-(4-methoxyphenyl)propanoic acid are solubilized in 1 ml of DMF. 67 mg (0.345 mmol) of EDC and 47 mg (0.345 mmol) of HOBT are added to this solution. The whole is left to stir for 4 hours and is then treated with 1N sodium hydroxide and extracted with dichloromethane. The organic phase is dried over sodium sulphate, filtered and evaporated under pressure. The crude product obtained is purified by silica gel chromatography (eluent 9/1 dichloromethane/methanol). 85 mg of N—[(R)-1-(4-methoxybenzyl)-2-oxo-2-(3-pentyl-3-phenylazetidin-1-yl)ethyl]-3-(1H-imidazol-4-yl)propionamide are obtained in the form of a white powder with a yield of 49%.

HPLC: (method L); retention time: 22.96 min, 97%, M+H: 503.

EXAMPLE 6

N—[(R)-2-(3-Butoxy-3-o-tolylazetidin-1-yl)-1-(4-methoxybenzyl)-2-oxoethyl]-3-(1H-[1,2,3]triazol-4-yl)propionamide (compound No. 39; Table I)

6-1 3-(1H-[1,2,3]triazol-4-yl)propanoic acid 39 mg of palladium-on-charcoal at 10% are added to a solution containing 390 mg (1.7 mmol) of 3-(1-benzyl-1H[1,2,3]triazol-4-yl)propanoic acid in 3 ml of methanol. The reaction mixture is placed under 10 bar of hydrogen pressure and stirred at 60° C. for 16 hours. After filtration through celite, the solvents are evaporated off and the residue is purified by silica gel chromatography (eluent 95/5 dichloromethane/methanol). 159.8 mg of 3-(1H[1,2,3]triazol-4-yl)propanoic acid are obtained in the form of a white powder with a yield of 67%.

6-2 (R)-2-amino-3-(4-methoxyphenyl)-1-(3-butyloxy-3-o-tolylazetidin-1-yl)propan-1-one hydrochloride 6 ml of a 4N solution of hydrochloric acid in ethyl acetate are added to 615 mg (1.24 mmol) of tert-butyl [(R)-2-(3-butoxy-3-o-tolylazetidin-1-yl)-1-(4-methoxybenzyl)-2-oxoethyl]carbamate (procedure identical to 4-3). The reaction mixture is stirred at ambient temperature for 2 hours. The precipitate obtained is filtered off, washed with diethyl ether and then dissolved in methanol, followed by evaporation of the solvents. 441 mg of (R)-2-amino-1-(3-butoxy-3-o-tolylazetidin-1-yl)-3-(4-methoxyphenyl)propan-1-one hydrochloride are obtained in the form of a white powder with a yield of 82%.

6-3 N—[(R)-2-(3-Butoxy-3-o-tolylazetidin-1-yl)-1-(4-methoxybenzyl)-2-oxoethyl]-3-(1H[1,2,3]triazol-4-yl)propionamide 146 mg (0.34 mmol) of (R)-2-amino-1-(3-butoxy-3-o-tolylazetidin-1-yl)-3-(4-methoxyphenyl)propan-1-one hydrochloride in 2 ml of dimethylformamide are added to a solution of 47 mg (0.34 mmol) of 3-(1H[1,2,3]triazol-4-yl)propanoic acid, 119 mg (0.37 mmol) of TBTU and 0.15 ml (1.1 mmol) of triethylamine in 2 ml of dimethylformamide. The reaction mixture is stirred for 2 hours at ambient temperature. The reaction is stopped by adding 10 ml of water and then extracted with ethyl acetate. The organic phases are combined, washed with a 1N solution of sodium hydroxide and then a saturated solution of sodium chloride, and dried over sodium sulphate. After filtration, the solvents are evaporated off and the residue is then purified by silica gel chromatography (eluent 90/10 ethyl acetate/heptane). 78.6 mg of N—[(R)-2-(3-butoxy-3-o-tolylazetidin-1-yl)-1-(4-methoxybenzyl)-2-oxoethyl]-3-(1H[1,2,3]triazol-4-yl)propionamide are obtained in the form of a white powder with a yield of 45%.

HPLC: (method M); retention time: 19.03 min, 93%, M+H: 520.

EXAMPLE 7

N—[(R)-2-(3-Butoxy-3-o-tolylazetidin-1-yl)-1-(4-methoxybenzyl)-2-oxoethyl]-3-(5-methyl-3H-imidazol-4-yl)propionamide (compound No. 41; Table I)

7-1 3-(5-Methyl-3H-imidazol-4-yl)propanoic acid 50 mg of palladium-on-charcoal at 10% are added to 500 mg (2.65 mmol) of 3-(5-methyl-3H-imidazol-4-yl)acrylic acid chloride in 10 ml of a 0.5N solution of sodium hydroxide. The reaction mixture is placed under 6 bar of hydrogen pressure and stirred at 80° C. for 72 hours. After having filtered off the catalyst through celite, the residue is acidified to pH 2 with hydrochloric acid, concentrated to dryness and taken up in ethanol. The insoluble material is filtered off and the filtrate is concentrated to dryness. 102 mg of 3-(5-methyl-3H-imidazol-4-yl)propanoic acid chloride are obtained in the form of a white powder with a yield of 16%.

7-2 N—[(R)-2-(3-Butoxy-3-o-tolylazetidin-1-yl)-1-(4-methoxybenzyl)-2-oxoethyl]-3-(5-methyl-3H-imidazol-4-yl)propionamide 146 mg (0.34 mmol) of (R)-2-amino-3-(4-methoxyphenyl)-1-(3-butyloxy-3-o-tolylazetidin-1-yl)propan-1-one hydrochloride in solution in 2 ml of dimethylformamide are added to a solution of 64 mg (0.34 mmol) of 3-(5-methyl-3H-imidazol-4-yl)propanoic acid chloride, 119 mg (2.34 mmol) of TBTU and 0.15 ml (1.1 mmol) of triethylamine in 2 ml of dimethylformamide. The reaction mixture is stirred for 2 hours at ambient temperature. The reaction is stopped by adding 10 ml of water and then extracted with ethyl acetate. The organic phases are combined, washed with a 1N solution of sodium hydroxide and then a saturated solution of sodium chloride, and dried over sodium sulphate. After filtration, the solvents are evaporated off and the residue is then purified by silica gel chromatography (eluent 90/10 dichloromethane/methanol). 154 mg of N—[(R)-2-(3-butoxy-3-o-tolylazetidin-1-yl)-1-(4-methoxybenzyl)-2-oxoethyl]-3-(5-methyl-3H-imidazol-4-yl)propionamide are obtained in the form of a white powder with a yield of 86%.

HPLC: (method M); retention time: 17.65 min, 96%, M+H: 533.

EXAMPLE 8

N—[(S)-2-(3-Hydroxy-3-o-tolylazetidin-1-yl)-1-(4-methoxybenzyl)-2-oxoethyl]-3-(1H-imidazol-4-yl)propionamide (compound No. 11; Table I)

8-1 3-Hydroxy-3-phenylazetidine trifluoroacetate 1 ml of trifluoroacetic acid is added to a solution containing 50 mg (0.19 mmol) of tert-butyl 3-hydroxy-3-phenylazetidine-1-carboxylate dissolved in 4 ml of dichloromethane. The reaction medium is stirred at ambient temperature for 3 hours and then concentrated. The crude product obtained is purified by silica gel chromatography (eluent 90/10 dichloromethane/methanol). 36 mg in the form of a white powder are obtained with a yield of 68%.

8-2 N—[(S)-2-(3-Hydroxy-3-o-tolylazetidin-1-yl)-1-(4-methoxybenzyl)-2-oxoethyl]-3-(1H-imidazol-4-yl)propionamide trifluoroacetate 2 ml of DMF, 106 mg (0.33 mmol) of TBTU and 1 ml of DIEA are added to 105 mg (0.33 mmol) of (R)-2-(3-1H-imidazol-4-ylpropionylamino)-3-(4-methoxyphenyl)propanoic acid. The reaction medium is left to stir for 15 minutes at ambient temperature. 36 mg (0.13 mmol) of 3-hydroxy-3-phenylazetidine trifluoroacetate dissolved in 5 ml of a 1/4 DCM/DMF solution are added dropwise and stirred at ambient temperature for 16 hours. A 5% citric acid solution is added, followed by extraction with dichloromethane. The organic phase is washed with a saturated solution of potassium hydrogen carbonate. The organic phase is dried and evaporated to dryness. The crude product obtained is purified by silica gel chromatography (eluent 9/1 dichloromethane/methanol). 6 mg of N—[(S)-2-(3-hydroxy-3-o-tolylazetidin-1-yl)-1-(4-methoxybenzyl)-2-oxoethyl]-3-(1H-imidazol-4-yl)propionamide trifluoroacetate are obtained in the form of a white powder with a yield of 10%.

HPLC: (method D); retention time: 9.25 min, 89%, M+H: 463.

EXAMPLE 9

N—[(R)-2-[3-(4-Fluorophenyl)-3-pentylazetidin-1-yl]-1-(4-methoxybenzyl)-2-oxoethyl]-3-(1H-imidazol-4-yl)propionamide (compound No. 38; Table I)

9-1-1 (4-Fluorophenyl)heptanenitrile 5 g (37.0 mmol) of (4-fluorophenyl)acetonitrile are added dropwise to a suspension of 1.62 g of 60% NaH in 50 ml of DMF cooled to 0° C. After stirring for 30 minutes at 0° C., 4.62 g (37.0 mmol) of bromopentane are added dropwise. The reaction medium is stirred for 16 hours at ambient temperature and then treated with ice and extracted with dichloromethane. The organic phase is dried over sodium sulphate, filtered and evaporated under pressure. An orangey-yellow oil is obtained and used as it is in the next stage.

9-1-2 2-Hydroxymethyl-2-(4-fluorophenyl)-heptanenitrile

The crude (4-fluorophenyl)heptanenitrile obtained in stage 9-1-1 is added to a suspension of 1.62 g of 60% NaH in 50 ml of DMF cooled to 0° C. After stirring for 30 minutes, 8.9 g (296 mmol) of paraformaldehyde are added portionwise. The reaction medium is left to stir at ambient temperature for 3 hours and then hydrolysed with ice and extracted with dichloromethane. The organic phase is dried over sodium sulphate, filtered and evaporated under pressure. The crude product obtained is purified by silica gel chromatography (eluent 8/2 heptane/ethyl acetate). 3.85 g in the form of a pale yellow oil are obtained with a yield of 44%.

9-1-3 2-cyano-2-(4-fluorophenyl)heptyl ester of toluene-4-sulphonic acid 3.43 g (18.0 mmol) of p-toluenesulphonyl chloride and 5 ml of triethylamine are added to a solution containing 3.85 g (16.4 mmol) of 2-hydroxymethyl-2-(4-fluorophenyl)heptanenitrile in 40 ml of dichloromethane. The reaction medium is left to stir for 15 hours at ambient temperature and then treated with a 1N solution of hydrochloric acid and extracted with dichloromethane. The organic phase is dried over sodium sulphate, filtered and evaporated under pressure. A yellow oil is obtained and precipitated from an 8/2 dichloromethane/diisopropyl ether mixture. The precipitate formed is filtered off. 4.4 g in the form of a beige powder are obtained with a yield of 65%.

9-1-4 3-Pentyl-3-(4-fluorophenyl)azetidine 471 mg (12.4 mmol) of powdered LiAlH$_4$ are added carefully to a solution containing 4.4 g (11.3 mmol) of 2-cyano-2-(4-fluorophenyl)heptyl ester of toluene-4-sulphonic acid in 40 ml of THF under nitrogen. The reaction medium is left to stir for 1 hour at ambient temperature and then treated with an aqueous solution of sodium sulphate. After stirring for 30 minutes at ambient temperature, the salts formed are filtered off and the filtrate is evaporated under reduced pressure. The residue is taken up in dichloromethane and washed with a 1N aqueous solution of sodium hydroxide. The organic phase is dried over sodium sulphate, filtered and evaporated under reduced pressure. 2.02 g in the form of a yellow oil are obtained and used in the next stage without further purification.

9-2 Tert-butyl [(R)-1-(4-methoxybenzyl)-2-oxo-2-(3-pentyl-3-(4-fluorophenyl)azetidin-1-yl)ethyl]carbamate 606 mg (2.05 mmol) of (R)-2-tert-butoxycarbonylamino-3-(4-methoxyphenyl)propionic acid and 500 mg (2.26 mmol) of 3-pentyl-3-(4-fluoro-phenyl)azetidine are dissolved in 10 ml of DMF. 473 mg (2.46 mmol) of EDC, 333 mg (2.46 mmol) of HOBt and 0.6 ml (4.5 mmol) of triethylamine are added to this solution. The reaction medium is stirred at ambient temperature for 5 h and then extracted with dichloromethane. The organic phase is washed with 1N sodium hydroxide and then dried over magnesium sulphate, filtered and evaporated. The crude product obtained is purified by silica gel chromatography (eluent 6/4 heptane/ethyl acetate). 780 mg in the form of a white powder are obtained with a yield of 76%.

9-3 (R)-2-Amino-3-(4-methoxyphenyl)-1-(3-pentyl-3-(4-fluorophenyl)azetidin-1-yl)-propan-1-one 780 mg (1.56 mmol) of tert-butyl [(R)-1-(4-methoxybenzyl)-2-oxo-2-(3-pentyl-3-(4-fluoro-phenyl)azetidin-1-yl) ethyl]carbamate are solubilized in 10 ml of dichloromethane. 4 ml of trifluoroacetic acid are introduced. The reaction medium is stirred for 1 hour and then concentrated to dryness. The residue is taken up in a 1N aqueous solution of sodium hydroxide and extracted with dichloromethane and then the resulting product is dried over magnesium sulphate, filtered and evaporated.

590 mg in the form of a colourless resin are obtained with a yield of 95%.

9-4 N—[(R)-2-[3-(4-Fluorophenyl)-3-pentylazetidin-1-yl]-1-(4-methoxybenzyl)-2-oxoethyl]-3-(1H-imidazol-4-yl)propionamide 600 mg (1.86 mmol) of TBTU and 0.45 ml of triethylamine are added to a solution containing 330 mg (1.86 mmol) of desamino-histidine hydrochloride in 5 ml of dimethylformamide. After stirring for 15 minutes, 590 mg (1.55 mmol) of (R)-2-amino-3-(4-methoxyphenyl)-1-(3-pentyl-3-(4-fluorophenyl)azetidin-1-yl)-propan-1-one dissolved in 5 ml of dimethylformamide are added. The reaction medium is stirred at ambient temperature for 3 days. The reaction is stopped by adding a 1N solution of sodium hydroxide and then extracted with a 1/1 heptane/ethyl acetate mixture. The organic phases are combined and dried over sodium sulphate. After filtration, the solvents are evaporated off and the residue is then purified by silica gel chromatography (eluent 85/15 dichloromethane/methanol). 490 mg of N—[(R)-2-[3-(4-fluorophenyl)-3-pentylazetidin-1-yl]-1-(4-methoxybenzyl)-2-oxoethyl]-3-(1H-imidazol-4-yl)-propionamide are obtained in the form of a white powder with a yield of 61%.

HPLC: (method 0); retention time: 15.85 min, 99%, M+H: 521.

EXAMPLE 10

N-[2-(3-Butoxy-3-o-tolylazetidin-1-yl)-1-(4-methoxybenzyl)-2-oxoethyl]-3-(1H-imidazol-4-yl) hexyramide (compound No. 62; Table I)

10-1-1 6-(1-Trityl-1H-imidazol-4-yl)hex-5-enoic acid 13.5 ml (14.3 mmol) of a solution of lithium hexamethyldisilazane at 1.06 M in THF are added to 3.27 g (7.38 mmol) of (4-carboxybutyl)triphenyl-phosphonium bromide in suspension in 45 ml of THF cooled to −75° C. The reaction medium is stirred at −75° C. for 20 minutes and then at 0° C. for 15 minutes. After a return to −75° C., 1.50 g (4.43 mmol) of 1-trityl-1H-imidazole-4-carbaldehyde in suspension in 15 ml of THF are introduced. After a return to ambient temperature, the reaction medium is stirred for 20 hours and then at 90° C. with microwave-heating for 5 minutes. The reaction medium is filtered and concentrated in a rotary evaporator and then taken up in 1/1 heptane/EtOAc. The organic phase is washed with a saturated aqueous solution of NaHCO$_3$. The aqueous phase obtained is acidified to pH=5 with an aqueous solution of citric acid at 5% and then extracted with a 1/1 heptane/EtOAc mixture. The organic phase is dried over MgSO$_4$, filtered and concentrated in a rotary evaporator. 0.58 g of 6-(1-trityl-1H-imidazol-4-yl)hex-5-enoic acid in the form of a beige powder are obtained with a yield of 31%.

10-1-2 6-(1H-imidazol-4-yl)hex-5-enoic acid trifluoroacetate 2 ml of trifluoroacetic acid are added to 0.58 g (1.37 mmol) of 6-(1-trityl-1H-imidazol-4-yl)hex-5-enoic acid in suspension in 8 ml of dichloromethane. After the solvents have been evaporated off, the oil obtained is purified on a silica column (eluent 8/2 DCM/MeOH). 240 mg of 6-(1H-imidazol-4-yl)hex-5-enoic acid trifluoroacetate in the form of a yellow oil are isolated with a yield of 60%.

10-1-3 6-(1H-imidazol-4-yl)hexanoic acid trifluoroacetate 4 ml of acetic acid and 80 mg of palladium-on-charcoal at 10% are added to 218 mg (0.741 mmol) of 6-(1H-imidazol-4-yl)hex-5-enoic acid trifluoroacetate. The reaction medium is placed under a hydrogen atmosphere at atmospheric pressure. After 13 hours, the reaction medium is filtered through celite. After the solvents have been evaporated off, 175 mg of 6-(1H-imidazol-4-yl)hexanoic acid trifluoroacetate in the form of a yellow oil are obtained with a yield of 80%.

10-2 N-[2-(3-Butoxy-3-o-tolylazetidin-1-yl)-1-(4-methoxybenzyl)-2-oxoethyl]-3-(1H-imidazol-4-yl) hexyramide 60 mg (0.186 mmol) of TBTU, 0.1 ml (0.715 mmol) of triethylamine and a solution of 79 mg (0.155 mmol) of 2-amino-1-(3-butoxy-3-o-tolylazetidin-1-yl)-3-(4-methoxyphenyl)propan-1-one trifluoroacetate (cf. procedure 4-4) in 1 ml of DMF are added to 55 mg (0.186 mmol) of 6-(1H-imidazol-4-yl)hexanoic acid trifluoroacetate dissolved in 1 ml of DMF. The reaction medium is stirred for 66 hours and is extracted with a 1/2 heptane/EtOAc mixture and then washed with 1N sodium hydroxide. The organic phase is dried over MgSO$_4$, filtered and concentrated. The crude product obtained is purified on a silica column (eluent 8/2 DCM/MeOH). 40.8 mg of N-[2-(3-butoxy-3-o-tolylazetidin-1-yl)-1-(4-methoxybenzyl)-2-oxoethyl]-3-(1H-imidazol-4-yl)hexyramide are obtained in the form of a white powder with a yield of 47%.

HPLC: (method V); retention time: 18.05 min, 99%, M+H: 561.

EXAMPLE 11

N—[(R)-1-(4-Methoxybenzyl)-2-oxo-2-(3-pentyl-3-phenylazetidin-1-yl)ethyl]-3-(3-methyl-3H-imidazol-4-yl)propionamide (compound No. 64; Table I)

11-1-1 5-(2-methoxycarbonylethyl)-1-methyl-3-trityl-3H-imidazol-1-ium iodide 720 mg (5.2 mmol) of potassium carbonate and 0.34 ml (5.72 mmol) of iodomethane are added to a solution of 1 g (2.6 mmol) of N-1-trityl-desamino-histidine in 10 ml of DMF. The reaction medium is heated at 60° C. for 3 hours. After a return to ambient temperature, the reaction medium is treated with water and acetic acid (to pH 4-5) and extracted with dichloromethane. The organic phase is dried over MgSO$_4$, filtered and evaporated. The residue obtained is purified by silica chromatography (eluent 8/2 DCM/MeOH). 970 mg of 5-(2-methoxycarbonylethyl)-1-methyl-3-trityl-3H-imidazol-1-ium iodide are obtained with a yield of 69%.

11-1-2 Methyl 3-(3-methyl-3H-imidazol-4-yl)propionate trifluoroacetate 0.5 ml of trifluoroacetic acid is added to a solution of 200 mg (0.37 mmol) of 5-(2-methoxycarbonylethyl)-1-methyl-3-trityl-3H-imidazol-1-ium iodide in 2 ml of dichloromethane. The reaction medium is left to stir overnight at ambient temperature and the solvents are evaporated off. The residue is purified by silica chromatography (eluent 9/1 DCM/MeOH. 80 mg of methyl 3-(3-methyl-3H-imidazol-4-yl)propionate trifluoroacetate are obtained with a yield of 76%.

11-1-3 3-(3-Methyl-1H-imidazol-4-yl)propionic acid hydrochloride 2 ml of an aqueous solution of sodium hydroxide at 30% are added to a solution of 320 mg (1.13 mmol) of methyl 3-(3-methyl-3H-imidazol-4-yl)propionate trifluoroacetate in 10 ml of THF. The reaction medium is stirred at ambient temperature for 16 hours and then cooled to 0° C., and concentrated hydrochloric acid is added dropwise until pH 1 is obtained. After filtration, the filtrate is evaporated. 87 mg of 3-(3-methyl-1H-imidazol-4-yl)propionic acid hydrochloride are obtained with a yield of 39%.

11-2 N—[(R)-1-(4-Methoxybenzyl)-2-oxo-2-(3-pentyl-3-phenylazetidin-1-yl)ethyl]-3-(3-methyl-3H-imidazol-4-yl)propionamide 0.17 ml (1.23 mmol) of triethylamine is carefully added to a solution containing 87 mg (0.45 mmol) of 3-(3-methyl-1H-imidazol-4-yl)propionic acid hydrochloride and 160 mg (0.49 mmol) of TBTU in 1 ml of DMF. After stirring for 60 minutes at ambient temperature, 200 mg (0.32 mmol) of (R)-2-amino-3-(4-methoxyphenyl)-1-(3-pentyl-3-phenylazetidin-1-yl)propan-1-one trifluoroacetate (cf. procedure 9-3) are added and the reaction medium is left to stir for three days. The reaction medium is treated with a 2 heptane/8 EtOAc mixture and a 1N aqueous solution of sodium hydroxide. The organic phase is dried over MgSO$_4$, filtered and evaporated. The residue obtained is purified by silica chromatography (eluent 9 DCM/1 MeOH). 21 mg of N—[(R)-1-(4-methoxybenzyl)-2-oxo-2-(3-pentyl-3-phenylazetidin-1-yl)ethyl]-3-(3-methyl-3H-imidazol-4-yl)propionamide are obtained with a yield of 9%.

HPLC: (method W); retention time: 18.04 min, 96%, M+H: 517.

EXAMPLE NO. 12

N—[(R)-2-(3-Cyclohexyl-3-pentylazetidin-1-yl)-1-(4-methoxybenzyl)-2-oxoethyl]-3-(1H-imidazol-4-yl)propionamide (compound No. 66; Table I)

12-1 3-Cyclohexyl-3-pentylazetidine oxalate 254 mg of rhodium-on-alumina at 5% are added to 652 mg (2.62 mmol) of 3-pentyl-3-phenylazetidine oxalate (cf.) in 13 ml of water and 6.5 ml of THF. The medium is placed under a hydrogen atmosphere at 6 bar of pressure and heated at 80° C. After 23 hours, the reaction medium is filtered through celite and the solvents are evaporated off. 0.43 g of 3-cyclohexyl-3-pentylazetidine oxalate is obtained with a yield of 64%.

12-2 tert-Butyl [(R)-2-(3-cyclohexyl-3-pentylazetidin-1-yl)-1-(4-methoxybenzyl)-2-oxoethyl]carbamate 0.36 g (1.98 mmol) of EDC, 0.25 g (1.85 mmol) of HOBt and 0.51 g (1.73 mmol) of (R)-2-tert-butoxycarbonylamino-3-(4-methoxyphenyl)propionic acid are added to 0.43 g (1.69 mmol) of 3-cyclohexyl-3-pentylazetidine oxalate dissolved in 8 ml of DMF. After 5 minutes, 0.9 ml (6.5 mmol) of triethylamine is added. After 1 hour 30 minutes, the reaction medium is extracted with a 1/1 EtOAc/heptane mixture and washed with a solution of 1N hydrochloric acid, of 1N sodium hydroxide and of water. The organic phase is dried over MgSO$_4$, filtered and concentrated. The residue is purified on a silica column (eluent 6/4 heptane/EtOAc). 0.48 g of tert-butyl [(R)-2-(3-cyclohexyl-3-pentylazetidin-1-yl)-1-(4-methoxybenzyl)-2-oxoethyl]carbamate in the form of a colourless oil is obtained with a yield of 59%.

12-3 (R)-2-Amino-1-(3-cyclohexyl-3-pentylazetidin-1-yl)-3-(4-methoxyphenyl)propan-1-one 2.5 ml of trifluoroacetic acid are added, at 0° C., to 0.48 g (0.99 mmol) of tert-butyl [(R)-2-(3-cyclohexyl-3-pentylazetidin-1-yl)-1-(4-methoxybenzyl)-2-oxoethyl]carbamate dissolved in 10 ml of dichloromethane. After 2 hours, the solvents are evaporated off. The residue is taken up in dichloromethane and washed with 1N sodium hydroxide. The organic phases are combined, dried over MgSO$_4$, filtered and concentrated. 327 mg of (R)-2-amino-1-(3-cyclohexyl-3-pentylazetidin-1-yl)-3-(4-methoxyphen-yl)propan-1-one are obtained with a yield of 86%.

12-4 N—[(R)-2-(3-Cyclohexyl-3-pentylazetidin-1-yl)-1-(4-methoxybenzyl)-2-oxoethyl]-3-(1H-imidazol-4-yl)propionamide 100 mg (0.311 mmol) of TBTU and 0.1 ml (0.715 mmol) of triethylamine are added to 55 mg (0.311 mmol) of 3-(1H-imidazol-4-yl)propionic acid hydrochloride in 1 ml of DMF. After 10 minutes, 99 mg (0.256 mmol) of (R)-2-amino-1-(3-cyclohexyl-3-pentylazetidin-1-yl)-3-(4-methoxyphenyl)propan-1-one dissolved in 1 ml of DMF are added. After stirring for 118 hours at ambient temperature, the reaction medium is extracted with a 1/2 heptane/EtOAc mixture and washed with 1N sodium hydroxide and a saturated sodium chloride solution. The organic phase is dried over MgSO$_4$, filtered and concentrated. The residue is purified on a silica column (eluent 9/1 DCM/MeOH). 72 mg of N—[(R)-2-(3-cyclohexyl-3-pentylazetidin-1-yl)-1-(4-methoxybenzyl)-2-oxoethyl]-3-(1H-imidazol-4-yl)propionamide are obtained in the form of a white powder, with a yield of 55%.

HPLC: (method Y); retention time: 18.34 min, 98%, M+H: 509.

EXAMPLE 13

N—[(R)-2-[3-butoxy-3-(2-fluorophenyl)-azetidin-1-yl]-1-(4-methoxybenzyl)-2-oxoethyl]-3-(1H-imidazol-4-yl)propionamide

13.1: 3-(2-Fluorophenyl)-3-hydroxy-1-(tert-butoxycarbonyl)azetidine 3.1 ml (6.1 mmol) of a 2M solution of isopropylmagnesium chloride in tetrahydrofuran are added to a solution of 1.1 g (6.2 mmol) of 1-bromo-2-fluorobenzene in 4 ml of tetrahydrofuran, cooled beforehand to −25° C. After stirring for 30 minutes at −25° C., a solution of 0.65 g (3.7 mmol) of 3-oxo-1-(tert-butoxycarbonyl)azetidine in 7.5 ml of tetrahydrofuran is added. The reaction medium is stirred for 30 min and then a saturated aqueous solution of ammonium chloride is added. The organic compounds are extracted with a 1/1 heptane/ethyl acetate mixture. The organic phase is dried over magnesium sulphate and then filtered and evaporated. The crude product is purified by silica gel chromatography, elution being carried out with a 5/5 heptane/ethyl acetate mixture. 135 mg of 3-(2-fluorophenyl)-3-hydroxy-1-(tert-butoxycarbonyl)-azetidine are obtained in the form of a white solid with a yield of 14%.

13.2: 3-Butoxy-3-(2-fluorophenyl)-1-(tert-butoxycarbonyl)azetidine 135 mg (0.4 mmol) of 3-(2-fluorophenyl)-3-hydroxy-1-(tert-butoxycarbonyl)azetidine at 80% in 2 ml of dimethylformamide are added to a suspension of 65 mg (1.6 mmol) of sodium hydride at 60% in 1.5 ml of dimethylformamide, under nitrogen, at 0° C. After stirring for 20 minutes at 0° C., 0.2 ml (1.5 mmol) of iodobutane are added. The reaction medium is stirred at ambient temperature for 1 h 30 and is then hydrolysed with water and with a saturated aqueous solution of ammonium chloride and extracted with a 1/2 heptane/ethyl acetate mixture. The organic phases are combined, washed with water, dried over magnesium sulphate, filtered and evaporated. The crude product is purified by silica gel chromatography, elution being carried out with an 8/2 heptane/ethyl acetate mixture. 104 mg of 3-butoxy-3-(2-fluorophenyl)-1-(tert-butoxycarbonyl)azetidine are obtained in the form of a yellow oil with a yield of 79%.

13.3: 3-Butoxy-3-(2-fluorophenyl)azetidine trifluoroacetate 1 ml of trifluoroacetic acid is added to a solution containing 104 mg (0.3 mmol) of 3-butoxy-3-(2-fluorophenyl)-1-(tert-butoxycarbonyl)azetidine in 3 ml of dichloromethane at 0° C. After stirring for 30 minutes, the reaction medium is evaporated off under a stream of nitrogen. 126 mg of 3-butoxy-3-(2-fluorophenyl)azetidine trifluoroacetate are obtained in the form of a pale yellow oil with a yield of 100%.

13.4: tert-Butyl [(R)-2-[3-butoxy-3-(2-fluorophenyl)-azetidin-1-yl]-1-(4-methoxybenzyl)-2-oxoethyl]carbamate 68 mg of EDC (0.3 mmol), 45 mg (0.3 mmol) of HOBt and 100 mg (0.33 mmol) of Boc-D-methoxyphenylalanine are added successively to 126 mg (0.3 mmol) of 3-butoxy-3-(2-fluorophenyl)azetidine trifluoroacetate in 1.5 ml of dimethylformamide under nitrogen. After stirring for 5 minutes, 0.2 ml (1.3 mmol) of triethylamine is added. The reaction medium is then stirred for 23 hours at ambient temperature and extracted with a 1/1 ethyl acetate/heptane mixture in the presence of a 1N aqueous solution of sodium hydroxide. The organic phase is washed with a 1N aqueous solution of hydrochloric acid and then with water, dried over magnesium sulphate, filtered and evaporated. 94 mg of tert-butyl [(R)-2-[3-butoxy-3-(2-fluorophenyl)azetidin-1-yl]-1-(4-methoxybenzyl)-2-oxoethyl]carbamate are obtained in the form of a yellow oil with a yield of 58%.

13.5: (R)-2-Amino-1-[3-butoxy-3-(2-fluorophenyl)-azetidin-1-yl]-3-(4-methoxyphenyl)propan-1-one trifluoroacetate 1 ml of trifluoroacetic acid is added to a solution of 94 mg (0.2 mmol) of tert-butyl [(R)-2-[3-butoxy-3-(2-fluorophenyl)azetidin-1-yl]-1-(4-methoxybenzyl)-2-oxoethyl]carbamate in 10 ml of dichloromethane, cooled beforehand to 0° C. After stirring for 1 h 30 at ambient temperature, the reaction medium is evaporated off under a stream of nitrogen. 119 mg of (R)-2-amino-1-[3-butoxy-3-(2-fluorophenyl)azetidin-1-yl]-3-(4-methoxyphenyl)propan-1-one trifluoroacetate are obtained in the form of a yellow oil with a yield of 100%.

13.6: N—[(R)-2-[3-Butoxy-3-(2-fluorophenyl)azetidin-1-yl]-1-(4-methoxybenzyl)-2-oxoethyl]-3-(1H-imidazol-4-yl)propionamide 81 mg (0.3 mmol) of TBTU and 0.1 ml (0.6 mmol) of triethylamine are added to a solution of 42 mg (0.25 mmol) of desamino-histidine hydrochloride in 1 ml of dimethylformamide. After stirring for 10 minutes, 119 mg (0.2 mmol) of (R)-2-amino-1-[3-butoxy-3-(2-fluorophenyl)azetidin-1-yl]-3-(4-methoxyphenyl)propan-1-one trifluoroacetate are added and the reaction medium is stirred for 64 h at ambient temperature. After extraction with a 1/2 heptane/ethyl acetate mixture, the organic phase is washed with 1N aqueous solution of sodium hydroxide and a saturated aqueous solution of sodium chloride, dried over magnesium sulphate, filtered and evaporated. The crude product is purified by silica gel chromatography, elution being carried out with a 90/10 dichloromethane/methanol mixture. 59 mg of N—[(R)-2-[3-butoxy-3-(2-fluoro-phenyl)azetidin-1-yl]-1-(4-methoxybenzyl)-2-oxoethyl]-3-(1H-imidazol-4-yl)propionamide are obtained in the form of a white solid with a yield of 57%.

$^1$H NMR/DMSO d$^6$ 100° C.: δ=0.78 (t, J=7.2-7.6 Hz, 3H); 1.23 (sext, J=6.8-7.2 Hz, 2H); 1.37 (quint, J=6.4-7.6 Hz, 2H); 2.38-2.42 (m, 2H); 2.68-2.94 (m, 7H); 3.10 (bt, J=5.6-6.4, 2H); 4.00-4.40 (m, 4H); 4.50 (q, J=7.2-7.6 Hz, 1H); 6.67-6.80 (m, 3H); 7.09-7.24 (m, 4H); 7.30-7.43 (m, 4H); 7.70-7.90 (m, 1H).

EXAMPLE 14

N—[(R)-2-(3-Butoxy-3-o-tolylazetidin-1-yl)-1-(4-methoxybenzyl)-2-oxoethyl]-3-(1-methyl-1H-imidazol-4-yl)propionamide

14.1 Methyl (E)-3-(1-methyl-1H-imidazol-4-yl)acrylate 1 ml (5.5 mmol) of methyl diethylphosphonoacetate are added to a suspension of 220 mg (5.5 mmol) of sodium hydride at 60% in 5 ml of tetrahydrofuran cooled to 0° C.

After stirring for 1 h, 500 mg (4.5 mmol) of 1-methyl-1H-imidazole-4-carbaldehyde are added and the mixture is stirred for 4 hours at ambient temperature and then hydrolysed with water and extracted with ethyl acetate. The organic phase is washed with a saturated aqueous solution of sodium hydrogen carbonate, dried over magnesium sulphate, filtered and evaporated. The product obtained is precipitated from heptane and filtered. 430 mg of methyl (E)-3-(1-methyl-1H-imidazol-4-yl)acrylate are obtained in the form of a yellow powder with a yield of 57%.

14.2 3-(1-Methyl-1H-imidazol-4-yl)propanoic acid hydrochloride 50 mg of palladium-on-charcoal at 10% are added to a solution of 100 mg (0.6 mmol) of methyl (E)-3-(1-methyl-1H-imidazol-4-yl)acrylate in 5 ml of a 1N aqueous solution of sodium hydroxide. The reaction medium is flushed with nitrogen and then stirred under a hydrogen atmosphere for 24 h. After filtration through celite, the filtrate is brought back to pH 2 with a concentrated aqueous solution of hydrochloric acid, toluene is added, and the medium is concentrated to dryness. The residue obtained is taken up in acetone and the precipitated salts are filtered off. The filtrate is concentrated. 160 mg of 3-(1-methyl-1H-imidazol-4-yl)propanoic acid hydrochloride are obtained in the form of a solid with a yield of 32%.

14.3 N—[(R)-2-(3-Butoxy-3-o-tolylazetidin-1-yl)-1-(4-methoxybenzyl)-2-oxoethyl]-3-(1-methyl-1H-imidazol-4-yl)propionamide 84 mg (0.3 mmol) of TBTU and 0.1 ml (0.5 mmol) of triethylamine are added to a solution of 50 mg (0.3 mmol) of 3-(1-methyl-1H-imidazol-4-yl)propanoic acid hydrochloride in 2 ml of dimethylformamide. After stirring for 1 h at ambient temperature, 90 mg (0.2 mmol) of (R)-2-amino-1-(3-butoxy-3-o-tolylazetidin-1-yl)-3-(4-methoxyphenyl)propan-1-one hydrochloride (prepared as described in Example 6.2) are added. The reaction medium is stirred at ambient temperature for 72 h, extracted with a 2/8 heptane/ethyl acetate mixture and then washed with a 1N aqueous solution of sodium hydroxide. The organic phase is dried over magnesium sulphate, filtered and evaporated.

The crude product is purified by silica gel chromatography, elution being carried out with a 97/3 dichloromethane/methanol mixture. 22 mg of N—[(R)-2-(3-butoxy-3-o-tolylazetidin-1-yl)-1-(4-methoxybenzyl)-2-oxoethyl]-3-(1-methyl-1H-imidazol-4-yl)propionamide are obtained in the form of a beige powder with a yield of 23%.

HPLC: (Method U); retention time: 15.28 min, 96.5%, M+H: 533

EXAMPLE 15

N-[2-(3-Butoxy-3-o-tolylazetidin-1-yl)-1-(2-hydroxy-4-methoxybenzyl)-2-oxoethyl]-3-(3H-imidazol-4-yl)propionamide trifluoroacetate 15.1: 2-Benzyloxy-4-methoxybenzaldehyde 160 ml (1.3 mmol) of benzyl bromide and (1.3 mmol) of potassium carbonate are added to a solution of 2 g (1.3 mmol) of 2-hydroxy-4-methoxybenzaldehyde in 20 ml of acetone. The mixture is stirred at reflux for 6 hours and then evaporated. 50 ml of 1N aqueous solution of sodium hydroxide are added and the medium is extracted with dichloromethane. The organic phase is dried over magnesium sulphate, filtered and evaporated. The residue obtained is precipitated from 1 heptane/ethyl acetate mixture (95/5). 2.75 g of 2-benzyloxy-4-methoxybenzaldehyde are obtained in the form of a white powder with a yield of 86%.

15.2: Methyl (E)-3-(2-benzyloxy-4-methoxyphenyl)-2-(tert-butoxycarbonyl)aminoacrylate 1.8 g (5.4 mmol) of 1,8-diazabicyclo[5.4.0]undec-7-ene are added to a solution of 1.8 g (6.2 mmol) of (±)-Boc-α-phosphonoglycine trimethyl ester in 10 ml of dichloromethane, cooled beforehand to 0° C. The mixture is stirred for 10 minutes at 0° C. and then a solution of 1 g (4.1 mmol) of 2-benzyloxy-4-methoxybenzaldehyde in 5 ml of dichloromethane is added and the reaction medium is then stirred for 18 h at ambient temperature. After the dichloromethane has been evaporated off, the residue is taken up in 50 ml of ethyl acetate. The organic phase is washed with a saturated aqueous solution of ammonium chloride, and water, dried over magnesium sulphate, filtered and evaporated. The residue obtained is purified by silica gel chromatography (eluent: 70/30 heptane/ethyl acetate). 1.5 g of methyl (E)-3-(2-benzyloxy-4-methoxyphenyl)-2-(tert-butoxycarbonylamino)acrylate are obtained in the form of a beige powder with a yield of 85%.

15.3: Methyl 2-tert-butoxycarbonylamino-3-(2-hydroxy-4-methoxyphenyl)propanoate 350 mg of palladium-on-charcoal at 10% are added to a solution containing 1.5 g (3.5 mmol) of methyl (E)-3-(2-benzyloxy-4-methoxyphenyl)-2-(tert-butoxycarbonylamino)acrylate in 15 ml of methanol. After stirring for hours under a hydrogen atmosphere, the reaction medium is filtered through celite and the filtrate is evaporated off. 850 mg of methyl 2-tert-butoxycarbonylamino-3-(2-hydroxy-4-methoxyphenyl)-propanoate are obtained in the form of a grey powder with a yield of 74%.

15.4: 2-tert-Butoxycarbonylamino-3-(2-hydroxy-4-methoxyphenyl)propanoic acid 5 ml of a 1N aqueous solution of sodium hydroxide are added to a solution of 850 mg (2.6 mmol) of methyl 2-tert-butoxycarbonylamino-3-(2-hydroxy-4-methoxyphenyl)-propanoate in 10 ml of tetrahydrofuran. The reaction medium is stirred for 4 hours at ambient temperature and then a 1N aqueous solution of hydrochloric acid is added until the pH is 1, and the medium is extracted with dichloromethane. The organic phase is dried over magnesium sulphate, filtered and evaporated. 820 mg of 2-tert-butoxycarbonylamino-3-(2-hydroxy-4-methoxyphenyl)propanoic acid are obtained in the form of a beige powder with a quantitative yield.

15.5: 3-butoxy-3-o-tolylazetidine trifluoroacetate 1 ml of trifluoroacetic acid is added to a solution containing 500 mg (1.65 mmol) of 3-butoxy-3-o-tolylazetidine-1-(tert-butoxycarbonyl)azetidine dissolved in 5 ml of dichloromethane. The reaction medium is stirred at ambient temperature for 3 hours and then concentrated. The crude product obtained is purified by silica gel chromatography (eluent: 90/10 dichloromethane/methanol). 400 mg in the form of a pale yellow powder are obtained with a yield of 76%.

15.6: tert-Butyl [2-(3-butoxy-3-o-tolylazetidin-1-yl)-1-(2-hydroxy-4-methoxybenzyl)-2-oxoethyl]carbamate 74 mg (0.4 mmol) of EDC and 52 mg (0.4 mmol) of HOBt are added to a solution of 100 mg (0.3 mmol) of 2-tert-butoxycarbonylamino-3-(2-hydroxy-4-methoxyphenyl)-propanoic acid in 5 ml of dimethylformamide. The mixture is stirred for 15 min and 107 mg (0.3 mmol) of 3-butoxy-3-o-tolylazetidine trifluoroacetate are added. After stirring for a further 15 minutes at ambient temperature, 0.3 ml (1.3 mmol) of diisopropylethylamine is added. The reaction medium is stirred for 2 h, and then 10 ml of a 1N aqueous solution of hydrochloric acid are added and the medium is extracted with ethyl acetate. The organic phase is washed with water and then dried over magnesium sulphate, filtered and evaporated. The residue is filtered through silica gel (eluent: 70/30 heptane/ethyl acetate). 220 mg of tert-butyl [2-(3-butoxy-3-o-tolylazetidin-1-yl)-1-(2-hydroxy-4-methoxybenzyl)-2-oxoethyl]carbamate are obtained in the form of a yellow oil and are used crude in the next stage.

15.7: 2-Amino-1-(3-butoxy-3-o-tolylazetidin-1-yl)-3-(2-hydroxy-4-methoxyphenyl)propan-1-one trifluoroacetate 1 ml of trifluoroacetic acid is added to 220 mg (0.4 mmol) of tert-butyl [2-(3-butoxy-3-o-tolylazetidin-1-yl)-1-(2-hydroxy-4-methoxybenzyl)-2-oxoethyl]carbamate in 2 ml of dichloromethane. After stirring for 1 hour at ambient temperature, the reaction medium is concentrated under vacuum. 250 mg of 2-amino-1-(3-butoxy-3-o-tolylazetidin-1-yl)-3-(2-hydroxy-4-methoxyphenyl)propan-1-one trifluoroacetate are obtained in the form of a yellow oil with a quantitative yield.

15.8: N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate 0.25 ml (0.6 mmol) of triethylamine is added to a solution of 90 mg (0.6 mmol) of desamino-histidine and 207 mg (0.6 mmol) of TBTU in 2 ml of dimethylformamide. After stirring for 1 h at ambient temperature, 250 mg (0.4 mmol) of 2-amino-1-(3-butoxy-3-o-tolylazetidin-1-yl)-3-(3-hydroxy-4-methoxyphenyl)propan-1-one trifluoroacetate are added and the mixture is stirred for 72 h at ambient temperature. 10 ml of a saturated aqueous solution of sodium hydrogen carbonate are then poured into the reaction medium, which is extracted with a 20/80 heptane/ethyl acetate mixture. The organic phase is dried over magnesium sulphate, filtered and concentrated. The product is purified by preparative thin layer chromatography (eluent: 90/10 dichloro-methane/methanol). 30 mg of N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate are obtained in the form of a beige powder with a yield of 11%.

HPLC: (Method A1): retention time: 14.39 min, 94.2%, M+H: 535.

EXAMPLE 16

(S)—N—[(R)-2-(3-Butoxy-3-o-tolylazetidin-1-yl)-1-(4-methoxybenzyl)-2-oxoethyl]-2-hydroxy-3-(1H-imidazol-4-yl)propionamide 0.1 ml (0.8 mmol) of triethylamine is added to a solution containing 50 mg (0.3 mmol) of (S)-2-hydroxy-3-(1H-imidazol-4-yl)propanoic acid and 100 mg (0.3 mmol) of TBTU in 2 ml of dimethylformamide. After stirring for 1 hour at ambient temperature, 128 mg (0.3 mmol) of (R)-2-amino-1-(3-butoxy-3-o-tolylazetidin-1-yl)-3-(4-methoxyphenyl)propan-1-one hydrochloride (described in Example 6.2) are added and the mixture is stirred for 72 h at ambient temperature. A 1N aqueous solution of sodium hydroxide is added and the medium is extracted with a 20/80 heptane/ethyl acetate mixture. The organic phase is dried over magnesium sulphate, filtered and concentrated. The crude product is purified by preparative thin layer chromatography (eluent: 90/10 dichloro-methane/methanol). 17 mg of (S)—N—[(R)-2-(3-butoxy-3-o-tolylazetidin-1-yl)-1-(4-methoxybenzyl)-2-oxoethyl]-2-hydroxy-3-(1H-imidazol-4-yl)propionamide are obtained in the form of a white powder with a yield of 13%.

$^1$H NMR/DMSO d$^6$ 100° C.: δ=0.78 (t, J=7.2 Hz, 3H); 1.23 (sext, J=7.3 Hz, 2H); 1.36 (quint, J=6.7 Hz, 2H); 2.12 (s, 3H); 2.55-2.75 (m, 1H); 2.86-2.98 (m, 7H); 3.68 (bs, 3H); 3.90-4.30 (m, 4H); 4.54 (bq, J=6.4 Hz, 1H); 5.25-5.45 (m, 1H); 6.55-6.95 (m, 3H); 7.09-7.27 (m, 6H); 7.43 (bs, 1H); 7.50-7.65 (m, 1H).

EXAMPLE 17

N-[2-(3-Butoxy-3-o-tolylazetidin-1-yl)-1-(4-hydroxybenzyl)-2-oxoethyl]-3-(3H-imidazol-4-yl)-propionamide

17.1: tert-Butyl [2-(3-butoxy-3-o-tolylazetidin-1-yl)-1-(4-hydroxybenzyl)-2-oxoethyl]carbamate 205 mg (1.1 mmol) of EDC and then 145 mg (1.1 mmol) of HOBt are added to a solution of 250 mg (0.9 mmol) of (R)-2-tert-butoxycarbonylamino-3-(4-hydroxyphenyl)-propanoic acid in 5 ml of dimethylformamide. After stirring for 15 minutes at ambient temperature, 300 mg (1.1 mmol) of 3-butoxy-3-o-tolylazetidine trifluoroacetate (described in Example 15.5) and 0.5 ml (3.6 mmol) of triethylamine are added. The reaction medium is stirred for 2 h at ambient temperature and then a 1N aqueous solution of hydrochloric acid is added and the mixture is extracted with ethyl acetate. The organic phase is washed with water, and then dried over magnesium sulphate, filtered and evaporated. The residue is purified by silica gel chromatography, elution being carried out with a 60/40 heptane/ethyl acetate mixture. 410 mg of [2-(3-butoxy-3-o-tolylazetidin-1-yl)-1-(4-hydroxybenzyl)-2-oxoethyl]-3-(3H-imidazol-4-yl)propionamide are obtained with a yield of 90%.

17.2: 2-Amino-1-(3-butoxy-3-o-tolylazetidin-1-yl)-3-(4-hydroxyphenyl)propan-1-one trifluoroacetate 2 ml of trifluoroacetic acid are added to a solution of 410 mg (0.8 mmol) of tert-butyl [2-(3-butoxy-3-o-tolylazetidin-1-yl)-1-(4-hydroxybenzyl)-2-oxoethyl]carbamate in 5 ml of dichloromethane. After stirring for 1 hour at ambient temperature, the solvent is evaporated off. 440 mg of 2-amino-1-(3-butoxy-3-o-tolylazetidin-1-yl)-3-(4-hydroxyphenyl)propan-1-one trifluoroacetate are obtained with a quantitative yield.

17.3: N-[2-(3-Butoxy-3-o-tolylazetidin-1-yl)-1-(4-hydroxybenzyl)-2-oxoethyl]-3-(3H-imidazol-4-yl)propionamide 0.35 ml (2.6 mmol) of triethylamine are added to a solution containing 225 mg (1.3 mmol) of desamino-histidine hydrochloride and 410 mg (1.3 mmol) of TBTU in 5 ml of DMF. After stirring for 1 hour at ambient temperature, 440 mg (0.9 mmol) of 2-amino-1-(3-butoxy-3-o-tolylazetidin-1-yl)-3-(4-hydroxyphenyl)propan-1-one trifluoroacetate are added. After stirring for 72 h at ambient temperature, the reaction medium is treated with a saturated aqueous solution of sodium hydrogen carbonate and then extracted with a 20/80 heptane/ethyl acetate mixture. The organic phase is dried over magnesium sulphate, filtered and concentrated. The product is purified by preparative thin layer chromatography (eluent: 90/10 dichloro-methane/methanol). 205 mg of N-[2-(3-butoxy-3-o-tolylazetidin-1-yl)-1-(4-hydroxybenzyl)-2-oxoethyl]-3-(3H-imidazol-4-yl)propionamide are obtained in the form of a white powder with a yield of 47%.

$^1$H NMR/DMSO d$^6$ 100° C.: δ=0.80 (t, J=7.6 Hz, 3H,); 1.22 (m, 2H); 1.36 (quint, J=6.4 Hz, 2H,); 2.23 (s, 3H); 2.40 (t, J=8.8 Hz, 2H); 2.82-2.70 (m, 4H); 2.97 (t, J=6.4 Hz, 2H); 4.09 (d, J=10 Hz, 2H); 4.23 (d, J=7.6 Hz, 2H); 4.50 (q, J=7.6 Hz, 1H); 6.63 (m, 2H); 6.70 (s, 1H); 6.99 (m, 2H); 7.26-7.20 (m, 4H); 7.49 (s, 1H); 7.75 (s, 1H).

EXAMPLE 18

N-[1-(3-Butoxy-3-o-tolylazetidine-1-carbonyl)-2-hydroxy-2-(4-methoxyphenyl)ethyl]-3-(1H-imidazol-4-yl)propionamide 18.1: Ethyl 2-amino-3-(4-methoxyphenyl)-3-oxopropanoate hydrochloride 5 g (18.6 mmol) of ethyl N-(diphenylmethylene)glycinate in solution in 20 ml of tetrahydrofuran are added to a solution of 18.7 ml (18.6 mmol) of 1N potassium tert-butoxide in 20 ml of tetrahydrofuran cooled to −70° C. After stirring for 30 minutes, this mixture is added to a solution containing 3.2 g (18.6 mmol) of 4-methoxybenzoyl chloride in 20 ml of tetrahydrofuran at −70° C. One hour after the addition, the reaction medium is hydrolysed with a 1N aqueous solution of hydrochloric acid and concentrated. The residue is taken up in water and extracted with diethyl ether. The organic phase is dried over magnesium sulphate and the solvent is then evaporated off. 5.5 g of ethyl 2-amino-3-(4-methoxyphenyl)-3-oxopropanoate hydrochloride are obtained with a quantitative yield.

18.2: Ethyl 2-tert-butoxycarbonylamino-3-(4-methoxyphenyl)-3-oxopropanoate 4 g (18.3 mmol) of di-tert-butyl dicarbonate and 2.6 ml (18.3 mmol) of triethylamine are added to 5 g (18.3 mmol) of ethyl 2-amino-3-(4-methoxyphenyl)-3-oxopropanoate hydrochloride dissolved in 60 ml of tetrahydrofuran at 0° C. After stirring for 3 hours at ambient temperature, the mixture is treated with water and extracted with ethyl acetate. The organic phase is washed with a 1N aqueous solution of sodium hydrogen sulphate, and water and then dried over magnesium sulphate, filtered and concentrated. 4.1 g of ethyl 2-tert-butoxycarbonylamino-3-(4-methoxyphenyl)-3-oxopropanoate are obtained in the form of a yellow oil with a yield of 66%.

18.3: Ethyl 2-tert-butoxycarbonylamino-3-hydroxy-3-(4-methoxyphenyl)propanoate 461 mg (0.7 mmol) of sodium borohydride are carefully added to a solution of 4.1 mg (12.2 mmol) of ethyl 2-tert-butoxycarbonylamino-3-(4-methoxyphenyl)-3-oxopropanoate in 40 ml of ethanol cooled to −78° C. After stirring for 15 minutes, the reaction medium is hydrolysed with a saturated aqueous solution of ammonium chloride. The ethanol is evaporated off and the aqueous phase is extracted with dichloromethane. The organic phase is dried over magnesium sulphate, filtered and concentrated. The residue is purified by silica gel chromatography, elution being carried out with a 70/30 heptane/ethyl acetate mixture. 3 g of ethyl 2-tert-butoxycarbonylamino-3-hydroxy-3-(4-methoxyphenyl)propanoate are obtained in the form of a yellow oil with a yield of 72%.

18.4: 2-tert-Butoxycarbonylamino-3-hydroxy-3-(4-methoxyphenyl)propanoic acid 15 ml of a 1N aqueous solution of sodium hydroxide are added to a solution containing 3 g (8.4 mmol) of 2-tert-butoxycarbonylamino-3-hydroxy-3-(4-methoxyphenyl)-propanoic acid in 40 ml of tetrahydrofuran. The mixture is stirred for 4 hours at ambient temperature, treated with a 1N aqueous solution of hydrochloric acid until the pH is 1, and then extracted with dichloromethane. The organic phase is dried over magnesium sulphate, filtered and concentrated. The residue is precipitated from a 1/1 diethyl ether/heptane mixture. 2.2 g of 2-tert-butoxycarbonylamino-3-hydroxy-3-(4-methoxyphenyl)-propanoic acid are obtained in the form of a white powder with a yield of 84%.

18.5: tert-Butyl [1-(3-butoxy-3-o-tolylazetidine-1-carbonyl)-2-hydroxy-2-(4-methoxyphenyl)ethyl]carbamate 740 mg (3.5 mmol) of EDC and 1.2 g (9.6 mmol) of 4-dimethylaminopyridine are added to a solution of 1 g (3.2 mmol) of 2-tert-butoxycarbonylamino-3-hydroxy-3-(4-methoxyphenyl)propanoic acid, 1.1 g (3.5 mmol) of 3-butoxy-3-o-tolylazetidine trifluoroacetate and 480 mg (3.5 mmol) of HOAT in 10 ml of dichloromethane cooled to 0° C. After stirring for 24 hours at ambient temperature, the reaction medium is treated with a 1N aqueous solution of sodium hydroxide and then extracted with ethyl acetate. The organic phase is washed successively with a 1N aqueous solution of hydrochloric acid and water, and then dried over magnesium sulphate, filtered and concentrated. The residue obtained is purified by silica gel chromatography (eluent: 60/40 heptane/ethyl acetate). 1.4 g of tert-butyl [1-(3-butoxy-3-o-tolylazetidine-1-carbonyl)-2-hydroxy-2-(4-methoxyphenyl)ethyl]carbamate are obtained in the form of a colourless oil with a yield of 87%.

18.6: 2-Amino-1-(3-butoxy-3-o-tolylazetidin-1-yl)-3-hydroxy-3-(4-methoxyphenyl)propan-1-one trifluoroacetate 10 ml of trifluoroacetic acid are added to a solution containing 1.4 g (2.8 mmol) of tert-butyl [1-(3-butoxy-3-o-tolylazetidine-1-carbonyl)-2-hydroxy-2-(4-methoxyphenyl) ethyl]carbamate in 20 ml of dichloromethane. After stirring for 1 hour at ambient temperature, the reaction medium is concentrated. 1.5 g of 2-amino-1-(3-butoxy-3-o-tolylazetidin-1-yl)-3-hydroxy-3-(4-methoxyphenyl)propan-1-one trifluoroacetate are obtained in the form of a beige powder with a quantitative yield.

18.7: N-[1-(3-Butoxy-3-o-tolylazetidine-1-carbonyl)-2-hydroxy-2-(4-methoxyphenyl)ethyl]-3-(1H-imidazol-4-yl)propionamide 0.2 ml (1.5 mmol) of triethylamine is added to a solution containing 100 mg (0.6 mmol) of desamino-histidine hydrochloride and 180 mg (0.6 mmol) of TBTU in 5 ml of dimethylformamide. After stirring for 1 h at ambient temperature, 200 mg (0.4 mmol) of 2-amino-1-(3-butoxy-3-o-tolylazetidin-1-yl)-3-hydroxy-3-(4-methoxyphenyl)propan-1-one trifluoroacetate are added. The reaction medium is stirred for 48 h at ambient temperature and then treated with a 1N aqueous solution of sodium hydroxide and extracted with a 20/80 heptane/ethyl acetate mixture. The organic phase is dried over magnesium sulphate, filtered and concentrated. The residue is purified by preparative thin layer chromatography (eluent: 90/10 dichloromethane/methanol). 80 mg of N-[1-(3-butoxy-3-o-tolylazetidine-1-carbonyl)-2-hydroxy-2-(4-methoxyphenyl)ethyl]-3-(1H-imidazol-4-yl)propionamide are obtained in the form of a beige powder with a yield of 39%.

$^1$H NMR/DMSO d$^6$ 100° C.: δ=0.78 (t, J=7.6 Hz, 3H); 1.23 (sext, J=7.3 Hz, 2H); 1.37 (quint, J=6.7 Hz, 2H); 2.25 (s, 3H); 2.40-2.50 (m, 2H); 2.75 (m, 2H); 3.01 (t, J=12 Hz, 2H); 3.70-3.80 (bs, 3H); 4.10-4.50 (m, 6H); 4.55 (m, 1H); 4.73 (m, 1H); 6.82 (m, 2H); 7.10-7.40 (m, 8H); 7.86 (m, 1H).

EXAMPLE 19

N—[(R)-2-(3-Butoxy-3-o-tolylazetidin-1-yl)-1-(4-methoxybenzyl)-2-oxoethyl]-3-hydroxy-3-(1H-imidazol-4-yl)propionamide 19.1: tert-Butyl 3-hydroxy-3-(1-trityl-1H-imidazol-4-yl)propanoate 2.15 ml (14.5 mmol) of tert-butyl bromoacetate are added dropwise to a solution of 1 g (15.3 mmol) of zinc 20 mesh in 20 ml of tetrahydrofuran, stirred for 15 min with a few drops of trimethylsilane chloride. After stirring for 15 minutes at ambient temperature, the temperature of the mixture is kept at 50° C. for 1 hour. After a return to ambient temperature, a solution containing 1.2 g (3.6 mmol) of 1-trityl-1H-imidazole-4-carbaldehyde in 10 ml of THF is added. The reaction medium is stirred for 6 h at ambient temperature, and then treated with a 1N aqueous solution of hydrochloric acid and extracted with ethyl acetate. The organic phase is washed successively with a saturated aqueous solution of sodium hydrogen carbonate and then with water. After drying over magnesium sulphate and filtration, the solvent is evaporated off. The residue obtained is precipitated from diisopropyl ether and filtered off. 1.4 g of tert-butyl 3-hydroxy-3-(1-trityl-1H-imidazol-4-yl)propanoate are obtained in the form of a white powder with a yield of 84%.

19.2: 3-Hydroxy-3-(1H-imidazol-4-yl)propanoic acid 3 ml of trifluoroacetic acid are added to a solution of 1.4 g (3 mmol) of tert-butyl 3-hydroxy-3-(1-trityl-1H-imidazol-4-yl)propanoate in 7 ml of dichloromethane. After stirring for 4 hours at ambient temperature, the reaction medium is concentrated. 0.5 g of crude product is used directly in the next stage.

19.3: N—[(R)-2-(3-Butoxy-3-o-tolylazetidin-1-yl)-1-(4-methoxybenzyl)-2-oxoethyl]-3-hydroxy-3-(1H-imidazol-4-yl)propionamide 0.5 ml (3 mmol) of triethylamine are added to a solution containing 0.5 g (3 mmol) of 3-hydroxy-3-(1H-imidazol-4-yl)propanoic acid and 1.0 g (3 mmol) of TBTU in 2 ml of dimethylformamide. After stirring for 1 h at ambient temperature, 1.5 g (3 mmol) of (R)-2-amino-1-(3-butoxy-3-o-tolylazetidin-1-yl)-3-(4-methoxyphenyl)-propan-1-one hydrochloride (prepared as described in Example 6.2) are added. The reaction medium is stirred for 24 h at ambient temperature, treated with a 1N aqueous solution of sodium hydroxide and extracted with a 20/80 heptane/ethyl acetate mixture. The organic phase is dried over magnesium sulphate, filtered and concentrated. The product is purified by silica gel chromatography, elution being carried out with a 97/3 dichloromethane/methanol mixture. 72 mg of N—[(R)-2-(3-butoxy-3-o-tolylazetidin-1-yl)-1-(4-methoxybenzyl)-2-oxoethyl]-3-hydroxy-3-(1H-imidazol-4-yl)propionamide are obtained in the form of a beige powder with a yield of 5%.

$^1$H NMR/DMSO d$^6$ 100° C.: δ=0.78 (t, J=7.2 Hz, 3H); 1.23 (sext, J=7.3 Hz, 2H); 1.36 (quint, J=6.7 Hz, 2H); 2.21 (s, 3H); 2.55-2.65 (m, 2H); 2.70-2.90 (m, 3H); 2.90-3.00 (m, 2H); 3.68 (bs, 3H); 3.90-4.40 (m, 5H); 4.54 (bq, J=7.2 Hz, 1H); 4.92 (bs, 1H); 6.60-6.80 (m, 3H); 7.00-7.30 (m, 6H); 7.46 (bs, 1H); 7.81 (bs, 1H).

EXAMPLE 20

N—[(R)-2-(3-But-2-ynyloxy-3-o-tolylazetidin-1-yl)-1-(4-methoxybenzyl)-2-oxoethyl]-3-(1H-imidazol-4-yl)propionamide 20.1: tert-Butyl 3-hydroxy-3-o-tolylazetidine-1-carboxylate 60 ml (60 mmol) of 1M ortho-tolylmagnesium chloride in THF are added dropwise to a solution of 7.4 g (43 mmol) of tert-butyl 3-oxoazetidine-1-carboxylate in 60 ml of tetrahydrofuran cooled to −78° C. After stirring for 1 h at ambient temperature, the mixture is hydrolysed with a saturated aqueous solution of ammonium chloride and then extracted with ethyl acetate. The organic phase is dried over sodium sulphate, filtered and concentrated. The beige solid obtained is purified by silica gel chromatography, elution being carried out with a 50/50 heptane/ethyl acetate mixture. 8.9 g of tert-butyl 3-hydroxy-3-o-tolylazetidine-1-carboxylate are obtained in the form of a white solid with a yield of 79%.

20.2: tert-Butyl 3-but-2-ynyloxy-3-o-tolylazetidine-1-carboxylate 1 ml (11.4 mmol) of 1-bromo-2-butyne is added to a suspension of 1.4 g (34.2 mmol) of sodium hydride at 60% in 14 ml of dimethylformamide cooled beforehand to 0° C. After stirring for 1 h, 3 g (11.4 mmol) of tert-butyl 3-hydroxy-3-o-tolylazetidine-1-carboxylate in 20 ml of dimethylformamide are added dropwise and the reaction mixture is then stirred for 1 h 30. After hydrolysis with water and with a saturated aqueous solution of ammonium chloride, the reaction medium is extracted with a 1/1 heptane/ethyl acetate mixture. The organic phase is dried over sodium sulphate, filtered and concentrated. The residue obtained is purified by silica gel chromatography, elution being carried out with a 80/20 heptane/ethyl acetate mixture. 2.9 g of tert-butyl 3-but-2-ynyloxy-3-o-tolylazetidine-1-carboxylate are obtained in the form of a yellow oil with a yield of 81%.

20.3: 3-But-2-ynyloxy-3-o-tolylazetidine hydrochloride 2.8 g (9 mmol) of tert-butyl 3-but-2-ynyloxy-3-o-tolylazetidine-1-carboxylate are solubilised in 40 ml (120 mmol)

of a 3M solution of hydrochloric acid in ethyl acetate. After stirring for 1 hour 30 minutes at ambient temperature, the reaction medium is concentrated under vacuum. 2.2 g of 3-but-2-ynyloxy-3-o-tolylazetidine hydrochloride are obtained in the form of a beige solid with a yield of 96%.

20.4: tert-Butyl [(R)-2-(3-but-2-ynyloxy-3-o-tolylazetidin-1-yl)-1-(4-methoxybenzyl)-2-oxoethyl]carbamate 1.9 g (10.2 mmol) of EDC, 1.4 g (10.2 mmol) of HOBt and 3.8 ml (27.2 mmol) of triethylamine are added to a solution containing 2.7 g (9.2 mmol) of Boc-D-methoxyphenylalanine in 55 ml of dimethylformamide. After stirring for 1 h, a solution of 2.2 g (8.7 mmol) of 3-but-2-ynyloxy-3-o-tolylazetidine hydrochloride in 35 ml of dimethylformamide is added to the mixture. The reaction medium is then stirred for 38 hours at ambient temperature. It is subsequently extracted with a 1/1 heptane/ethyl acetate mixture. The organic phase is washed successively with a 1N aqueous solution of sodium hydroxide and then with a 1N aqueous solution of hydrochloric acid, dried over sodium sulphate, filtered and concentrated. The residue obtained is purified by silica gel chromatography, elution being carried out with a 60/40 heptane/ethyl acetate mixture. 1.8 g of tert-butyl [(R)-2-(3-but-2-ynyloxy-3-o-tolylazetidin-1-yl)-1-(4-methoxybenzyl)-2-oxoethyl]carbamate are obtained in the form of a white solid with a yield of 41%.

20.5: (R)-2-Amino-1-(3-but-2-ynyloxy-3-o-tolylazetidin-1-yl)-3-(4-methoxyphenyl)propan-1-one 1.7 g (3.5 mmol) of tert-butyl [(R)-2-(3-but-2-ynyloxy-3-o-tolylazetidin-1-yl)-1-(4-methoxybenzyl)-2-oxoethyl]carbamate are solubilised in 45 ml (135 mmol) of a 3M solution of hydrochloric acid in ethyl acetate. After stirring for 3 h at ambient temperature, the mixture is concentrated. 1.6 g of (R)-2-amino-1-(3-but-2-ynyloxy-3-o-tolylazetidin-1-yl)-3-(4-methoxyphenyl)-propan-1-one are obtained in the form of a beige solid with a quantitative yield.

20.6: N—[(R)-2-(3-But-2-ynyloxy-3-o-tolylazetidin-1-yl)-1-(4-methoxybenzyl)-2-oxoethyl]-3-(1H-imidazol-4-yl)propionamide 732 mg (2.3 mmol) of TBTU and 1 ml (7 mmol) of triethylamine are added to a solution of 408 mg (2.3 mmol) of desamino-histidine hydrochloride in 6 ml of dimethylformamide. After stirring for 10 min, 751 mg (1.8 mmol) of (R)-2-amino-1-(3-but-2-ynyloxy-3-o-tolylazetidin-1-yl)-3-(4-methoxyphenyl)propan-1-one in 6 ml of dimethylformamide are added. The reaction medium is stirred for 115 hours at ambient temperature and then a 1N aqueous solution of sodium hydroxide is added and the medium is extracted with a 1/1 heptane/ethyl acetate mixture. The organic phase is dried over sodium sulphate, filtered and concentrated. The residue obtained is purified by silica gel chromatography, elution being carried out with a 90/10 dichloro-methane/methanol mixture. 362 mg of N—[(R)-2-(3-but-2-ynyloxy-3-o-tolylazetidin-1-yl)-1-(4-methoxybenzyl)-2-oxoethyl]-3-(1H-imidazol-4-yl)propionamide are obtained in the form of a white solid with a yield of 40%.

$^1$H NMR/DMSO d$^6$ 100° C.: δ=1.74 (bs, 3H); 2.21 (s, 3H); 2.39-2.43 (m, 2H); 2.69-3.10 (m, 4H); 3.68 (m, 5H); 4.10-4.40 (m, 4H); 4.52 (q, J=7.2-8.0 Hz, 1H); 6.67-6.85 (m, 3H); 7.05-7.15 (m, 2H); 7.18-7.29 (m, 4H); 7.41 (s, 1H); 7.75-7.85 (m, 1H).

EXAMPLE 21

N—[(R)-2-(3-But-2-ynyloxy-3-o-tolylazetidin-1-yl)-1-(4-methoxybenzyl)-2-oxoethyl]-3-(5-methyl-1H-imidazol-4-yl)propionamide

21.1: 3-(5-Methyl-1H-imidazol-4-yl)propanoic acid hydrochloride 60 mg of palladium-on-charcoal at 10% are added to a solution of 387 mg (1.1 mmol) of (E)-3-(5-methyl-1H-imidazol-4-yl)acrylic acid hydrochloride in a 1/1 tetrahydrofuran/water mixture. The reaction medium is placed under a hydrogen atmosphere and stirred for 19 h, and then filtered through celite. The filtrate is concentrated under vacuum. The residue obtained is taken up in a heptane/diisopropyl ether mixture with stirring for 2 h. The white precipitate formed is filtered off and then dried. 326 mg of 3-(5-methyl-1H-imidazol-4-yl)propanoic acid hydrochloride are obtained in the form of a white solid with a yield of 83%.

21.2: N—[(R)-2-(3-But-2-ynyloxy-3-o-tolylazetidin-1-yl)-1-(4-methoxybenzyl)-2-oxoethyl]-3-(5-methyl-1H-imidazol-4-yl)propionamide 389 mg (1.2 mmol) of TBTU and 0.5 ml (3.7 mmol) of triethylamine are added to a solution containing 229 mg (1.2 mmol) of 3-(5-methyl-1H-imidazol-4-yl)propanoic acid hydrochloride in 4 ml of dimethylformamide. After 5 min, 402 mg (0.9 mmol) of (R)-2-amino-1-(3-but-2-ynyloxy-3-o-tolylazetidin-1-yl)-3-(4-methoxyphenyl)-propan-1-one dissolved in 4 ml of dimethylformamide are added. The reaction medium is then stirred for 90 h at ambient temperature, and then a 1N aqueous solution of sodium hydroxide is added and the medium is extracted with a 1/1 heptane/ethyl acetate mixture. The organic phase is washed with a saturated aqueous solution of sodium chloride and then dried over sodium sulphate, filtered and concentrated. The residue obtained is purified by silica gel chromatography, elution being carried out with an 88/12 dichloromethane/methanol mixture. 45 mg of N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide are obtained in the form of a white solid with a yield of 9%.

$^1$H NMR/DMSO d$^6$ 100° C.: δ=1.74 (s, 3H); 2.06 (s, 3H); 2.21 (s, 3H); 2.30-2.45 (m, 2H); 2.55-2.70 (m, 2H); 2.74-3.10 (m, 2H); 3.55-3.80 (m, 5H); 4.00-4.45 (m, 4H); 4.50 (bq, J=8.0 Hz, 1H); 6.65-6.85 (m, 2H); 7.00-7.15 (m, 2H); 7.15-7.35 (m, 5H); 7.75-7.90 (m, 1H).

Table I illustrates the examples of compounds according to the invention.

In this table:

- in the "salt" column, TFA represents a compound in trifluoroacetate form,
- purity (%) represents the purity of the product, obtained by HPLC,
- mass (M+H) represents the mass+1 (hydrogen) derived from the mass spectrum, associated with the HPLC peak of the expected product.

TABLE I

| No. | Name | Salt | Purity (%) | HPLC retention time (min) | Mass (M + H) | HPLC method used | Synthesis pathway used: refer to example No. |
|---|---|---|---|---|---|---|---|
| 1 | 1-[(S)-2-[(S)-2-benzoylamino-3-(1H-imidazol-4-yl)propionylamino]-3-(4-methoxyphenyl)propionyl]-3-phenylazetidin-3-yl ester of butyric acid | TFA | 38 + 51 | (20.02 + 20.26)* | 638 | C | 2 |
| 2 | N-[(S)-1-[(S)-2-(3-butoxy-3-o-tolylazetidin-1-yl)-1-(4-methoxybenzyl)-2-oxoethylcarbamoyl]-2-(1H-imidazol-4-yl)ethyl]benzamide | | 34 + 60 | (16.61 + 16.74)* | 638 | A | 1 |
| 3 | N-[(S)-1-[(S)-2-(3-butoxy-3-phenylazetidin-1-yl)-1-(4-methoxybenzyl)-2-oxoethylcarbamoyl]-2-(1H-imidazol-4-yl)ethyl]benzamide | | 34 + 57 | (16.44 + 16.80)* | 624 | A | 1 |
| 4 | N-[(S)-1-[(S)-2-(3-hydroxy-3-o-tolylazetidin-1-yl)-1-(4-methoxybenzyl)-2-oxoethylcarbamoyl]-2-(1H-imidazol-4-yl)ethyl]benzamide | TFA | 29 + 62 | (11.36 + 11.61)* | 582 | B | 1 + 8 |
| 5 | 1-[(S)-2-[(S)-2-benzoylamino-3-(1H-imidazol-4-yl)propionylamino]-3-(4-methoxyphenyl)propionyl]-3-o-tolylazetidin-3-yl acetate | TFA | 27 + 68 | (12.33 + 12.53)* | 624 | B | 2 |
| 6 | 1-[(S)-2-[(S)-2-benzoylamino-3-(1H-imidazol-4-yl)propionylamino]-3-(4-methoxyphenyl)propionyl]-3-(4-fluorophenyl)azetidin-3-yl ester of butyric acid | | 28.55 | (13.51 + 13.72)* | 656 | B | 2 |
| 7 | N-[(S)-1-[(S)-2-(3-cyclohexyl-3-hydroxyazetidin-1-yl)-1-(4-methoxybenzyl)-2-oxoethylcarbamoyl]-2-(1H-imidazol-4-yl)ethyl]benzamide | | 36 + 62 | (10.68 + 10.94)* | 574 | B | 3 |
| 8 | N-[(S)-1-[(S)-2-[3-butoxy-3-(4-fluorophenyl)azetidin-1-yl]-1-(4-methoxybenzyl)-2-oxoethylcarbamoyl]-2-(1H-imidazol-4-yl)ethyl]benzamide | TFA | 38 + 58 | (12.93 + 13.15)* | 642 | B | 1 |
| 9 | N-[(S)-1-[(S)-2-[3-butoxy-3-(3-fluorophenyl)azetidin-1-yl]-1-(4-methoxybenzyl)-2-oxoethylcarbamoyl]-2-(1H-imidazol-4-yl)ethyl]benzamide | TFA | 39 + 55 | (13.11 + 13.33)* | 642 | B | 1 |

| No. | Name | Configuration | Salt | Purity (%) | HPLC retention time (min) | Mass (M + H) | HPLC method used | Synthesis pathway used: refer to example No. |
|---|---|---|---|---|---|---|---|---|
| 10 | N-[(S)-2-(3-cyclohexyl-3-hydroxyazetidin-1-yl)-1-(4-methoxybenzyl)-2-oxoethyl]-3-(1H-imidazol-4-yl)propionamide | L | — | 96 | 9.68 | 455 | D | 3 + 8 |
| 11 | N-[(S)-2-(3-hydroxy-3-o-tolylazetidin-1-yl)-1-(4-methoxybenzyl)-2-oxoethyl]-3-(1H-imidazol-4-yl)propionamide | L | TFA | 89 | 9.25 | 463 | D | 8 |
| 12 | N-[(R)-1-(3,4-dichlorobenzyl)-2-(3-hydroxy-3-phenylazetidin-1-yl)-2-oxoethyl]-3-(1H-imidazol-4-yl)propionamide | D | TFA | 96 | 12.1 | 487 | J | 8 |
| 13 | N-[(S)-2-(3-ethoxy-3-o-tolylazetidin-1-yl)-1-(4-methoxybenzyl)-2-oxoethyl]-3-(1H-imidazol-4-yl)propionamide | L | — | 95 | 14.77 | 491 | E | 4 |
| 14 | N-[(S)-2-(3-cyclopropylmethoxy-3-o-tolylazetidin-1-yl)-1-(4-methoxybenzyl)-2-oxoethyl]-3-(1H-imidazol-4-yl)propionamide | L | — | 97 | 15.65 | 517 | E | 4 |
| 15 | N-[(R)-2-(3-butoxy-3-o-tolylazetidin-1-yl)-1-(4-methoxybenzyl)-2-oxoethyl]-3-(1H-imidazol-4-yl)propionamide | D | — | 99.8 | 16.52 | 517 | E | 4 |
| 16 | N-[(S)-2-(3-butoxy-3-o-tolylazetidin-1-yl)-1-(4-methoxybenzyl)-2-oxoethyl]-3-(1H-imidazol-4-yl)propionamide | L | — | 99.2 | 16.51 | 519 | E | 4 |
| 17 | N-[(R)-2-(3-ethoxy-3-o-tolylazetidin-1-yl)-1-(4-methoxybenzyl)-2-oxoethyl]-3-(1H-imidazol-4-yl)propionamide | D | — | 98.7 | 14.8 | 491 | E | 4 |
| 18 | N-[(R)-2-(3-butoxy-3-phenylazetidin-1-yl)-1-cyclohexylmethyl-2-oxoethyl]-3-(1H-imidazol-4-yl)propionamide | D | TFA | 84 | 17.45 | 481 | E | 1 + 8 |
| 19 | N-[(R)-2-(3-butoxy-3-phenylazetidin-1-yl)-1-(2,4-dichlorobenzyl)-2-oxoethyl]-3-(1H-imidazol-4-yl)propionamide | D | TFA | 99 | 17.68 | 543 | E | 1 + 8 |
| 20 | N-[(R)-2-(3-cyclopropylmethoxy-3-o-tolylazetidin-1-yl)-1-(4-methoxybenzyl)-2-oxoethyl]-3-(1H-imidazol-4-yl)propionamide | D | — | 96 | 15.22 | 517 | F | 4 |
| 21 | N-[(S)-1-(4-methoxybenzyl)-2-oxo-2-(3-propoxy-3-o-tolylazetidin-1-yl)ethyl]-3-(1H-imidazol-4-yl)propionamide | L | — | 99.4 | 13.59 | 504 | G | 4 |
| 22 | N-[(R)-1-(4-methoxybenzyl)-2-oxo-2-(3-propoxy-3-o-tolylazetidin-1-yl)ethyl]-3-(1H-imidazol-4-yl)propionamide | D | — | 99.4 | 13.57 | 505 | G | 4 |
| 23 | N-[(R)-2-[3-butoxy-3-(4-fluorophenyl)azetidin-1-yl]-1-(4-methoxybenzyl)-2-oxoethyl]-3-(1H-imidazol-4-yl)propionamide | D | — | 96.2 | 10.36 | 523 | A | 4 |
| 24 | N-[(R)-1-(4-methoxybenzyl)-2-oxo-2-(3-pentyloxy-3-o-tolylazetidin-1-yl)ethyl]-3-(1H-imidazol-4-yl)propionamide | D | — | 99 | 18.2 | 533 | M | 4 |

TABLE I-continued

| No. | Name | Salt | Purity (%) | HPLC retention time (min) | Mass (M + H) | HPLC method used | Synthesis pathway used: refer to example No. |
|---|---|---|---|---|---|---|---|
| 25 | N-[(R)-2-(3-hexyloxy-3-o-tolylazetidin-1-yl)-1-(4-methoxybenzyl)-2-oxoethyl]-3-(1H-imidazol-4-yl)propionamide | D | — | 97 | 17.1 | 547 | H | 4 |
| 26 | N-[(R)-1-(4-methoxybenzyl)-2-oxo-2-(3-pentyl-3-phenylazetidin-1-yl)ethyl]-3-(1H-imidazol-4-yl)propionamide | D | — | 97 | 22.9 | 503 | L | 5 |
| 27 | N-[(R)-2-(3-butyl-3-phenylazetidin-1-yl)-1-(4-methoxybenzyl)-2-oxoethyl]-3-(1H-imidazol-4-yl)propionamide | D | — | 98 | 15.72 | 489 | I | 5 |
| 28 | N-[(R)-2-(3-cyclopropylmethoxy-3-phenylazetidin-1-yl)-1-(4-methoxybenzyl)-2-oxoethyl]-3-(1H-imidazol-4-yl)propionamide | D | — | 94 | 14.47 | 503 | I | 4 |
| 29 | N-[(R)-2-(3-hydroxy-3-o-tolylazetidin-1-yl)-1-(4-methoxybenzyl)-2-oxoethyl]-3-(1H-imidazol-4-yl)propionamide | D | TFA | 100 | 13.46 | 463 | K | 4 + 8 |

| No. | Name | Salt | Purity (%) | HPLC retention time (min) | Mass (M + H) | HPLC method used | Synthesis pathway used: refer to example No. |
|---|---|---|---|---|---|---|---|
| 31 | N-[(R)-2-[3-butoxy-3-(4-fluorophenyl)azetidin-1-yl]-1-(3-fluorobenzyl)-2-oxoethyl]-3-(1H-imidazol-4-yl)propionamide | — | 95 | 15.95 | 511 | I | 4 |
| 32 | N-[(R)-2-[3-butoxy-3-(4-fluorophenyl)azetidin-1-yl]-1-(4-fluorobenzyl)-2-oxoethyl]-3-(1H-imidazol-4-yl)propionamide | — | 99 | 15.54 | 511 | I | 4 |
| 33 | N-[(R)-2-(3-butoxy-3-phenylazetidin-1-yl)-1-(4-fluorobenzyl)-2-oxoethyl]-3-(1H-imidazol-4-yl)propionamide | — | 93 | 15.75 | 493 | I | 4 |
| 34 | N-{(R)-1-benzyl-2-[3-butoxy-3-(4-fluoro-phenyl)azetidin-1-yl]-2-oxoethyl}-3-(4H-imidazol-2-yl)propionamide | — | 100 | 15.42 | 493 | I | 4 |
| 35 | N-[(R)-1-benzyl-2-(3-butoxy-3-phenylazetidin-1-yl)-2-oxoethyl]-3-(1H-imidazol-4-yl)propionamide | — | 91 | 15.75 | 475 | I | 4 |
| 36 | N-[(R)-2-(3-butoxy-3-phenylazetidin-1-yl)-1-(4-methoxybenzyl)-2-oxoethyl]-3-(1H-imidazol-4-yl)propionamide | TFA | 90 | 16.93 | 505 | M | 4 |
| 37 | N-[(R)-1-(4-methoxybenzyl)-2-oxo-2-(3-pentyl-3-o-tolylazetidin-1-yl)ethyl]-3-(1H-imidazol-4-yl)propionamide | — | 97 | 16.13 | 517 | N | 5 |
| 38 | N-[(R)-2-[3-(4-fluorophenyl)-3-pentylazetidin-1-yl]-1-(4-methoxybenzyl)-2-oxoethyl]-3-(1H-imidazol-4-yl)propionamide | — | 99 | 15.85 | 521 | O | 9 |
| 39 | N-[(R)-2-(3-butoxy-3-o-tolylazetidin-1-yl)-1-(4-methoxybenzyl)-2-oxoethyl]-3-(1H-[1,2,3]triazol-4-yl)propionamide | — | 93 | 19.03 | 520 | M | 6 |
| 40 | N-[(R)-2-(3-butoxy-3-o-tolylazetidin-1-yl)-1-(4-methoxybenzyl)-2-oxoethyl]-3-(5-methyl-3H-[1,2,4]triazol-3-yl)propionamide | — | 98 | 17.33 | 534 | M | 4 |
| 41 | N-[(R)-2-(3-butoxy-3-o-tolylazetidin-1-yl)-1-(4-methoxybenzyl)-2-oxoethyl]-3-(5-methyl-3H-imidazol-4-yl)propionamide | — | 96 | 17.65 | 533 | M | 7 |
| 42 | N-{(R)-1-(4-methoxybenzyl)-2-[3-(2-methoxyphenyl)-3-pentylazetidin-1-yl]-2-oxoethyl}-3-(1H-imidazol-4-yl)propionamide | — | 99 | 16.37 | 553 | P | 9 |
| 43 | N-[(R)-2-[3-(2-fluorophenyl)-3-pentylazetidin-1-yl]-1-(4-methoxybenzyl)-2-oxoethyl]-3-(1H-imidazol-4-yl)propionamide | — | 99 | 15.65 | 521 | Q | 9 |
| 44 | N-[(R)-2-[3-(2-chlorophenyl)-3-pentylazetidin-1-yl]-1-(4-methoxybenzyl)-2-oxoethyl]-3-(1H-imidazol-4-yl)propionamide | — | 98 | 16.04 | 537 | Q | 9 |
| 45 | N-[(R)-1-(4-chlorobenzyl)-2-oxo-2-(3-pentyl-3-phenylazetidin-1-yl)ethyl]-3-(1H-imidazol-4-yl)propionamide | — | 97 | 14.85 | M = 507 | R | 9 |
| 46 | N-[(R)-1-(4-fluorobenzyl)-2-oxo-2-(3-pentyl-3-phenylazetidin-1-yl)ethyl]-3-(1H-imidazol-4-yl)propionamide | — | 96 | 14.39 | 491 | R | 9 |
| 47 | N-[(R)-1-benzyl-2-oxo-2-(3-pentyl-3-phenylazetidin-1-yl)ethyl]-3-(1H-imidazol-4-yl)propionamide | — | 95 | 14.3 | 473 | R | 9 |
| 48 | N-[(R)-2-(3-butoxy-3-o-tolylazetidin-1-yl)-1-(4-methoxybenzyl)-2-oxoethyl]-3-(1H-imidazol-4-yl)acrylamide | — | 98 | 10.87 | 517 | S | 4 |
| 49 | N-[(R)-2-[3-(2,4-difluorophenyl)-3-pentylazetidin-1-yl]-1-(4-methoxybenzyl)-2-oxoethyl]-3-(1H-imidazol-4-yl)propionamide | — | 98 | 15.89 | 539 | T | 9 |
| 50 | N-[(R)-2-oxo-2-(3-pentyl-3-phenylazetidin-1-yl)-1-(3-trifluoromethylbenzyl)ethyl]-3-(1H-imidazol-4-yl)propionamide | — | 98 | 16.61 | 541 | T | 9 |
| 51 | N-[(R)-2-oxo-2-(3-pentyl-3-phenylazetidin-1-yl)-1-(4-trifluoromethylbenzyl)ethyl]-3-(1H-imidazol-4-yl)propionamide | — | 98 | 16.5 | 541 | T | 9 |

TABLE I-continued

| | | | | | | | |
|---|---|---|---|---|---|---|---|
| 52 | N-[(R)-1-(3,4-dichlorobenzyl)-2-oxo-2-(3-pentyl-3-phenylazetidin-1-yl)ethyl]-3-(1H-imidazol-4-yl)propionamide | — | 96 | 16.78 | M = 541 | T | 9 |
| 53 | N-[(R)-1-(3,4-difluorobenzyl)-2-oxo-2-(3-pentyl-3-phenylazetidin-1-yl)ethyl]-3-(1H-imidazol-4-yl)propionamide | — | 97 | 16.02 | 509 | T | 9 |
| 54 | N-[(R)-2-[3-(3,4-dichlorophenyl)-3-pentylazetidin-1-yl]-1-(4-methoxybenzyl)-2-oxoethyl]-3-(1H-imidazol-4-yl)propionamide | — | 99 | 17.79 | M = 571 | P | 9 |
| 55 | N-[(R)-2-[3-(3-fluorophenyl)-3-pentylazetidin-1-yl]-1-(4-methoxybenzyl)-2-oxoethyl]-3-(1H-imidazol-4-yl)propionamide | — | 96 | 15.77 | 521 | U | 9 |
| 56 | N-[(R)-1-(3-fluorobenzyl)-2-oxo-2-(3-pentyl-3-phenylazetidin-1-yl)ethyl]-3-(1H-imidazol-4-yl)propionamide | TFA | 98 | 15.82 | 491 | U | 9 |
| 57 | N-[(R)-1-(2-fluorobenzyl)-2-oxo-2-(3-pentyl-3-phenylazetidin-1-yl)ethyl]-3-(1H-imidazol-4-yl)propionamide | TFA | 99 | 15.76 | 491 | U | 9 |
| 58 | N-[(R)-1-(2,4-dichlorobenzyl)-2-oxo-2-(3-pentyl-3-phenylazetidin-1-yl)ethyl]-3-(1H-imidazol-4-yl)propionamide | — | 98 | 17.3 | M = 541 | U | 9 |
| 59 | N-[(R)-2-[3-(4-dichlorophenyl)-3-pentylazetidin-1-yl]-1-(4-methoxybenzyl)-2-oxoethyl]-3-(1H-imidazol-4-yl)propionamide | — | 97 | 16.67 | 537 | U | 9 |
| 60 | N-[(R)-2-[3-(2,5-difluorophenyl)-3-pentylazetidin-1-yl]-1-(4-methoxybenzyl)-2-oxoethyl]-3-(1H-imidazol-4-yl)propionamide | — | 97 | 18.66 | 539 | V | 9 |
| 61 | N-[(R)-2-[3-(2,6-difluorophenyl)-3-pentylazetidin-1-yl]-1-(4-methoxybenzyl)-2-oxoethyl]-3-(1H-imidazol-4-yl)propionamide | — | 98 | 18.67 | 539 | V | 9 |
| 62 | N-[2-(3-butoxy-3-o-tolylazetidin-1-yl)-1-(4-methoxybenzyl)-2-oxoethyl]-3-(1H-imidazol-4-yl)hexyramide | — | 99 | 18.05 | 561 | V | 10 |
| 63 | N-[2-(3-butoxy-3-o-tolylazetidin-1-yl)-1-(4-methoxybenzyl)-2-oxoethyl]-3-(1H-imidazol-4-yl)pentyramide | TFA | 97 | 17.56 | 547 | V | 10 |
| 64 | N-[(R)-1-(4-methoxybenzyl)-2-oxo-2-(3-pentyl-3-phenylazetidin-1-yl)ethyl]-3-(3-methyl-3H-imidazol-4-yl)propionamide | — | 96 | 18.04 | 517 | W | 11 |
| 65 | N-[2-(3-butoxy-3-o-tolylazetidin-1-yl)-1-(2,4-dichlorobenzyl)-2-oxoethyl]-3-(1H-imidazol-4-yl)hexyramide | — | 95 | 17.49 | 599 | X | 10 |
| 66 | N-[(R)-2-(3-cyclohexyl-3-pentylazetidin-1-yl)-1-(4-methoxybenzyl)-2-oxoethyl]-3-(1H-imidazol-4-yl)propionamide | — | 98 | 18.34 | 509 | Y | 12 |
| 67 | N-[(R)-2-(3-butoxy-3-o-tolylazetidin-1-yl)-1-(4-methoxybenzyl)-2-oxoethyl]-3-(3-methyl-3H-imidazol-4-yl)propionamide | — | 95 | 15.24 | 533 | Z | 11 |

| No. | Name | | Purity (%) | HPLC retention time (min) | Mass (M + H) | HPLC method used |
|---|---|---|---|---|---|---|
| 68 | N-[(R)-2-[3-Butoxy-3-(2-fluorophenyl)azetidin-1-yl]-1-(4-methoxybenzyl)-2-oxoethyl]-3-(1H-imidazol-4-yl)propionamide | | — | — | — | — |
| 69 | N-[(R)-2-(3-Butoxy-3-o-tolylazetidin-1-yl)-1-(4-methoxybenzyl)-2-oxoethyl]-3-(1-methyl-1H-imidazol-4-yl)propionamide | | 96 | 15.28 | 533 | U |
| 70 | N-[2-(3-Butoxy-3-o-tolylazetidin-1-yl)-1-(2-hydroxy-4-methoxybenzyl)-2-oxoethyl]-3-(3H-imidazol-4-yl)propionamide trifluoroacetate | | 94 | 14.39 | 535 | T |
| 71 | (S)-N-[(R)-2-(3-Butoxy-3-o-tolylazetidin-1-yl)-1-(4-methoxybenzyl)-2-oxoethyl]-2-hydroxy-3-(1H-imidazol-4-yl)propionamide | | — | — | — | — |
| 72 | N-[(R)-2-(3-Butoxy-3-o-tolylazetidin-1-yl)-1-(4-hydroxybenzyl)-2-oxoethyl]-3-(3H-imidazol-4-yl)propionamide | | — | — | — | — |
| 73 | N-[1-(3-Butoxy-3-o-tolylazetidine-1-carbonyl)-2-hydroxy-2-(4-methoxyphenyl)ethyl]-3-(1H-imidazol-4-yl)propionamide | | — | — | — | — |
| 74 | N-[(R)-2-(3-Butoxy-3-o-tolylazetidin-1-yl)-1-(4-methoxybenzyl)-2-oxoethyl]-3-hydroxy-3-(1H-imidazol-4-yl)propionamide | | — | — | — | — |

TABLE I-continued

| | | | | | |
|---|---|---|---|---|---|
| 75 | N-[(R)-2-(3-But-2-ynyl-3-o-tolylazetidin-1-yl)-1-(4-methoxybenzyl)-2-oxoethyl]-3-(1H-imidazol-4-yl)propionamide | — | — | — | — |
| 76 | N-[(R)-2-(3-But-2-ynyloxy-3-o-tolylazetidin-1-yl)-1-(4-methoxybenzyl)-2-oxoethyl]-3-(5-methyl-1H-imidazol-4-yl)propionamide | — | — | — | — |
| 77 | N-[(R)-2-(3-Cyclohexylmethoxy-3-o-tolylazetidin-1-yl)-1-(4-methoxybenzyl)-2-oxoethyl]-3-(1H-imidazol-4-yl)propionamide | — | — | — | — |
| 78 | 3-(1H-Imidazol-4-yl)-N-[(R)-1-(4-methoxybenzyl)-2-oxo-2-[3-o-tolyl-3-(4,4,4-trifluorobutoxy)azetidin-1-yl]ethyl]propionamide | — | — | — | — |
| 79 | N-[(R)-2-(3-Cyclobutylmethoxy-3-o-tolylazetidin-1-yl)-1-(4-methoxybenzyl)-2-oxoethyl]-3-(5-methyl-1H-imidazol-4-yl)propionamide | — | — | — | — |
| 80 | N-[(R)-1-(4-Methoxybenzyl)-2-[3-(3-methylbut-2-enyloxy)-3-o-tolylazetidin-1-yl]-2-oxoethyl]-3-(5-methyl-1H-imidazol-4-yl)propionamide | — | — | — | — |

| No. | $^1$H NMR/DMSO D$_6$ 100° C. | Synthesis pathway used: refer to Example No. |
|---|---|---|
| 68 | $^1$H NMR/DMSO$_{D6}$ 100° C.: δ = 0.78 (t, J = 7.2-7.6 Hz, 3H); 1.23 (sext. J = 6.8-7.2 Hz, 2H); 1.37 (quint, J = 6.4-7.6 Hz, 2H); 2.38-2.42 (m, 2H); 2.68-2.94 (m, 7H); 3.10 (bt, J = 5.6-6.4, 2H); 4.00-4.40 (m, 4H); 4.50 (q, J = 7.2-7.6 Hz, 1H); 6.67-6.80 (m, 3H); 7.09-7.24 (m, 4H); 7.30-7.43 (m, 4H); 7.70-7.90 (m, 1H). | 13 |
| 69 | | 14 |
| 70 | | 15 |
| 71 | $^1$H NMR/DMSO$_{D6}$ 100° C.: δ = 1.40 (m, 4H); 2.22 (s, 3H); 2.84-2.81 (m, 6H); 2.96 (m, 2H); 3.33 (t, J = 6.4 Hz, 2H); 3.68 (m, 3H); 4.08 (d, J = 10 Hz, 2H); 4.21 (m, 2H); 4.55 (q, J = 7.2 Hz, 1H); 6.76 (m, 2H); 7.11 (m, 2H); 7.27-7.18 (m, 5H); 7.91 (m, 1H); 8.63 (s, 1H). | 16 |
| 72 | $^1$H NMR/DMSO$_{D6}$ 100° C.: δ = 0.78 (t, J = 7.2 Hz, 3H); 1.23 (sext, J = 7.3 Hz, 2H); 1.36 (quint, J = 6.7 Hz, 2H); 2.12 (s, 3H); 2.55-2.75 (m, 1H); 2.86-2.98 (m, 7H); 3.68 (bs, 3H); 3.90-4.30 (m, 4H); 4.54 (bq, J = 6.4 Hz, 1H); 5.25-5.45 (m, 1H); 6.55-6.95 (m, 3H); 7.09-7.27 (m, 6H); 7.43 (bs, 1H); 7.50-7.65 (m, 1H). | 17 |
| 73 | $^1$H NMR/DMSO$_{D6}$ 100° C.: δ = 0.80 (t, J = 7.6 Hz, 3H); 1.22 (m, 2H); 1.36 (quint, J = 6.4 Hz, 2H); 2.23 (s, 3H); 2.40 (t, J = 8.8 Hz, 2H); 2.82-2.70 (m, 4H); 2.97 (t, J = 6.4 Hz, 2H); 4.09 (d, J = 10 Hz, 2H); 4.23 (d, J = 7.6 Hz, 2H); 4.50 (q, J = 7.6 Hz, 1H); 6.63 (m, 2H); 6.70 (s, 1H); 6.99 (m, 2H); 7.26-7.20 (m, 4H); 7.49 (s, 1H); 7.75 (s, 1H). | 18 |
| 74 | $^1$H NMR/DMSO$_{D6}$ 100° C.: δ = 0.78 (t, J = 7.6 Hz, 3H); 1.23 (sext, J = 7.3 Hz, 2H); 1.37 (quint, J = 6.7 Hz, 2H); 2.25 (s, 3H); 2.40-2.50 (m, 2H); 2.75 (m, 2H); 3.01 (t, J = 12 Hz, 2H); 3.70-3.80 (bs, 3H); 4.10-4.50 (m, 6H); 4.55 (m, 1H); 4.73 (m, 1H); 6.82 (m, 2H); 7.10-7.40 (m, 8H); 7.86 (m, 1H). | 19 |
| 75 | $^1$H NMR/DMSO$_{D6}$ 100° C.: δ = 0.78 (t, J = 7.2 Hz, 3H); 1.23 (sext, J = 7.3 Hz, 2H); 1.36 (quint, J = 6.7 Hz, 2H); 2.21 (s, 3H); 2.55-2.65 (m, 2H); 2.70-2.90 (m, 3H); 2.90-3.00 (m, 2H); 3.68 (bs, 3H); 3.90-4.40 (m, 5H); 4.54 (bq, J = 7.2 Hz, 1H); 4.92 (bs, 1H); 6.60-6.80 (m, 3H); 7.00-7.30 (m, 6H); 7.46 (bs, 1H); 7.81 (bs, 1H). | 20 |
| 76 | $^1$H NMR/DMSO$_{D6}$ 100° C.: δ = 1.74 (bs, 3H); 2.21 (s, 3H); 2.39-2.43 (m, 2H); 2.69-3.10 (m, 4H); 3.68 (m, 5H); 4.10-4.40 (m, 4H); 4.52 (q, J = 7.2-8.0 Hz, 1H); 6.67-6.85 (m, 3H); 7.05-7.15 (m, 2H); 7.18-7.29 (m, 4H); 7.41 (s, 1H); 7.75-7.85 (m, 1H). | 21 |
| 77 | δ = 0.79-1.59 (m, 11H); 2.21 (s, 3H); 2.39-2.43 (m, 2H); 2.70-2.90 (m, 6H); 2.93 (s, 3H); 4.04-4.40 (m, 4H); 4.53 (q, J = 7.2-7.6 Hz, 1H); 6.67-6.80 (m, 3H); 7.09-7.26 (m, 7H); 7.40 (s, 1H); 7.77 (s, 1H). | 8 |
| 78 | δ = 1.60 (quintl, 2H); 2.08-2.19 (m, 2H); 2.22 (s, 3H); 2.39-2.43 (m, 2H); 2.68-2.93 (m, 7H); 3.02-3.06 (m, 2H); 4.07-4.40 (m, 4H); 4.52 (q, J = 7.2-7.6 Hz, 1H); 6.65-6.90 (m, 3H); 7.00-7.30 (m, 7H); 7.40 (s, 1H); 7.70-7.85 (m, 1H). | 8 |
| 79 | δ = 1.55 (quintl, J = 7.6-10.8 Hz, 2H); 1.70-1.83 (m, 2H); 1.88-1.96 (m, 2H); 2.06 (s, 3H); 2.22 (s, 3H); 2.31-2.38 (m, 3H); 2.60-2.70 (m, 2H); 2.74-2.80 (m, 1H); 2.80-3.05 (m, 3H); 3.69 (bs, 3H); 4.00-4.40 (m, 4H); 4.52 (bq, J = 7.2-7.6 Hz, | 9 |

TABLE I-continued

| | |
|---|---|
| | 1H); 6.70-6.85 (m, 2H); 7.05-7.15 (m, 2H); 7.18-7.28 (m, 5H); 7.75-7.85 (m, 1H). |
| 80 | δ = 1.43 (s, 3H); 1.63 (s, 3H); 2.06 (s, 3H); 2.22 (s, 3H); 2.36 (bt, J = 6.8-7.2 Hz, 2H); 2.62 (bt, J = 7.2 Hz, 2H); 2.76-3.10 (m, 2H); 3.52 (d, J = 6.8 Hz, 2H); 3.68 (bs, 3H); 4.00-4.45 (m, 4H); 4.52 (q, J = 7.2-7.6 Hz, 1H); 5.12 (bt, J = 6.8-8.0 Hz, 1H); 6.65-6.90 (m, 2H); 7.09-7.18 (m, 2H); 7.19-7.27 (m, 4H); 7.30 (s, 1H); 7.70-7.85 (m, 1H). | 9 |

(*mixture of conformers)

EXAMPLE 22

Transactivation Test: Melanocortin Receptors

Cells:

HEK293 lines are transfected with the pCRE-Luc and hMC1R, hMC3R, hMC4R or hMC5R vectors. The cells are cultured at 37° C., 5% $CO_2$, in DMEM medium supplemented with 10% of foetal calf serum.

Principle of the Test:

In the presence of an activator (agonist), the melanocortin receptor will activate the cAMP pathway which, via the CRE-Luc vector, will result in the synthesis of luciferase. After the addition of a lysis buffer containing a luminescent substrate for luciferase, it will be possible to measure the luminescence proportional to the degree of activation or of inhibition of the receptor.

Product Test:

The products are solubilized at 10 mM in DMSO. They are tested in the form of dose-response at a final DMSO concentration of 0.1%. The range comprising 10 points and one zero begins at 10 μM with 4-fold dilutions. For testing agonists, the products are tested alone. For determining the behaviour of antagonists, the products of interest are tested in the presence of 1 nM NDP-MSH (reference agonist). The cells are seeded at a rate of 5000 cells per well (384 well plate) in serum-free DMEM medium, and incubated overnight at 37° C., 5% $CO_2$.

The products and the reference ligand (NDP-MSH) are added the following day, and the plates are again incubated for 6 h at 37° C., 5% $CO_2$. After the addition of lysis buffer containing luciferin, the plates are read on a Top-Count instrument. The results are standardized as % activity using the 100% (cells+NDP-MSH at 10 nM) and 0% (cells alone) controls. An EC50 is calculated for each product using the XLFit software. The results are given in nM.

| Example No. | EC50 hMC1R (nM) | EC50 hMC4R (nM) |
|---|---|---|
| 1 | 500 | NT |
| 2 | 30 | 8000 |
| 3 | 60 | 4000 |
| 4 | 250 | 4000 |
| 5 | 4000 | 8000 |
| 6 | 2000 | 8000 |
| 7 | 500 | 4000 |
| 8 | 120 | 4000 |
| 9 | 120 | 1000 |
| 10 | 8000 | IA |
| 11 | 4000 | 8000 |
| 12 | 8000 | IA |
| 13 | 2000 | 15000 |
| 14 | 2000 | 15000 |
| 15 | 120 | 4000 |
| 16 | 2000 | 15000 |
| 17 | 250 | 8000 |
| 18 | 8000 | 8000 |
| 19 | 2000 | 120 |
| 20 | 120 | 4000 |
| 21 | 4000 | IA |
| 22 | 120 | 10000 |
| 23 | 60 | 1000 |
| 24 | 250 | 4000 |
| 25 | 1000 | 8000 |
| 26 | 500 | 4000 |
| 27 | 500 | 8000 |
| 28 | 1000 | 8000 |
| 29 | 1000 | IA |
| 31 | 500 | 4000 |
| 32 | 1000 | 4000 |
| 33 | 500 | 2000 |
| 34 | 1000 | 2000 |
| 35 | 500 | 2000 |
| 36 | 1000 | 3000 |
| 37 | 250 | 2000 |
| 38 | 250 | NT |
| 39 | 8000 | 2000 |
| 40 | 8000 | 500 |
| 41 | 120 | 1000 |
| 42 | 60 | 30 |
| 43 | 30 | NT |
| 44 | 30 | NT |
| 45 | 2000 | 2000 |
| 46 | 1000 | 4000 |
| 47 | 500 | 4000 |
| 48 | 4000 | 500 |
| 49 | 15 | 2000 |
| 50 | 1000 | 500 |
| 51 | 1000 | IA |
| 52 | 2000 | 250 |
| 53 | 1000 | 4000 |
| 54 | 250 | NT |
| 55 | 120 | 1000 |
| 56 | 4000 | 8000 |
| 57 | 1000 | 4000 |
| 58 | 2000 | 500 |
| 59 | NT | IA |
| 60 | 120 | 100 |
| 61 | 120 | 100 |
| 62 | 4000 | 500 |
| 63 | 500 | 500 |
| 64 | 2000 | 500 |
| 65 | IA | 100 |
| 66 | 250 | 250 |
| 67 | 500 | 500 |
| 68 | 60 | 2000 |
| 69 | 1000 | 8000 |
| 70 | 4000 | IA |
| 71 | 60 | 4000 |
| 72 | 2000 | IA |
| 73 | 500 | 8000 |
| 74 | 250 | 8000 |
| 75 | 60 | 4000 |
| 76 | 30 | 4000 |
| 77 | 120 | 2000 |
| 78 | 120 | 2000 |
| 79 | 15 | 1000 |
| 80 | 15 | 4000 |

IA: inactive
NT: not tested

What is claimed is:

1. A method for treating a disorder, disease, or dysfunction selected from the group consisting of:
   an inflammatory disease of the digestive tract selected from the group consisting of irritable bowel syndrome, ulcerative colitis, Crohn's disease, pancreatitis, hepatitis, an inflammatory pathological condition of the bladder and gastritis;
   an inflammatory disease of the locomotor system selected from the group consisting of rheumatoid arthritis, osteoarthritis, osteoporosis, traumatic arthritis, post-infectious arthritis, muscle degeneration and dermatomyositis;
glomerulonephritis;
   an inflammatory disease of the cardiac system selected from the group consisting of pericarditis, myocarditis, atherosclerosis, transplant atherosclerosis, peripheral vascular disease, inflammatory vasculardisease, intermittent claudication, restenosis, stroke, transient ischaemic attack, myocardial ischaemia, myocardial infarction, hypertension, hyperlipidaemia, coronary artery disease, unstable angina, thrombosis, platelet aggregation induced by thrombin and atheroma plaque formation;
   an inflammatory disease of the respiratory and ENT system selected from the group consisting of asthma, acute respiratory distress syndrome, hayfever, allergic rhinitis, chronic obstructive pulmonary disease and allergies;
   an inflammatory disease of the central nervous system selected from the group consisting of Alzheimer's disease, other form of dementia, Parkinson's disease, Creutzfeldt Jacob disease, multiple sclerosis and meningitis;
   an inflammatory skin disease selected from the group consisting of urticaria, scleroderma, contact dermatitis, atopic dermatitis, psoriasis, ichthyosis, acne and other forms of folliculitis, rosacea and alopecia;
   an autoimmune disease selected from the group consisting of lupus erythematosus, a thyroid condition, an autoimmune disease of the adrenal gland, autoimmune gastritis, vitiligo and alopecia areata;
   an inflammation accompanying bacterial, viral or fungal infections selected from the group consisting of tuberculosis, septicaemia, fever, HIV, herpes, cytomegalovirus, hepatitis A, hepatitis B and hepatitis C;
   a transplant or graft rejection selected from the group consisting of kidney, liver, heart, lung, pancreas, bone marrow, cornea, intestine and skin;
   pain selected from the group consisting of post-operative pain, neuromuscular pain, headache, cancer-related pain, dental pain and osteoarticular pain;
   a disease with a pigmentation disorder selected from the group consisting of a benign dermatosis selected from the group consisting of vitiligo, albinism, melasma, lentigines, freckles, melanocytic naevi and post inflammatory pigmentation; and a pigmented tumor selected from the group consisting of melanoma and local metastases, regional metastases and systemic metastases thereof;
   or a method for inhibiting:
   actinic erythema, skin ageing, a skincancer, and a disease in which sunlight accelerates onset selected from the group consisting of xeroderma pigmentosum, basal cell naevus syndrome and familial melanoma;
   a photodermatosis due to an exogenous photosensitizing agent selected from the group consisting of furocoumarins, halogenated salicylanilides, local sulphamides, psoralens, tetracyclines, systemic sulphamides, phenothiazines, nalidixic acid, and tricyclic antidepressants;
   or for inhibiting a dermatosis attack with photosensitivity which is:
   a photoaggravated dermatosis selected from the group consisting of lupus erythematosus, recurrent herpes, congenital poikilodermal and telangiectasic conditions with photosensitivity selected from the group consisting of Bloom syndrome, Cockayne syndrome and Rothmund-Thomson syndrome, actinic lichen planus, actinic granuloma, disseminated superficial actinic porokeratosis, acne rosacea, juvenile acne, bullous dermatosis, Darier's disease, cutaneous lymphoma, psoriasis, atopic dermatitis, contact eczema, follicular mucinosis, erythema multiforme, fixed drug erythema, lymphocytoma cutis, reticular erythema with mucinosis and melasma,
   a dermatosis with photosensitivity caused by deficiency of the protection system with melanin formation or distribution anomalies selected from the group consisting of oculocutaneous albinism, phenylketonuria, anterior hypophyseal insufficiency, vitiligo, and piebaldism and with DNA repair system deficiency selected from the group consisting of xeroderma pigmentosum and Cockayne syndrome,
   a dermatosis with photosensitivity caused by metabolic anomalies which is a cutaneous porphyria selected from the group consisting of late cutaneous porphyria, mixed porphyria, erythropoietic protoporphyria, congenital erythropoietic porphyria Günther's disease and erythropoietic coproporphyria, or which is pellagra or a pellagroid erythema or a tryptophan metabolism disorder;
   an idiopathic photodermatosis attack selected from the group consisting of polymorphous light eruption, benign summer light eruption, actinic prurigo, persistent photosensitization selected from the group consisting of actino-reticulosis, chronic actinic dermatosis, and photosensitive eczema, solar urticaria, hydroa vacciniforme, juvenile spring eruption and solar pruritus,
   or for modulating the color of the skin or of the hair and of body hairs by causing the skin to tan by increasing melanin synthesis or causing it to bleach by interfering with melanin synthesis, by preventing hair and body hair from turning white or grey; or for modifying the color of the hair and body hairs in cosmetic indications;
   or for modulating sebaceous function in treating:
   a condition with hyperseborrhoea selected from the group consisting of acne, seborrhoeic dermatitis, greasy skin and greasy hair, hyperseborrhoea in Parkinson's and epilepsy, and hyperandrogenism;
   a condition with decreasing sebaceous secretion selected from the group consisting of xerosis and dry skin;
   benign and malignant sebocyte and sebaceous gland proliferation;
an inflammatory condition of the pilosebaceous follicle selected from the group consisting of acne, boils, carbuncles and folliculitis;
   a neurodegenerative disorder selected from the group consisting of depression, anxiety, an obsessive-compulsive disorder, a neurosis, a psychosis, insomnia, sleep apnea, and drug abuse;
   a male sexual dysfunction selected from the group consisting of impotence, loss of libido, and erectile dysfunction; a female sexual dysfunction selected from the group consisting of sexual stimulation disorders, or disorders related to desire, sexual receptivity, orgasm, and disturbances of the major points of sexual function; pain, preterm labor, dysmenorrhoea, excessive menstruation, and endometriosis;

a disorder related to weight selected from the group consisting of obesity, anorexia, modification and impairment of appetite, spleen metabolism, innocent intake of fats and carbohydrates; diabetes mellitus;

cancer selected from the group consisting of lung cancer, prostate cancer, colon cancer, breast cancer, ovarian cancer and bone cancer, an angiogenesis disorder, and the formation or growth of a solid tumor, said method comprising administering to a subject in need of such treatment a compound selected from the group consisting of:

N—[(S)-1-[(S)-2-(3-butoxy-3-o-tolylazetidin-1-yl)-1-(4-methoxybenzyl)-2-oxoethylcarbamoyl]-2-(1H-imidazol-4-yl)ethyl]benzamide;

N—[(S)-1-[(S)-2-(3-butoxy-3-phenylazetidin-1-yl)-1-(4-methoxybenzyl)-2-oxoethylcarbamoyl]-2-(1H-imidazol-4-yl)ethyl]benzamide;

N—[(S)-1-[(S)-2-[3-butoxy-3-(4-fluorophenyl)azetidin-1-yl]-1-(4-methoxybenzyl)-2-oxoethylcarbamoyl]-2-(1H-imidazol-4-yl)ethyl]benzamide;

N—[(S)-1-[(S)-2-[3-butoxy-3-(3-fluorophenyl)azetidin-1-yl]-1-(4-methoxybenzyl)-2-oxoethylcarbamoyl]-2-(1H-imidazol-4-yl)ethyl]benzamide;

N—[(R)-2-(3-butoxy-3-o-tolylazetidin-1-yl)-1-(4-methoxybenzyl)-2-oxoethyl]-3-(1H-imidazol-4-yl)propionamide;

N—[(R)-2-(3-ethoxy-3-o-tolylazetidin-1-yl)-1-(4-methoxybenzyl)-2-oxoethyl]-3-(1H-imidazol-4-yl)propionamide;

N—[(R)-2-(3-butoxy-3-phenylazetidin-1-yl)-1-(2,4-dichlorobenzyl)-2-oxoethyl]-3-(1H-imidazol-4-yl)propionamide;

N—[(R)-2-(3-cyclopropyl methoxy-3-o-tolylazetidin-1-yl)-1-(4-methoxybenzyl)-2-oxoethyl]-3-(1H-imidazol-4-yl)propionamide;

N—[(R)-1-(4-methoxybenzyl)-2-oxo-2-(3-propoxy-3-o-tolylazetidin-1-yl)ethyl]-3-(1H-imidazol-4-yl)propionamide;

N—[(R)-2-[3-butoxy-3-(4-fluorophenyl)azetidin-1-yl]-1-(4-methoxybenzyl)-2-oxoethyl]-3-(1H-imidazol-4-yl)propionamide;

N—[(R)-1-(4-methoxybenzyl)-2-oxo-2-(3-pentyloxy-3-o-tolylazetidin-1-yl)ethyl]-3-(1H-imidazol-4-yl)propionamide;

N—[(R)-1-(4-methoxybenzyl)-2-oxo-2-(3-pentyl-3-phenylazetidin-1-yl)ethyl]-3-(1H-imidazol-4-yl)propionamide;

N—[(R)-2-(3-butyl-3-phenylazetidin-1-yl)-1-(4-methoxybenzyl)-2-oxoethyl]-3-(1H-imidazol-4-yl)propionamide;

N—[(R)-2-[3-butoxy-3-(4-fluorophenyl)azetidin-1-yl]-1-(3-fluorobenzyl)-2-oxoethyl]-3-(1H-imidazol-4-yl)propionamide;

N—[(R)-2-(3-butoxy-3-phenylazetidin-1-yl)-1-(4-fluorobenzyl)-2-oxoethyl]-3-(1H-imidazol-4-yl)propionamide;

N—[(R)-1-benzyl-2-(3-butoxy-3-phenylazetidin-1-yl)-2-oxoethyl]-3-(1H-imidazol-4-yl)propionamide;

N—[(R)-1-(4-methoxybenzyl)-2-oxo-2-(3-pentyl-3-o-tolylazetidin-1-yl)ethyl]-3-(1H-imidazol-4-yl)propionamide;

N—[(R)-2-[3-(4-fluorophenyl)-3-pentylazetidin-1-yl]-1-(4-methoxybenzyl)-2-oxoethyl]-3-(1H-imidazol-4-yl)propionamide;

N—[(R)-2-(3-butoxy-3-o-tolylazetidin-1-yl)-1-(4-methoxybenzyl)-2-oxoethyl]-3-(5-methyl-3H-[1,2,4]triazol-3-yl)propionamide;

N—[(R)-2-(3-butoxy-3-o-tolylazetidin-1-yl)-1-(4-methoxybenzyl)-2-oxoethyl]-3-(5-methyl-3H-imidazol-4-yl)propionamide;

N—{(R)-1-(4-methoxybenzyl)-2-[3-(2-methoxyphenyl)-3-pentylazetidin-1-yl]-2-oxoethyl}-3-(1H-imidazol-4-yl)propionamide;

N—[(R)-2-[3-(2-fluorophenyl)-3-pentylazetidin-1-yl]-1-(4-methoxybenzyl)-2-oxoethyl]-3-(1H-imidazol-4-yl)propionamide;

N—[(R)-2-[3-(2-chlorophenyl)-3-pentylazetidin-1-yl]-1-(4-methoxybenzyl)-2-oxoethyl]-3-(1H-imidazol-4-yl)propionamide;

N—[(R)-1-benzyl-2-oxo-2-(3-pentyl-3-phenylazetidin-1-yl)ethyl]-3-(1H-imidazol-4-yl)propionamide;

N—[(R)-2-[3-(2,4-difluorophenyl)-3-pentylazetidin-1-yl]-1-(4-methoxybenzyl)-2-oxoethyl]-3-(1H-imidazol-4-yl)propionamide;

N—[(R)-2-[3-(3,4-dichlorophenyl)-3-pentylazetidin-1-yl]-1-(4-methoxybenzyl)-2-oxoethyl]-3-(1H-imidazol-4-yl)propionamide;

N—[(R)-2-[3-(3,4-dichlorophenyl)-3-pentylazetidin-1-yl]-1-(4-methoxybenzyl)-2-oxoethyl]-3-(1H-imidazol-4-yl)propionamide;

N—[(R)-2-[3-(3-fluorophenyl)-3-pentylazetidin-1-yl]-1-(4-methoxybenzyl)-2-oxoethyl]-3-(1H-imidazol-4-yl)propionamide;

N—[(R)-1-(2,4-dichlorobenzyl)-2-oxo-2-(3-pentyl-3-phenylazetidin-1-yl)ethyl]-3-(1H-imidazol-4-yl)propionamide;

N—[(R)-2-[3-(2,5-difluorophenyl)-3-pentylazetidin-1-yl]-1-(4-methoxybenzyl)-2-oxoethyl]-3-(1H-imidazol-4-yl)propionamide;

N—[(R)-2-[3-(2,6-difluorophenyl)-3-pentylazetidin-1-yl]-1-(4-methoxybenzyl)-2-oxoethyl]-3-(1H-imidazol-4-yl)propionamide;

N-[2-(3-butoxy-3-o-tolylazetidin-1-yl)-1-(4-methoxybenzyl)-2-oxoethyl]-3-(1H-imidazol-4-yl)hexyramide;

N-[2-(3-butoxy-3-o-tolylazetidin-1-yl)-1-(4-methoxybenzyl)-2-oxoethyl]-3-(1H-imidazol-4-yl)pentyramide;

N—[(R)-1-(4-methoxybenzyl)-2-oxo-2-(3-pentyl-3-phenylazetidin-1-yl)ethyl]-3-(3-methyl-3H-imidazol-4-yl)propionamide;

N—[(R)-2-(3-cyclohexyl-3-pentylazetidin-1-yl)-1-(4-methoxybenzyl)-2-oxoethyl]-3-(1H-imidazol-4-yl)propionamide;

N—[(R)-2-(3-butoxy-3-o-tolylazetidin-1-yl)-1-(4-methoxybenzyl)-2-oxoethyl]-3-(3-methyl-3H-imidazol-4-yl)propionamide;

N—[(R)-2-[3-butoxy-3-(2-fluorophenyl)azetidin-1-yl]-1-(4-methoxybenzyl)-2-oxoethyl]-3-(1H-imidazol-4-yl)propionamide;

N—[(R)-2-(3-butoxy-3-o-tolylazetidin-1-yl)-1-(4-methoxybenzyl)-2-oxoethyl]-3-(1-methyl-1H-imidazol-4-yl)propionamide;

N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate;

(S)—N—[(R)-2-(3-butoxy-3-o-tolylazetidin-1-yl)-1-(4-methoxybenzyl)-2-oxoethyl]-2-hydroxy-3-(1H-imidazol-4-yl)propionamide;

N-[2-(3-butoxy-3-o-tolylazetidin-1-yl)-1-(4-hydroxybenzyl)-2-oxoethyl]-3-(3H-imidazol-4-yl)propionamide;

N—[(R)-2-(3-butoxy-3-o-tolylazetidin-1-yl)-1-(4-methoxybenzyl)-2-oxoethyl]-3-hydroxy-3-(1H-imidazol-4-yl)propionamide;

N—[(R)-2-(3-but-2-ynyloxy-3-o-tolylazetidin-1-yl)-1-(4-methoxybenzyl)-2-oxoethyl]-3-(1H-imidazol-4-yl)propionamide;

N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide;

N—[(R)-2-(3-cyclohexylmethoxy-3-o-tolylazetidin-1-yl)-1-(4-methoxybenzyl)-2-oxoethyl]-3-(1H-imidazol-4-yl)propionamide;

3-(1H-imidazol-4-yl)-N—{(R)-1-(4-methoxybenzyl)-2-oxo-2-[3-o-tolyl-3-(4,4,4-trifluorobutoxy)azetidin-1-yl]ethylpropionamide;

N—[(R)-2-(3-cyclobutylmethoxy-3-o-tolylazetidin-1-yl)-1-(4-methoxybenzyl)-2-oxoethyl]-3-(5-methyl-1H-imidazol-4-yl)propionamide; and N—{(R)-1-(4-methoxybenzyl)-2-[3-(3-methylbut-2-enyloxy)-3-o-tolylazetidin-1-yl]-2-oxoethyl}-3-(5-methyl-1H-imidazol-4-ylpropionamide;

and the salts and enantiomers thereof.

2. A method for treating a disorder, disease, or dysfunction selected from the group consisting of:

an inflammatory disease of the digestive tract selected from the group consisting of irritable bowel syndrome, ulcerative colitis, Crohn's disease, pancreatitis, hepatitis, an inflammatory pathological condition of the bladder and gastritis;

an inflammatory disease of the locomotor system selected from the group consisting of rheumatoid arthritis, osteoarthritis, osteoporosis, traumatic arthritis, post-infectious arthritis, muscle degeneration and dermatomyositis;

glomerulonephritis;

an inflammatory disease of the cardiac system selected from the group consisting of pericarditis, myocarditis, atherosclerosis, transplant atherosclerosis, peripheral vascular disease, inflammatory vasculardisease, intermittent claudication restenosis, stroke, transient ischaemic attack, myocardial ischaemia, myocardial infarction, hypertension, hyperlipidaemia, coronary artery disease, unstable angina, thrombosis, platelet aggregation induced by thrombin and atheroma plaque formation;

an inflammatory disease of the respiratory and ENT system selected from the group consisting of asthma, acute respiratory distress syndrome, hayfever, allergic rhinitis, chronic obstructive pulmonary disease and allergies;

an inflammatory disease of the central nervous system selected from the group consisting of Alzheimer's disease, other form of dementia, Parkinson's disease, Creutzfeldt Jacob disease, multiple sclerosis and meningitis;

an inflammatory skin disease selected from the group consisting of urticaria, scleroderma, contact dermatitis, atopic dermatitis, psoriasis, ichthyosis, acne and other forms of folliculitis, rosacea and alopecia;

an autoimmune disease selected from the group consisting of lupus erythematosus, a thyroid condition, an autoimmune disease of the adrenal gland, autoimmune gastritis, vitiligo and alopecia areata;

an inflammation accompanying bacterial, viral or fungal infections selected from the group consisting of tuberculosis, septicaemia, fever, HIV, herpes, cytomegalovirus, hepatitis A, hepatitis B and hepatitis C;

a transplant or graft rejection selected from the group consisting of kidney, liver, heart, lung, pancreas, bone marrow, cornea, intestine and skin;

pain selected from the group consisting of post-operative pain, neuromuscular pain, headache, cancer-related pain, dental pain and osteoarticular pain;

a disease with a pigmentation disorder selected from the group consisting of a benign dermatosis selected from the group consisting of vitiligo, albinism, melasma, lentigines, freckles, melanocytic naevi and post inflammatory pigmentation; and a pigmented tumor selected from the group consisting of melanoma and local metastases, regional metastases and systemic metastases thereof;

or a method for inhibiting:

actinic erythema, skin ageing, a skincancer, and a disease in which sunlight accelerates onset selected from the group consisting of xeroderma pigmentosum, basal cell naevus syndrome and familial melanoma;

a photodermatosis due to an exogenous photosensitizing agent selected from the group consisting of furocoumarins, halogenated salicylanilides, local sulphamides, psoralens, tetracyclines, systemic sulphamides, phenothiazines, nalidixic acid, and tricyclic antidepressants;

or for inhibiting a dermatosis attack with photosensitivity which is:

a photoaggravated dermatosis selected from the group consisting of lupus erythematosus, recurrent herpes, congenital poikilodermal and telangiectasic conditions with photosensitivity selected from the group consisting of Bloom syndrome, Cockayne syndrome and Rothmund-Thomson syndrome, actinic lichen planus, actinic granuloma, disseminated superficial actinic porokeratosis, acne rosacea, juvenile acne, bullous dermatosis, Darier's disease, cutaneous lymphoma, psoriasis, atopic dermatitis, contact eczema, follicular mucinosis, erythema multiforme, fixed drug erythema, lymphocytoma cutis, reticular erythema with mucinosis and melasma, a dermatosis with photosensitivity caused by deficiency of the protection system with melanin formation or distribution anomalies selected from the group consisting of oculocutaneous albinism, phenylketonuria, anterior hypophyseal insufficiency, vitiligo, and piebaldism and with DNA repair system deficiency selected from the group consisting of xeroderma pigmentosum and Cockayne syndrome, a dermatosis with photosensitivity caused by metabolic anomalies which is a cutaneous porphyria selected from the group consisting of late cutaneous porphyria, mixed porphyria, erythropoietic protoporphyria, congenital erythropoietic porphyria Günther's disease and erythropoietic coproporphyria, or which is pellagra or a pellagroid erythema or a tryptophan metabolism disorder;

an idiopathic photodermatosis attack selected from the group consisting of polymorphous light eruption, benign summer light eruption, actinic prurigo, persistent photosensitization selected from the group consisting of actino-reticulosis, chronic actinic dermatosis, and photosensitive eczema, solar urticaria, hydroa vacciniforme, juvenile spring eruption and solar pruritus, or for modulating the color of the skin or of the hair and of body hairs by causing the skin to tan by increasing melanin synthesis or causing it to bleach by interfering with melanin synthesis, by preventing hair and body hair from turning white or grey (canities or piebaldism); or for modifying the color of the hair and body hairs in cosmetic indications;

or for modulating sebaceous function in treating:

a condition with hyperseborrhoea selected from the group consisting of acne, seborrhoeic dermatitis, greasy skin and greasy hair, hyperseborrhoea in Parkinson's and epilepsy, and hyperandrogenism;

a condition with decreasing sebaceous secretion selected from the group consisting of xerosis and dry skin;

benign and malignant sebocyte and sebaceous gland proliferation;

an inflammatory condition of the pilosebaceous follicle selected from the group consisting of acne, boils, carbuncles and folliculitis;

a neurodegenerative disorder selected from the group consisting of depression, anxiety, an obsessive-compulsive disorder, a neurosis, a psychosis, insomnia, sleep apnea, and drug abuse;

a male sexual dysfunction selected from the group consisting of impotence, loss of libido, and erectile dysfunction; a female sexual dysfunction selected from the group consisting of sexual stimulation disorders, or disorders related to desire, sexual receptivity, orgasm, and disturbances of the major points of sexual function;

pain, preterm labor, dysmenorrhoea, excessive menstruation, and endometriosis;

a disorder related to weight selected from the group consisting of obesity, anorexia, modification and impairment of appetite, spleen metabolism, innocent intake of fats and carbohydrates; diabetes mellitus;

cancer selected from the group consisting of lung cancer, prostate cancer, colon cancer, breast cancer, ovarian cancer and bone cancer, an angiogenesis disorder, and the formation or growth of a solid tumor, said method comprising administering to a subject in need of such treatment a compound selected from the group consisting of:

N—[(R)-2-(3-butoxy-3-o-tolylazetidin-1-yl)-1-(4-methoxybenzyl)-2-oxoethyl]-3-(1H-imidazol-4-yl)propionamide;

N—[(R)-2-(3-ethoxy-3-o-tolylazetidin-1-yl)-1-(4-methoxybenzyl)-2-oxoethyl]-3-(1H-imidazol-4-yl)propionamide;

N—[(R)-2-(3-cyclopropylmethoxy-3-o-tolylazetidin-1-yl)-1-(4-methoxybenzyl)-2-oxoethyl]-3-(1H-imidazol-4-yl)propionamide;

N—[(R)-1-(4-methoxybenzyl)-2-oxo-2-(3-propoxy-3-o-tolylazetidin-1-yl)ethyl]-3-(1H-imidazol-4-yl)propionamide;

N—[(R)-2-[3-butoxy-3-(4-fluorophenyl)azetidin-1-yl]-1-(4-methoxybenzyl)-2-oxoethyl]-3-(1H-imidazol-4-yl)propionamide;

N—[(R)-1-(4-methoxybenzyl)-2-oxo-2-(3-pentyloxy-3-o-tolylazetidin-1-yl)ethyl]-3-(1H-imidazol-4-yl)propionamide;

N—[(R)-1-(4-methoxybenzyl)-2-oxo-2-(3-pentyl-3-phenylazetidin-1-yl)ethyl]-3-(1H-imidazol-4-yl)propionamide;

N—[(R)-2-(3-butyl-3-phenylazetidin-1-yl)-1-(4-methoxybenzyl)-2-oxoethyl]-3-(1H-imidazol-4-yl)propionamide;

N—[(R)-1-(4-methoxybenzyl)-2-oxo-2-(3-pentyl-3-o-tolylazetidin-1-yl)ethyl]-3-(1H-imidazol-4-yl)propionamide;

N—[(R)-2-[3-(4-fluorophenyl)-3-pentylazetidin-1-yl]-1-(4-methoxybenzyl)-2-oxoethyl]-3-(1H-imidazol-4-yl)propionamide;

N—[(R)-2-(3-butoxy-3-o-tolylazetidin-1-yl)-1-(4-methoxybenzyl)-2-oxoethyl]-3-(5-methyl-3H-imidazol-4-yl)propionamide;

N—{(R)-1-(4-methoxybenzyl)-2-[3-(2-methoxyphenyl)-3-pentylazetidin-1-yl]-2-oxoethyl}-3-(1H-imidazol-4-yl)propionamide;

N—[(R)-2-[3-(2-fluorophenyl)-3-pentylazetidin-1-yl]-1-(4-methoxybenzyl)-2-oxoethyl]-3-(1H-imidazol-4-yl)propionamide;

N—[(R)-2-[3-(2-chlorophenyl)-3-pentylazetidin-1-yl]-1-(4-methoxybenzyl)-2-oxoethyl]-3-(1H-imidazol-4-yl)propionamide;

N—[(R)-2-[3-(2,4-difluorophenyl)-3-pentylazetidin-1-yl]-1-(4-methoxybenzyl)-2-oxoethyl]-3-(1H-imidazol-4-yl)propionamide;

N—[(R)-2-[3-(3,4-dichlorophenyl)-3-pentylazetidin-1-yl]-1-(4-methoxybenzyl)-2-oxoethyl]-3-(1H-imidazol-4-yl)propionamide;

N—[(R)-2-[3-(3-fluorophenyl)-3-pentylazetidin-1-yl]-1-(4-methoxybenzyl)-2-oxoethyl]-3-(1H-imidazol-4-yl)propionamide;

N—[(R)-2-[3-(2,5-difluorophenyl)-3-pentylazetidin-1-yl]-1-(4-methoxybenzyl)-2-oxoethyl]-3-(1H-imidazol-4-yl)propionamide;

N—[(R)-2-[3-(2,6-difluorophenyl)-3-pentylazetidin-1-yl]-1-(4-methoxybenzyl)-2-oxoethyl]-3-(1H-imidazol-4-yl)propionamide;

N—[(R)-2-(3-cyclohexyl-3-pentylazetidin-1-yl)-1-(4-methoxybenzyl)-2-oxoethyl]-3-(1H-imidazol-4-yl)propionamide;

N—[(R)-2-[3-butoxy-3-(2-fluorophenyl)azetidin-1-yl]-1-(4-methoxybenzyl)-2-oxoethyl]-3-(1H-imidazol-4-yl)propionamide;

N—[(R)-2-(3-butoxy-3-o-tolylazetidin-1-yl)-1-(4-methoxybenzyl)-2-oxoethyl]-3-(1-methyl-1H-imidazol-4-yl)propionamide;

N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate;

N-[2-(3-butoxy-3-o-tolylazetidin-1-yl)-1-(4-hydroxybenzyl)-2-oxoethyl]-3-(3H-imidazol-4-yl)propionamide;

N-[1-(3-butoxy-3-o-tolylazetidine-1-carbonyl)-2-hydroxy-2-(4-methoxyphenyl)ethyl]-3-(1H-imidazol-4-yl)propionamide;

N—[(R)-2-(3-butoxy-3-o-tolylazetidin-1-yl)-1-(4-methoxybenzyl)-2-oxoethyl]-3-hydroxy-3-(1H-imidazol-4-yl)propionamide;

N—[(R)-2-(3-but-2-ynyloxy-3-o-tolylazetidin-1-yl)-1-(4-methoxybenzyl)-2-oxoethyl]-3-(1H-imidazol-4-yl)propionamide;

N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide;

N—[(R)-2-(3-cyclohexylmethoxy-3-o-tolylazetidin-1-yl)-1-(4-methoxybenzyl)-2-oxoethyl]-3-(1H-imidazol-4-yl)propionamide;

3-(1H-imidazol-4-yl)-N—{(R)-1-(4-methoxybenzyl)-2-oxo-2-[3-o-tolyl-3-(4,4,4-trifluorobutoxy)-azetidin-1-yl]ethyl}propionamide;

N—[(R)-2-(3-cyclobutyl m ethoxy-3-o-tolylazetidin-1-yl)-1-(4-methoxybenzyl)-2-oxoethyl]-3-(5-methyl-1H-imidazol-4-yl)propionamide; and N—{(R)-1-(4-methoxybenzyl)-2-[3-(3-methylbut-2-eny-loxy)-3-o-tolylazetidin-1-yl]-2-oxoethyl}-3-(5-methyl-1H-imidazol-4-yl)propionamide;
and the salts and enantiomers thereof.

3. A method for treating a disorder, disease, of dysfunction selected from the group consisting of:
an inflammatory disease of the digestive tract selected from the group consisting of irritable bowel syndrome, ulcerative colitis, Crohn's disease, pancreatitis, hepatitis, an inflammatory pathological condition of the bladder and gastritis;
an inflammatory disease of the locomotor system selected from the group consisting of rheumatoid arthritis, osteoarthritis, osteoporosis, traumatic arthritis, post-infectious arthritis, muscle degeneration and dermatomyositis;
glomerulonephritis;
an inflammatory disease of the cardiac system selected from the group consisting of pericarditis, myocarditis, atherosclerosis, transplant atherosclerosis, peripheral vascular disease, inflammatory vasculardisease, intermittent claudication restenosis, stroke, transient ischaemic attack, myocardial ischaemia, myocardial infarction, hypertension, hyperlipidaemia, coronary artery disease, unstable angina, thrombosis, platelet aggregation induced by thrombin and atheroma plaque formation;
an inflammatory disease of the respiratory and ENT system selected from the group consisting of asthma, acute respiratory distress syndrome, hayfever, allergic rhinitis, chronic obstructive pulmonary disease and allergies;
an inflammatory disease of the central nervous system selected from the group consisting of Alzheimer's disease, other form of dementia, Parkinson's disease, Creutzfeldt Jacob disease, multiple sclerosis and meningitis;
an inflammatory skin disease selected from the group consisting of urticaria, scleroderma, contact dermatitis, atopic dermatitis, psoriasis, ichthyosis, acne and other forms of folliculitis, rosacea and alopecia;
an autoimmune disease selected from the group consisting of lupus erythematosus, a thyroid condition, an autoimmune disease of the adrenal gland, autoimmune gastritis, vitiligo and alopecia areata;
an inflammation accompanying bacterial, viral or fungal infections selected from the group consisting of tuberculosis, septicaemia, fever, HIV, herpes, cytomegalovirus, hepatitis A, hepatitis B and hepatitis C;
a transplant or graft rejection selected from the group consisting of kidney, liver, heart, lung, pancreas, bone marrow, cornea, intestine and skin;
pain selected from the group consisting of post-operative pain, neuromuscular pain, headache, cancer-related pain, dental pain and osteoarticular pain;
a disease with a pigmentation disorder selected from the group consisting of a benign dermatosis selected from the group consisting of vitiligo, albinism, melasma, lentigines, freckles, melanocytic naevi and post inflammatory pigmentation; and a pigmented tumor selected from the group consisting of melanoma and local metastases, regional metastases and systemic metastases thereof;
or a method for inhibiting:
actinic erythema, skin ageing, a skincancer, and a disease in which sunlight accelerates onset selected from the group consisting of xeroderma pigmentosum, basal cell naevus syndrome and familial melanoma;
a photodermatosis due to an exogenous photosensitizing agent selected from the group consisting of furocoumarins, halogenated salicylanilides, local sulphamides, psoralens, tetracyclines, systemic sulphamides, phenothiazines, nalidixic acid, and tricyclic antidepressants;
or for inhibiting a dermatosis attack with photosensitivity which is:
a photoaggravated dermatosis selected from the group consisting of lupus erythematosus, recurrent herpes, congenital poikilodermal and telangiectasic conditions with photosensitivity selected from the group consisting of Bloom syndrome, Cockayne syndrome and Rothmund-Thomson syndrome, actinic lichen planus, actinic granuloma, disseminated superficial actinic porokeratosis, acne rosacea, juvenile acne, bullous dermatosis, Darier's disease, cutaneous lymphoma, psoriasis, atopic dermatitis, contact eczema, follicular mucinosis, erythema multiforme, fixed drug erythema, lymphocytoma cutis, reticular erythema with mucinosis and melasma,
a dermatosis with photosensitivity caused by deficiency of the protection system with melanin formation or distribution anomalies selected from the group consisting of oculocutaneous albinism, phenylketonuria, anterior hypophyseal insufficiency, vitiligo, and piebaldism and with DNA repair system deficiency selected from the group consisting of xeroderma pigmentosum and Cockayne syndrome,
a dermatosis with photosensitivity caused by metabolic anomalies which is a cutaneous porphyria selected from the group consisting of late cutaneous porphyria, mixed porphyria, erythropoietic protoporphyria, congenital erythropoietic porphyria Günther's disease and erythropoietic coproporphyria, or which is pellagra or a pellagroid erythema or a tryptophan metabolism disorder;
an idiopathic photodermatosis attack selected from the group consisting of PMLE (polymorphous light eruption), benign summer light eruption, actinic prurigo, persistent photosensitization selected from the group consisting of actino-reticulosis, chronic actinic dermatosis, and photosensitive eczema, solar urticaria, hydroa vacciniforme, juvenile spring eruption and solar pruritus,
or for modulating the color of the skin or of the hair and of body hairs by causing the skin to tan by increasing melanin synthesis or causing it to bleach by interfering with melanin synthesis, by preventing hair and body hair from turning white or grey; or for modifying the color of the hair and body hairs in cosmetic indications;
or for modulating sebaceous function in treating:
a condition with hyperseborrhoea selected from the group consisting of acne, seborrhoeic dermatitis, greasy skin and greasy hair, hyperseborrhoea in Parkinson's and epilepsy, and hyperandrogenism;
a condition with decreasing sebaceous secretion selected from the group consisting of xerosis and dry skin;
benign and malignant sebocyte and sebaceous gland proliferation;
an inflammatory condition of the pilosebaceous follicle selected from the group consisting of acne, boils, carbuncles and folliculitis;
a neurodegenerative disorder selected from the group consisting of depression, anxiety, an obsessive-compulsive disorder, a neurosis, a psychosis, insomnia, sleep apnea, and drug abuse;
a male sexual dysfunction selected from the group consisting of impotence, loss of libido, and erectile dysfunction; a female sexual dysfunction selected from the group consisting of sexual stimulation disorders, or disorders related to desire, sexual receptivity, orgasm, and disturbances of the major points of sexual function; pain, preterm labor, dysmenorrhoea, excessive menstruation, and endometriosis;
a disorder related to weight selected from the group consisting of obesity, anorexia, modification and impairment of appetite, spleen metabolism, innocent intake of fats and carbohydrates; diabetes mellitus;
cancer selected from the group consisting of lung cancer, prostate cancer, colon cancer, breast cancer, ovarian cancer and bone cancer, an angiogenesis disorder, and the formation or growth of a solid tumor,
said method comprising administering to a subject in need of such treatment the compound N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate.

4. The method according to claim 1, wherein the disorder, disease, or dysfunction is selected from the group consisting of:
a skin disease selected from the group consisting of urticaria, scleroderma, contact dermatitis, atopic dermatitis, psoriasis, ichthyosis, acne and other forms of folliculitis, rosacea and alopecia;
an autoimmune disease selected from the group consisting of lupus erythematosus, a thyroid condition, an autoimmune disease of the adrenal gland, autoimmune gastritis, vitiligo and alopecia areata;
a disease with a pigmentation disorder selected from the group consisting of a benign dermatosis selected from the group consisting of vitiligo, albinism, melasma, lentigines, freckles, melanocytic naevi and a post-inflammatory pigmentation disorder; and a pigmented tumor selected from the group consisting of melanoma and local metastases, regional metastases and systemic metastases thereof;
actinic erythema, skin ageing, a skin cancer, and a disease in which sunlight accelerates onset selected from the group consisting of xeroderma pigmentosum, basal cell naevus syndrome and familial melanoma;
a photodermatosis due to an exogenous photosensitizing agent selected from the group consisting of furocoumarins, halogenated salicylanilides, local sulphamides, psoralens, tetracyclines, systemic sulphamides, phenothiazines, nalidixic acid, and tricyclic antidepressants;
a dermatosis attack with photosensitivity which is:
a photoaggravated dermatosis selected from the group consisting of lupus erythematosus, recurrent herpes, congenital poikilodermal and a telangiectasic condition with photosensitivity selected from the group consisting of Bloom syndrome, Cockayne syndrome and Rothmund-Thomson syndrome, actinic lichen planus, actinic granuloma, disseminated superficial actinic porokeratosis, acne rosacea, juvenile acne, bullous dermatosis, Darier's disease, cutaneous lymphoma, psoriasis, atopic dermatitis, contact eczema, follicular mucinosis, erythema multiforme, fixed drug erythema, lymphocytoma cutis, reticular erythema with mucinosis and melasma, a dermatosis with photosensitivity caused by deficiency of the protection system with melanin formation or distribution anomalies selected from the group consisting of oculocutaneous albinism, phenylketonuria, anterior hypophyseal insufficiency, vitiligo and piebaldism) and with DNA repair system deficiency selected from the group consisting of xeroderma pigmentosum and Cockayne syndrome,
a dermatosis with photosensitivity caused by metabolic anomalies which is a cutaneous porphyria selected from the group consisting of late cutaneous porphyria, mixed porphyrias, erythropoietic protoporphyria, congenital erythropoietic porphyria, Günther's disease and erythropoietic coproporphyria, or which is pellagra or a pellagroid erythema or a tryptophan metabolism disorder;
an idiopathic photodermatosis attack selected from the group consisting of polymorphous light eruption, benign summer light eruption, actinic prurigo, persistent photosensitization selected from the group consisting of actino-reticulosis, chronic actinic dermatosis, and photosensitive eczema, solar urticaria, hydroa vacciniforme, juvenile spring eruption and solar pruritus;
or wherein the method is for modulating the color of the skin or of the hair and of body hairs by causing the skin to tan by increasing melanin synthesis or causing it to bleach by interfering with melanin synthesis, by inhibiting hair and body hair turning white or grey;
or for modifying the color of the hair and body hairs in cosmetic indications.

5. The method according to claim 2, wherein the disorder, disease, of dysfunction is selected from the group consisting of:
a skin disease selected from the group consisting of urticaria, scleroderma, contact dermatitis, atopic dermatitis, psoriasis, ichthyosis, acne and other forms of folliculitis, rosacea and alopecia;
an autoimmune disease selected from the group consisting of lupus erythematosus, a thyroid condition, an autoimmune disease of the adrenal gland, autoimmune gastritis, vitiligo and alopecia areata;
a disease with a pigmentation disorder selected from the group consisting of a benign dermatosis selected from the group consisting of vitiligo, albinism, melasma, lentigines, freckles, melanocytic naevi and a post-inflammatory pigmentation disorder; and a pigmented tumor selected from the group consisting of melanoma and local metastases, regional metastases and systemic metastases thereof;
actinic erythema, skin ageing, a skin cancer, and a disease in which sunlight accelerates onset selected from the group consisting of xeroderma pigmentosum, basal cell naevus syndrome and familial melanoma;
a photodermatosis due to an exogenous photosensitizing agent selected from the group consisting of furocoumarins, halogenated salicylanilides, local sulphamides, psoralens, tetracyclines, systemic sulphamides, phenothiazines, nalidixic acid, and tricyclic antidepressants;
a dermatosis attack with photosensitivity which is:
a photoaggravated dermatosis selected from the group consisting of lupus erythematosus, recurrent herpes, congenital poikilodermal and a telangiectasic condition with photosensitivity selected from the group consisting of Bloom syndrome, Cockayne syndrome and Rothmund-Thomson syndrome, actinic lichen planus, actinic granuloma, disseminated superficial actinic porokeratosis, acne rosacea, juvenile acne, bullous dermatosis, Darier's disease, cutaneous lymphoma, psoriasis, atopic dermatitis, contact eczema, follicular mucinosis, erythema multiforme, fixed drug erythema, lymphocytoma cutis, reticular erythema with mucinosis and melasma, a dermatosis with photosensitivity caused by deficiency of the protection system with melanin formation or distribution anomalies selected from the group consisting of oculocutaneous albinism, phenylketonuria, anterior hypophyseal insufficiency, vitiligo and piebaldism) and with DNA repair system deficiency selected from the group consisting of xeroderma pigmentosum and Cockayne syndrome, a dermatosis with photosensitivity caused by metabolic anomalies which is a cutaneous porphyria selected from the group consisting of late cutaneous porphyria, mixed porphyrias, erythropoietic protoporphyria, congenital erythropoietic porphyria, Günther's disease and erythropoietic coproporphyria, or which is pellagra or a pellagroid erythema or a tryptophan metabolism disorder;

an idiopathic photodermatosis attack selected from the group consisting of polymorphous light eruption, benign summer light eruption, actinic prurigo, persistent photosensitization selected from the group consisting of actino-reticulosis, chronic actinic dermatosis, and photosensitive eczema, solar urticaria, hydroa vacciniforme, juvenile spring eruption and solar pruritus;

or wherein the method is for modulating the color of the skin or of the hair and of body hairs by causing the skin to tan by increasing melanin synthesis or causing it to bleach by interfering with melanin synthesis, by inhibiting hair and body hair turning white or grey;

or for modifying the color of the hair and body hairs in cosmetic indications.

6. The method according to claim 3, wherein the disorder, disease, or dysfunction is selected from the group consisting of:

a skin disease selected from the group consisting of urticaria, scleroderma, contact dermatitis, atopic dermatitis, psoriasis, ichthyosis, acne and other forms of folliculitis, rosacea and alopecia;

an autoimmune disease selected from the group consisting of lupus erythematosus, a thyroid condition, an autoimmune disease of the adrenal gland, autoimmune gastritis, vitiligo and alopecia areata;

a disease with a pigmentation disorder selected from the group consisting of a benign dermatosis selected from the group consisting of vitiligo, albinism, melasma, lentigines, freckles, melanocytic naevi and a post-inflammatory pigmentation disorder; and a pigmented tumor selected from the group consisting of melanoma and local metastases, regional metastases and systemic metastases thereof;

actinic erythema, skin ageing, a skin cancer, and a disease in which sunlight accelerates onset selected from the group consisting of xeroderma pigmentosum, basal cell naevus syndrome and familial melanoma;

a photodermatosis due to an exogenous photosensitizing agent selected from the group consisting of furocoumarins, halogenated salicylanilides, local sulphamides, psoralens, tetracyclines, systemic sulphamides, phenothiazines, nalidixic acid, and tricyclic antidepressants;

a dermatosis attack with photosensitivity which is:

a photoaggravated dermatosis selected from the group consisting of lupus erythematosus, recurrent herpes, congenital poikilodermal and a telangiectasic condition with photosensitivity selected from the group consisting of Bloom syndrome, Cockayne syndrome and Rothmund-Thomson syndrome, actinic lichen planus, actinic granuloma, disseminated superficial actinic porokeratosis, acne rosacea, juvenile acne, bullous dermatosis, Darier's disease, cutaneous lymphoma, psoriasis, atopic dermatitis, contact eczema, follicular mucinosis, erythema multiforme, fixed drug erythema, lymphocytoma cutis, reticular erythema with mucinosis and melasma, a dermatosis with photosensitivity caused by deficiency of the protection system with melanin formation or distribution anomalies selected from the group consisting of oculocutaneous albinism, phenylketonuria, anterior hypophyseal insufficiency, vitiligo and piebaldism and with DNA repair system deficiency selected from the group consisting of xeroderma pigmentosum and Cockayne syndrome, a dermatosis with photosensitivity caused by metabolic anomalies which is a cutaneous porphyria selected from the group consisting of late cutaneous porphyria, mixed porphyrias, erythropoietic protoporphyria, congenital erythropoietic porphyria, Günther's disease and erythropoietic coproporphyria, or which is pellagra or a pellagroid erythema or a tryptophan metabolism disorder;

an idiopathic photodermatosis attack selected from the group consisting of polymorphous light eruption, benign summer light eruption, actinic prurigo, persistent photosensitization selected from the group consisting of actino-reticulosis, chronic actinic dermatosis, and photosensitive eczema, solar urticaria, hydroa vacciniforme, juvenile spring eruption and solar pruritus;

or wherein the method is for modulating the color of the skin or of the hair and of body hairs by causing the skin to tan by increasing melanin synthesis or causing it to bleach by interfering with melanin synthesis, by inhibiting hair and body hair turning white or grey;

or for modifying the color of the hair and body hairs in cosmetic indications.

7. The method according to claim 1, wherein the disease, disorder, or dysfunction is selected from the group consisting of:

a condition with hyperseborrhoea selected from the group consisting of acne, seborrhoeic dermatitis, greasy skin and greasy hair, hyperseborrhoea in Parkinson's and epilepsy, and hyperandrogenism;

a condition with decreased sebaceous secretion selected from the group consisting of xerosis and dry skin;

benign and malignant sebocyte and sebaceous gland proliferation;

an inflammatory condition of the pilosebaceous follicle selected from the group consisting of acne, boils, carbuncles and folliculitis.

8. The method according to claim 2, wherein the disease, disorder, or dysfunction is selected from the group consisting of:

a condition with hyperseborrhoea selected from the group consisting of acne, seborrhoeic dermatitis, greasy skin and greasy hair, hyperseborrhoea in Parkinson's and epilepsy, and hyperandrogenism;

a condition with decreased sebaceous secretion selected from the group consisting of xerosis and dry skin;

benign and malignant sebocyte and sebaceous gland proliferation;

an inflammatory condition of the pilosebaceous follicle selected from the group consisting of acne, boils, carbuncles and folliculitis.

9. The method according to claim 3, wherein the disease, disorder, or dysfunction is selected from the group consisting of:
- a condition with hyperseborrhoea selected from the group consisting of acne, seborrhoeic dermatitis, greasy skin and greasy hair, hyperseborrhoea in Parkinson's and epilepsy, and hyperandrogenism;
- a condition with decreased sebaceous secretion selected from the group consisting of xerosis and dry skin;
- benign and malignant sebocyte and sebaceous gland proliferation;
- an inflammatory condition of the pilosebaceous follicle selected from the group consisting of acne, boils, carbuncles and folliculitis.

10. The method according to claim 4, wherein the disorder, disease, or dysfunction is selected from the group consisting of:
- a skin disease selected from the group consisting of urticaria, scleroderma, contact dermatitis, atopic dermatitis, psoriasis, ichthyosis, acne and other forms of folliculitis, rosacea and alopecia; and
- a disease with a pigmentation disorder selected from the group consisting of a benign dermatosis selected from the group consisting of vitiligo, albinism, melasma, lentigines, freckles, melanocytic naevi and a post-inflammatory pigmentation disorder and a pigmented tumor selected from the group consisting of melanoma and local metastases, regional metastases and systemic metastases thereof.

11. The method according to claim 5, wherein the disorder, disease, or dysfunction is selected from the group consisting of:
- a skin disease selected from the group consisting of urticaria, scleroderma, contact dermatitis, atopic dermatitis, psoriasis, ichthyosis, acne and other forms of folliculitis, rosacea and alopecia; and
- a disease with a pigmentation disorder selected from the group consisting of a benign dermatosis selected from the group consisting of vitiligo, albinism, melasma, lentigines, freckles, melanocytic naevi and a post-inflammatory pigmentation disorder and a pigmented tumor selected from the group consisting of melanoma and local metastases, regional metastases and systemic metastases thereof.

12. The method according to claim 6, wherein the disorder, disease, or dysfunction is selected from the group consisting of:
- a skin disease selected from the group consisting of urticaria, scleroderma, contact dermatitis, atopic dermatitis, psoriasis, ichthyosis, acne and other forms of folliculitis, rosacea and alopecia; and
- a disease with a pigmentation disorder selected from the group consisting of a benign dermatosis selected from the group consisting of vitiligo, albinism, melasma, lentigines, freckles, melanocytic naevi and a post-inflammatory pigmentation disorder and a pigmented tumor selected from the group consisting of melanoma and local metastases, regional metastases and systemic metastases thereof.

13. The method as defined in claim 1, wherein the method is for treating signs of ageing skin, said method comprising applying the composition as defined in claim 1 to the skin of a subject in need of such treatment.

14. The method as defined by claim 1 wherein the method is for treating signs of ageing skin, said method comprising applying the composition as defined in claim 1 to the skin of a subject in need of such treatment and the compound is N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate.

15. The method as defined by claim 1 wherein the method is for body or hair hygiene, said method comprising applying to the body or the hair of a subject in need of such treatment for body or hair hygiene, a composition as defined in claim 1.

16. The method as defined by claim 1, for body or hair hygiene, said method comprising applying to the body or the hair of a subject in need of such treatment for body or hair hygiene and the compound is N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate; a composition as defined in claim 1.

17. A method for modulating a melanocortin receptor MC1R or MC4R in a cell, said method comprising contacting the cell with a melanocortin receptor MC1R or MC4R modulating amount of a compound selected from the group consisting of:
- N—[(S)-1-[(S)-2-(3-butoxy-3-o-tolylazetidin-1-yl)-1-(4-methoxybenzyl)-2-oxoethylcarbamoyl]-2-(1H-imidazol-4-yl)ethyl]benzamide;
- N—[(S)-1-[(S)-2-(3-butoxy-3-phenylazetidin-1-yl)-1-(4-methoxybenzyl)-2-oxoethylcarbamoyl]-2-(1H-imidazol-4-yl)ethyl]benzamide;
- N—[(S)-1-[(S)-2-[3-butoxy-3-(4-fluorophenyl)azetidin-1-yl]-1-(4-methoxybenzyl)-2-oxoethylcarbamoyl]-2-(1H-imidazol-4-yl)ethyl]benzamide;
- N—[(S)-1-[(S)-2-[3-butoxy-3-(3-fluorophenyl)azetidin-1-yl]-1-(4-methoxybenzyl)-2-oxoethylcarbamoyl]-2-(1H-imidazol-4-yl)ethyl]benzamide;
- N—[(R)-2-(3-butoxy-3-o-tolylazetidin-1-yl)-1-(4-methoxybenzyl)-2-oxoethyl]-3-(1H-imidazol-4-yl)propionamide;
- N—[(R)-2-(3-ethoxy-3-o-tolylazetidin-1-yl)-1-(4-methoxybenzyl)-2-oxoethyl]-3-(1H-imidazol-4-yl)propionamide;
- N—[(R)-2-(3-butoxy-3-phenylazetidin-1-yl)-1-(2,4-dichlorobenzyl)-2-oxoethyl]-3-(1H-imidazol-4-yl)propionamide;
- N—[(R)-2-(3-cyclopropyl methoxy-3-o-tolylazetidin-1-yl)-1-(4-methoxybenzyl)-2-oxoethyl]-3-(1H-imidazol-4-yl)propionamide;
- N—[(R)-1-(4-methoxybenzyl)-2-oxo-2-(3-propoxy-3-o-tolylazetidin-1-yl)ethyl]-3-(1H-imidazol-4-yl)propionamide;
- N—[(R)-2-[3-butoxy-3-(4-fluorophenyl)azetidin-1-yl]-1-(4-methoxybenzyl)-2-oxoethyl]-3-(1H-imidazol-4-yl)propionamide;
- N—[(R)-1-(4-methoxybenzyl)-2-oxo-2-(3-pentyloxy-3-o-tolylazetidin-1-yl)ethyl]-3-(1H-imidazol-4-yl)propionamide;
- N—[(R)-1-(4-methoxybenzyl)-2-oxo-2-(3-pentyl-3-phenylazetidin-1-yl)ethyl]-3-(1H-imidazol-4-yl)propionamide;
- N—[(R)-2-(3-butyl-3-phenylazetidin-1-yl)-1-(4-methoxybenzyl)-2-oxoethyl]-3-(1H-imidazol-4-yl)propionamide;
- N—[(R)-2-[3-butoxy-3-(4-fluorophenyl)azetidin-1-yl]-1-(3-fluorobenzyl)-2-oxoethyl]-3-(1H-imidazol-4-yl)propionamide;

N—[(R)-2-(3-butoxy-3-phenylazetidin-1-yl)-1-(4-fluorobenzyl)-2-oxoethyl]-3-(1H-imidazol-4-yl)propionamide;
N—[(R)-1-benzyl-2-(3-butoxy-3-phenylazetidin-1-yl)-2-oxoethyl]-3-(1H-imidazol-4-yl)propionamide;
N—[(R)-1-(4-methoxybenzyl)-2-oxo-2-(3-pentyl-3-o-tolylazetidin-1-yl)ethyl]-3-(1H-imidazol-4-yl)propionamide;
N—[(R)-2-[3-(4-fluorophenyl)-3-pentylazetidin-1-yl]-1-(4-methoxybenzyl)-2-oxoethyl]-3-(1H-imidazol-4-yl)propionamide;
N—[(R)-2-(3-butoxy-3-o-tolylazetidin-1-yl)-1-(4-methoxybenzyl)-2-oxoethyl]-3-(5-methyl-3H-[1,2,4]triazol-3-yl)propionamide;
N—[(R)-2-(3-butoxy-3-o-tolylazetidin-1-yl)-1-(4-methoxybenzyl)-2-oxoethyl]-3-(5-methyl-3H-imidazol-4-yl)propionamide;
N—{(R)-1-(4-methoxybenzyl)-2-[3-(2-methoxyphenyl)-3-pentylazetidin-1-yl]-2-oxoethyl}-3-(1H-imidazol-4-yl)propionamide;
N—[(R)-2-[3-(2-fluorophenyl)-3-pentylazetidin-1-yl]-1-(4-methoxybenzyl)-2-oxoethyl]-3-(1H-imidazol-4-yl)propionamide;
N—[(R)-2-[3-(2-chlorophenyl)-3-pentylazetidin-1-yl]-1-(4-methoxybenzyl)-2-oxoethyl]-3-(1H-imidazol-4-yl)propionamide;
N—[(R)-1-benzyl-2-oxo-2-(3-pentyl-3-phenylazetidin-1-yl)ethyl]-3-(1H-imidazol-4-yl)propionamide;
N—[(R)-2-[3-(2,4-difluorophenyl)-3-pentylazetidin-1-yl]-1-(4-methoxybenzyl)-2-oxoethyl]-3-(1H-imidazol-4-yl)propionamide;
N—[(R)-2-[3-(3,4-dichlorophenyl)-3-pentylazetidin-1-yl]-1-(4-methoxybenzyl)-2-oxoethyl]-3-(1H-imidazol-4-yl)propionamide;
N—[(R)-2-[3-(3,4-dichlorophenyl)-3-pentylazetidin-1-yl]-1-(4-methoxybenzyl)-2-oxoethyl]-3-(1H-imidazol-4-yl)propionamide;
N—[(R)-2-[3-(3-fluorophenyl)-3-pentylazetidin-1-yl]-1-(4-methoxybenzyl)-2-oxoethyl]-3-(1H-imidazol-4-yl)propionamide;
N—[(R)-1-(2,4-dichlorobenzyl)-2-oxo-2-(3-pentyl-3-phenylazetidin-1-yl)ethyl]-3-(1H-imidazol-4-yl)propionamide;
N—[(R)-2-[3-(2,5-difluorophenyl)-3-pentylazetidin-1-yl]-1-(4-methoxybenzyl)-2-oxoethyl]-3-(1H-imidazol-4-yl)propionamide;
N—[(R)-2-[3-(2,6-difluorophenyl)-3-pentylazetidin-1-yl]-1-(4-methoxybenzyl)-2-oxoethyl]-3-(1H-imidazol-4-yl)propionamide;
N-[2-(3-butoxy-3-o-tolylazetidin-1-yl)-1-(4-methoxybenzyl)-2-oxoethyl]-3-(1H-imidazol-4-yl)hexyramide;
N-[2-(3-butoxy-3-o-tolylazetidin-1-yl)-1-(4-methoxybenzyl)-2-oxoethyl]-3-(1H-imidazol-4-yl)pentyramide;
N—[(R)-1-(4-methoxybenzyl)-2-oxo-2-(3-pentyl-3-phenylazetidin-1-yl)ethyl]-3-(3-methyl-3H-imidazol-4-yl)propionamide;
N—[(R)-2-(3-cyclohexyl-3-pentylazetidin-1-yl)-1-(4-methoxybenzyl)-2-oxoethyl]-3-(1H-imidazol-4-yl)propionamide;
N—[(R)-2-(3-butoxy-3-o-tolylazetidin-1-yl)-1-(4-methoxybenzyl)-2-oxoethyl]-3-(3-methyl-3H-imidazol-4-yl)propionamide;
N—[(R)-2-[3-butoxy-3-(2-fluorophenyl)azetidin-1-yl]-1-(4-methoxybenzyl)-2-oxoethyl]-3-(1H-imidazol-4-yl)propionamide;
N—[(R)-2-(3-butoxy-3-o-tolylazetidin-1-yl)-1-(4-methoxybenzyl)-2-oxoethyl]-3-(1-methyl-1H-imidazol-4-yl)propionamide;
N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate;
(S)—N—[(R)-2-(3-butoxy-3-o-tolylazetidin-1-yl)-1-(4-methoxybenzyl)-2-oxoethyl]-2-hydroxy-3-(1H-imidazol-4-yl)propionamide;
N-[2-(3-butoxy-3-o-tolylazetidin-1-yl)-1-(4-hydroxybenzyl)-2-oxoethyl]-3-(3H-imidazol-4-yl)propionamide;
N—[(R)-2-(3-butoxy-3-o-tolylazetidin-1-yl)-1-(4-methoxybenzyl)-2-oxoethyl]-3-hydroxy-3-(1H-imidazol-4-yl)propionamide;
N—[(R)-2-(3-but-2-ynyloxy-3-o-tolylazetidin-1-yl)-1-(4-methoxybenzyl)-2-oxoethyl]-3-(1H-imidazol-4-yl)propionamide;
N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide;
N—[(R)-2-(3-cyclohexylmethoxy-3-o-tolylazetidin-1-yl)-1-(4-methoxybenzyl)-2-oxoethyl]-3-(1H-imidazol-4-yl)propionamide;
3-(1H-imidazol-4-yl)-N—{(R)-1-(4-methoxybenzyl)-2-oxo-2-[3-o-tolyl-3-(4,4,4-trifluorobutoxy)azetidin-1-yl]ethylpropionamide;
N—[(R)-2-(3-cyclobutylmethoxy-3-o-tolylazetidin-1-yl)-1-(4-methoxybenzyl)-2-oxoethyl]-3-(5-methyl-1H-imidazol-4-yl)propionamide; and
N—{(R)-1-(4-methoxybenzyl)-2-[3-(3-methylbut-2-enyloxy)-3-o-tolylazetidin-1-yl]-2-oxoethyl}-3-(5-methyl-1H-imidazol-4-ylpropionamide;
and the salts and enantiomers thereof.

18. A method for modulating a melanocortin receptor MC1R or MC4R in a cell, said method comprising contacting the cell with a melanocortin receptor MC1R or MC4R modulating amount of a compound selected from the group consisting of:

N—[(R)-2-(3-butoxy-3-o-tolylazetidin-1-yl)-1-(4-methoxybenzyl)-2-oxoethyl]-3-(1H-imidazol-4-yl)propionamide;
N—[(R)-2-(3-ethoxy-3-o-tolylazetidin-1-yl)-1-(4-methoxybenzyl)-2-oxoethyl]-3-(1H-imidazol-4-yl)propionamide;
N—[(R)-2-(3-cyclopropyl methoxy-3-o-tolylazetidin-1-yl)-1-(4-methoxybenzyl)-2-oxoethyl]-3-(1H-imidazol-4-yl)propionamide;
N—[(R)-1-(4-methoxybenzyl)-2-oxo-2-(3-propoxy-3-o-tolylazetidin-1-yl)ethyl]-3-(1H-imidazol-4-yl)propionamide;
N—[(R)-2-[3-butoxy-3-(4-fluorophenyl)azetidin-1-yl]-1-(4-methoxybenzyl)-2-oxoethyl]-3-(1H-imidazol-4-yl)propionamide;
N—[(R)-1-(4-methoxybenzyl)-2-oxo-2-(3-pentyloxy-3-o-tolylazetidin-1-yl)ethyl]-3-(1H-imidazol-4-yl)propionamide;
N—[(R)-1-(4-methoxybenzyl)-2-oxo-2-(3-pentyl-3-phenylazetidin-1-yl)ethyl]-3-(1H-imidazol-4-yl)propionamide;
N—[(R)-2-(3-butyl-3-phenylazetidin-1-yl)-1-(4-methoxybenzyl)-2-oxoethyl]-3-(1H-imidazol-4-yl)propionamide;
N—[(R)-1-(4-methoxybenzyl)-2-oxo-2-(3-pentyl-3-o-tolylazetidin-1-yl)ethyl]-3-(1H-imidazol-4-yl)propionamide;

N—[(R)-2-[3-(4-fluorophenyl)-3-pentylazetidin-1-yl]-1-(4-methoxybenzyl)-2-oxoethyl]-3-(1H-imidazol-4-yl)propionamide;
N—[(R)-2-(3-butoxy-3-o-tolylazetidin-1-yl)-1-(4-methoxybenzyl)-2-oxoethyl]-3-(5-methyl-3H-imidazol-4-yl)propionamide;
N—{(R)-1-(4-methoxybenzyl)-2-[3-(2-methoxyphenyl)-3-pentylazetidin-1-yl]-2-oxoethyl}-3-(1H-imidazol-4-yl)propionamide;
N—[(R)-2-[3-(2-fluorophenyl)-3-pentylazetidin-1-yl]-1-(4-methoxybenzyl)-2-oxoethyl]-3-(1H-imidazol-4-yl)propionamide;
N—[(R)-2-[3-(2-chlorophenyl)-3-pentylazetidin-1-yl]-1-(4-methoxybenzyl)-2-oxoethyl]-3-(1H-imidazol-4-yl)propionamide;
N—[(R)-2-[3-(2,4-difluorophenyl)-3-pentylazetidin-1-yl]-1-(4-methoxybenzyl)-2-oxoethyl]-3-(1H-imidazol-4-yl)propionamide;
N—[(R)-2-[3-(3,4-dichlorophenyl)-3-pentylazetidin-1-yl]-1-(4-methoxybenzyl)-2-oxoethyl]-3-(1H-imidazol-4-yl)propionamide;
N—[(R)-2-[3-(3-fluorophenyl)-3-pentylazetidin-1-yl]-1-(4-methoxybenzyl)-2-oxoethyl]-3-(1H-imidazol-4-yl)propionamide;
N—[(R)-2-[3-(2,5-difluorophenyl)-3-pentylazetidin-1-yl]-1-(4-methoxybenzyl)-2-oxoethyl]-3-(1H-imidazol-4-yl)propionamide;
N—[(R)-2-[3-(2,6-difluorophenyl)-3-pentylazetidin-1-yl]-1-(4-methoxybenzyl)-2-oxoethyl]-3-(1H-imidazol-4-yl)propionamide;
N—[(R)-2-(3-cyclohexyl-3-pentylazetidin-1-yl)-1-(4-methoxybenzyl)-2-oxoethyl]-3-(1H-imidazol-4-yl)propionamide;
N—[(R)-2-[3-butoxy-3-(2-fluorophenyl)azetidin-1-yl]-1-(4-methoxybenzyl)-2-oxoethyl]-3-(1H-imidazol-4-yl)propionamide;
N—[(R)-2-(3-butoxy-3-o-tolylazetidin-1-yl)-1-(4-methoxybenzyl)-2-oxoethyl]-3-(1-methyl-1H-imidazol-4-yl)propionamide;
N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate;
N-[2-(3-butoxy-3-o-tolylazetidin-1-yl)-1-(4-hydroxybenzyl)-2-oxoethyl]-3-(3H-imidazol-4-yl)propionamide;
N-[1-(3-butoxy-3-o-tolylazetidine-1-carbonyl)-2-hydroxy-2-(4-methoxyphenyl)ethyl]-3-(1H-imidazol-4-yl)propionamide;
N—[(R)-2-(3-butoxy-3-o-tolylazetidin-1-yl)-1-(4-methoxybenzyl)-2-oxoethyl]-3-hydroxy-3-(1H-imidazol-4-yl)propionamide;
N—[(R)-2-(3-but-2-ynyloxy-3-o-tolylazetidin-1-yl)-1-(4-methoxybenzyl)-2-oxoethyl]-3-(1H-imidazol-4-yl)propionamide;
N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide;
N—[(R)-2-(3-cyclohexylmethoxy-3-o-tolylazetidin-1-yl)-1-(4-methoxybenzyl)-2-oxoethyl]-3-(1H-imidazol-4-yl)propionamide;
3-(1H-imidazol-4-yl)-N—{(R)-1-(4-methoxybenzyl)-2-oxo-2-[3-o-tolyl-3-(4,4,4-trifluorobutoxy)-azetidin-1-yl]ethylpropionamide;
N—[(R)-2-(3-cyclobutylmethoxy-3-o-tolylazetidin-1-yl)-1-(4-methoxybenzyl)-2-oxoethyl]-3-(5-methyl-1H-imidazol-4-yl)propionamide; and
N—{(R)-1-(4-methoxybenzyl)-2-[3-(3-methylbut-2-enyloxy)-3-o-tolylazetidin-1-yl]-2-oxoethyl}-3-(5-methyl-1H-imidazol-4-yl)propionamide;
and the salts and enantiomers thereof.

19. A method for modulating a melanocortin receptor MC1R or MC4R in a cell, said method comprising contacting the cell with a melanocortin receptor MC1R or MC4R modulating amount of the compound N-[2-(3-butoxy-3-o-tolylazetidin-1-yl)-1-(2-hydroxy-4-methoxybenzyl)-2-oxoethyl]-3-(3H-imidazol-4-yl)propionamide trifluoroacetate.

* * * * *